United States Patent
Saxena

(10) Patent No.: US 11,661,603 B2
(45) Date of Patent: May 30, 2023

(54) COMPOSITIONS AND METHODS FOR INHIBITING ALDH2 EXPRESSION

(71) Applicant: Dicerna Pharmaceuticals, Inc., Lexington, MA (US)

(72) Inventor: Utsav Saxena, Lexington, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 54 days.

(21) Appl. No.: 16/961,918

(22) PCT Filed: Jan. 15, 2019

(86) PCT No.: PCT/US2019/013672
§ 371 (c)(1),
(2) Date: Jul. 13, 2020

(87) PCT Pub. No.: WO2019/143621
PCT Pub. Date: Jul. 25, 2019

(65) Prior Publication Data
US 2021/0380984 A1    Dec. 9, 2021

Related U.S. Application Data

(60) Provisional application No. 62/617,692, filed on Jan. 16, 2018.

(51) Int. Cl.
*C12N 15/11*   (2006.01)
*C12N 15/113*   (2010.01)

(52) U.S. Cl.
CPC ...... *C12N 15/1137* (2013.01); *C12N 2310/14* (2013.01); *C12N 2310/315* (2013.01); *C12N 2310/321* (2013.01); *C12N 2310/322* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 8,372,968 B2 | 2/2013 | Tuschl et al. | |
| 8,513,207 B2 | 8/2013 | Brown | |
| 8,883,996 B2 | 11/2014 | Rossi et al. | |
| 8,927,513 B2 | 1/2015 | Manoharan et al. | |
| 8,927,705 B2 | 1/2015 | Brown | |
| 9,012,138 B2 | 4/2015 | Tuschl et al. | |
| 9,012,621 B2 | 4/2015 | Tuschl et al. | |
| 9,193,753 B2 | 11/2015 | Tuschl et al. | |
| 9,567,587 B2 | 2/2017 | Freier et al. | |
| 2003/0032788 A1 | 2/2003 | Garver et al. | |
| 2005/0246794 A1* | 11/2005 | Khvorova | C12N 15/1137 536/23.1 |
| 2007/0254362 A1 | 11/2007 | Quay et al. | |
| 2008/0274462 A1 | 11/2008 | Jeon et al. | |
| 2009/0099115 A1 | 4/2009 | McSwiggen et al. | |
| 2010/0081705 A1 | 4/2010 | Bennett et al. | |
| 2011/0294869 A1 | 12/2011 | Petersen | |
| 2014/0248338 A1 | 9/2014 | MacLachlan et al. | |
| 2022/0170025 A1 | 6/2022 | Brown et al. | |

FOREIGN PATENT DOCUMENTS

| | | |
|---|---|---|
| KR | 20120005240 A | 1/2012 |
| WO | 200116346 A1 | 3/2001 |
| WO | 2005116265 A2 | 12/2005 |
| WO | 2010033225 A2 | 3/2010 |
| WO | 2011133871 A2 | 10/2011 |
| WO | 2013052677 A1 | 4/2013 |
| WO | 2014088920 A1 | 6/2014 |
| WO | 2015169973 A2 | 11/2015 |
| WO | 2015188197 A2 | 12/2015 |
| WO | 2016100401 A1 | 6/2016 |
| WO | 2016183009 A2 | 11/2016 |
| WO | 2018039364 A1 | 3/2018 |
| WO | 2018045317 A1 | 3/2018 |
| WO | 2018185239 A1 | 10/2018 |
| WO | 2018185241 A1 | 10/2018 |
| WO | 2019075419 A1 | 4/2019 |
| WO | 2019092282 A1 | 5/2019 |
| WO | 2019092283 A1 | 5/2019 |
| WO | 2019143621 A1 | 7/2019 |
| WO | 2020206350 A1 | 10/2020 |
| WO | 2022104366 A2 | 5/2022 |

OTHER PUBLICATIONS

Abe et al. "Dumbbell-shaped nanocircular RNAs for RNA interference," J Am Chem Soc. 2007; 129(49): 15108-15109.
Antao et al., "A thermodynamic study of unusually stable RNA and DNA hairpins," Nucleic Acids Res. 1991; 19(21) 5901-5905.
Bennett et al. "Pharmacology of Antisense Drugs," Annual Review of Pharmacology and Toxicology. 2017; 57: 81-105.
Bertola et al., "Mouse model of chronic and binge ethanol feeding (the NIAAA model)," Nature Protocols. 2013; 8(3): 627-637.
Brandon-Warner et al., "Rodent Models of Alcoholic Liver Disease: Of Mice and Men," Alcohol. 2012; 46(8): 715-725.
Bramsen et al., "Improved silencing properties using small internally segmented interfering RNAs," Nucleic Acids Res. 2007; 35(17): 5886-5897.
Bramsen et al., "A large-scale chemical modification screen identifies design rules to generate siRNAs with high activity, high stability and low toxicity," Nucleic Acids Res. 2009; 37(9): 2867-2881.

(Continued)

*Primary Examiner* — Ekaterina Poliakova-Georgantas
(74) *Attorney, Agent, or Firm* — Dechert LLP; Andrea L. C. Reid; Gang Wang

(57) ABSTRACT

This disclosure relates to oligonucleotides, compositions and methods useful for reducing ALDH2 expression, particularly in hepatocytes. Disclosed oligonucleotides for the reduction of ALDH2 expression may be double-stranded or single-stranded, and may be modified for improved characteristics such as stronger resistance to nucleases and lower immunogenicity. Disclosed oligonucleotides for the reduction of ALDH2 expression may also include targeting ligands to target a particular cell or organ, such as the hepatocytes of the liver, and may be used to treat alcoholism and related conditions.

25 Claims, 17 Drawing Sheets

Specification includes a Sequence Listing.

(56) References Cited

OTHER PUBLICATIONS

Chang et al., "Asymmetric shorter-duplex siRNA structures trigger efficient gene silencing with reduced nonspecific effects," Mol Ther. 2009; 17(4): 725-732.
Cheong et al., "Solution structure of an unusually stable RNA hairpin, 5'GGAC(UUCG)GUCC," Nature. 1990; 346(6285): 680-682.
Cornish-Bowden, "Nomenclature for incompletely specified bases in nucleic acid sequences: recommendations 1984," Nucl. Acids Res. 1985; 13(9): 3021-3030.
Dellinger et al., "Solid-phase chemical synthesis of phosphonoacetate and thiophosphonoacetate oligodeoxynucleotides," J. Am. Chem. Soc. 2003; 125(4): 940-950.
Hamilton et al., "Two classes of short interfering RNA in RNA silencing," Embo J. 2002; 21(17): 4671-4679.
Heus et al., "Structural features that give rise to the unusual stability of RNA hairpins containing GNRA loops," Science. 1991; 253(5016): 191-194.
Hohjoh, "Enhancement of RNAi activity by improved siRNA duplexes," FEBS Letters. 2004; 557(1-3): 193-198.
Huch et al., "In vitro expansion of single Lgr5+ liver stem cells induced by Wnt-driven regeneration," Nature. 2013; 494(7436): 247-250.
Imanishi et al., "BNAs: novel nucleic acid analogs with a bridged sugar moiety," The Royal Society of Chemistry, Chem. Common. 2002; 16: 1653-1659.
International Search Report and Written Opinion issued by the United States Patent and Trademark Office as International Searching Authority for International Application No. PCT/US2019/013672, dated May 23, 2019 (13 pages).
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron. 1998; 54(14): 3607-3630.
Loakes et al., "3-Nitropyrrole and 5-nitroindole as universal bases in primers for DNA sequencing and PCR," Nucleic Acids Res. 1995; 23(13): 2361-2366.
Loakes et al., "5-Nitroindole as an universal base analogue," Nucleic Acids Res. 1994; 22(20): 4039-4043.
Matsui et al., "Argonaute 2-dependent Regulation of Gene Expression by Single-stranded miRNA Mimics," Molecular Therapy. 2016; 24(5): 946-955.
Meade et al., "Efficient delivery of RNAi prodrugs containing reversible charge-neutralizing phosphotriester backbone modifications," Nature Biotechnology. 2014; 32(12): 1256-1261.
Moore et al., "Short hairpin RNA (shRNA): design, delivery, and assessment of gene knockdown," Methods Mol. Biol. 2010; 629: 141-158.
Nakano et al., "Selection for thermodynamically stable DNA tetraloops using temperature gradient gel electrophoresis reveals four motifs: d(cGNNAg), d(cGNABg),d(cCNNGg), and d(gCNNGc)," Biochemistry. 2002; 41(48): 14281-14292.
Prakash et al., "Identification of metabolically stable 5'-phosphate analogs that support single-stranded siRNA activity," Nucleic Acids Res. 2015; 43(6): 2993-3011.
Rijk et al., "A mouse model of alcoholism" Physiol. Behav. 1982; 29(5): 833-839.
Snead et al., "5' Unlocked Nucleic Acid Modification Improves siRNA Targeting," Mol Ther Nucleic Acids. 2013; 2: e103.
Sun et al., "Asymmetric RNA duplexes mediate RNA interference in mammalian cells," Nat. Biotechnol. 2008; 26(12): 1379-1382.
Van Aerschot et al., "An acyclic 5-nitroindazole nucleoside analogue as ambiguous nucleoside," Nucleic Acids Res. 1995; 23(21): 4363-4370.
Woese et al., "Architecture of ribosomal RNA: constraints on the sequence of "tetra-Ioops"," Proc Natl Acad Sci USA. 1990; 87(21): 8467-8471.
Chang et al., "ALDH2 polymorphism and alcohol-related cancers in Asians: a public health perspective," J Biomed Sci. 2017;24(1):19.
Cortinez et al., "RNA interference against aldehyde dehydrogenase-2: development of tools for alcohol research," Alcohol. Mar. 2009;43(2):97-104.
Mali et al., "Impaired ALDH2 activity decreases the mitochondrial respiration in H9C2 cardiomyocytes," Cell Signal. Feb. 2016;28(2):1-6.
PCT International Search Report from PCT/US2020/026717 dated Jul. 8, 2020.
Scoles and Pulst, "Oligonucleotide therapeutics in neurodegenerative diseases," RNA Biol. 2018;15(6):707-714.
PCT International Search Report from PCT/US2021/072370 dated Feb. 2, 2022.

\* cited by examiner

```
                         SEQUENCE LISTING

<160> NUMBER OF SEQ ID NOS: 610

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1
gaggucuucu gcaaccagau uuuca                                           25

<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 2
aggucuucug caaccagauu uucat                                           25

<210> SEQ ID NO 3
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 3
gucuucugca accagauuuu cauaa                                           25

<210> SEQ ID NO 4
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 4
cuucugcaac cagauuuuca uaaac                                           25

<210> SEQ ID NO 5
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 5
uucugcaacc agauuuucau aaaca                                           25

<210> SEQ ID NO 6
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 6
ucugcaacca gauuucaua aacaa                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
cugcaaccag auuucauaa acaat                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
ugcaaccaga uuucauaaa caatg                                          25

<210> SEQ ID NO 9
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 9
gcaaccagau uucauaaac aauga                                          25

<210> SEQ ID NO 10
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 10
caaccagauu ucauaaaca augaa                                          25

<210> SEQ ID NO 11
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 11
aaccagauuu ucauaaacaa ugaat                                         25

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 12
accagauuuu cauaaacaau gaatg                                         25
```

```
<210> SEQ ID NO 13
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 13
ccagauuuuc auaaacaaug aaugg                                          25

<210> SEQ ID NO 14
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 14
cagauuuuca uaaacaauga auggc                                          25

<210> SEQ ID NO 15

<400> SEQUENCE: 15

000

<210> SEQ ID NO 16

<400> SEQUENCE: 16

000

<210> SEQ ID NO 17
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 17
agauuuucau aaacaaugaa uggca                                          25

<210> SEQ ID NO 18
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 18
gauuuucaua aacaaugaau ggcac                                          25

<210> SEQ ID NO 19
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 19
gccgucagca ggaaaacauu cccca                                          25

<210> SEQ ID NO 20
<211> LENGTH: 25
<212> TYPE: RNA
<213> ORGANISM: Artificial Sequence
```

```
<220> FEATURE:
<223> OTHER INFORMATION: Synthetic Polynucleotide

<400> SEQUENCE: 20
ccgucagcag gaaaacauuc cccac                                              25

<210> SEQ ID NO 21
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 21
ggccuuggag acccuggaca auggc                                              25

<210> SEQ ID NO 22
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 22
gccuuggaga cccuggacaa uggca                                              25

<210> SEQ ID NO 23
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 23
ccuuggagac ccuggacaau ggcaa                                              25

<210> SEQ ID NO 24
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 24
uaccuggugg auuggacau ggucc                                               25

<210> SEQ ID NO 25
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 25
accuggugga uuggacaug gucct                                               25

<210> SEQ ID NO 26
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 26
ccugguggau uggacaugg uccuc                                               25
```

```
<210> SEQ ID NO 27
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 27
cugguggauu uggacauggu ccuca                                        25

<210> SEQ ID NO 28
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 28
ugguggauuu ggacaugguc cucaa                                        25

<210> SEQ ID NO 29
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 29
gguggauuug gacauggucc ucaaa                                        25

<210> SEQ ID NO 30
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 30
guggauuugg acaugguccu caaat                                        25

<210> SEQ ID NO 31
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 31
uggauuugga caugguccuc aaatg                                        25

<210> SEQ ID NO 32
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 32
gauuuggaca ugguccucaa augtc                                        25

<210> SEQ ID NO 33
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 33
uucccgcucc ugaugcaagc augga                                              25

<210> SEQ ID NO 34
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 34
ucccgcuccu gaugcaagca uggaa                                              25

<210> SEQ ID NO 35
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 35
cccgcuccug augcaagcau ggaag                                              25

<210> SEQ ID NO 36
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 36
ccgcuccuga ugcaagcaug gaagc                                              25

<210> SEQ ID NO 37
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 37
cgcuccugau gcaagcaugg aagct                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 38
gcuccugaug caagcaugga agctg                                              25

<210> SEQ ID NO 39
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 39
cuccugaugc aagcauggaa gcugg                                              25
```

-continued

```
<210> SEQ ID NO 40
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 40
uccugaugca agcauggaag cuggg                                              25

<210> SEQ ID NO 41
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 41
aacuggaaac gugguuguga ugaag                                              25

<210> SEQ ID NO 42
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 42
acuggaaacg ugguugugau gaagg                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 43
cuggaaacgu gguugugaug aaggt                                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 44
uggaaacgug guugugauga aggta                                              25

<210> SEQ ID NO 45
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 45
ggaaacgugg uugugaugaa gguag                                              25

<210> SEQ ID NO 46
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 46
gaaacguggu ugugaugaag guagc                                         25

<210> SEQ ID NO 47
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 47
aacgugguug ugaugaaggu agctg                                         25

<210> SEQ ID NO 48
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 48
acgugguugu gaugaaggua gcuga                                         25

<210> SEQ ID NO 49
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 49
cgugguugug augaagguag cugag                                         25

<210> SEQ ID NO 50
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 50
guugugauga agguagcuga gcaga                                         25

<210> SEQ ID NO 51
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 51
gugaugaagg uagcugagca gacac                                         25

<210> SEQ ID NO 52
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 52
aggaugugga caaaguggca uucac                                         25
```

```
<210> SEQ ID NO 53
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 53
gggagcagca accucaagag aguga                                  25

<210> SEQ ID NO 54
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 54
ggagcagcaa ccucaagaga gugac                                  25

<210> SEQ ID NO 55
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 55
gagcagcaac cucaagagag ugacc                                  25

<210> SEQ ID NO 56
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 56
agcagcaacc ucaagagagu gacct                                  25

<210> SEQ ID NO 57
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 57
gcagcaaccu caagagagug acctt                                  25

<210> SEQ ID NO 58
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 58
gcccuguucu ucaaccaggg ccagt                                  25

<210> SEQ ID NO 59
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 59
cccuguucuu caaccagggc cagtg                                              25

<210> SEQ ID NO 60
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 60
ccuguucuuc aaccagggcc agugc                                              25

<210> SEQ ID NO 61
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 61 cguucuuca accagggcca gugct                                               25

<210> SEQ ID NO 62
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 62
uguucuucaa ccagggccag ugctg                                              25

<210> SEQ ID NO 63
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 63
guucuucaac cagggccagu gcugc                                              25

<210> SEQ ID NO 64
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 64
uucuucaacc agggccagug cugct                                              25

<210> SEQ ID NO 65
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 65
cuucaaccag ggccagugcu gcugt                                              25
```

```
<210> SEQ ID NO 66
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 66
uucaaccagg gccagugcug cugtg                                              25

<210> SEQ ID NO 67
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 67
caaccagggc cagugcugcu gugcc                                              25

<210> SEQ ID NO 68
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 68
ggcucccgga ccuucgugca ggagg                                              25

<210> SEQ ID NO 69
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 69
gcucccggac cuucgugcag gagga                                              25

<210> SEQ ID NO 70
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 70
cucccggacc uucgugcagg aggac                                              25

<210> SEQ ID NO 71
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 71
ucccggaccu ucgugcagga ggaca                                              25

<210> SEQ ID NO 72
<211> LENGTH: 25
<212> TYPE: DNA
<213> ORGANISM: Artificial Sequence
<220> FEATURE:
<223> OTHER INFORMATION: Synthetic Polynucleotide
```

<400> SEQUENCE: 72
cccggaccuu cgugcaggag gacat                                              25

<210> SEQ ID NO 73
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 73
ccggaccuuc gugcaggagg acatc                                              25

<210> SEQ ID NO 74
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 74
ggaggacauc uaugaugagu uugtg                                              25

<210> SEQ ID NO 75
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 75
cgggccaagu cucggguggu cggga                                              25

<210> SEQ ID NO 76
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 76
gggccaaguc ucgggugguc gggaa                                              25

<210> SEQ ID NO 77
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 77
gcagguggau gaaacucagu uuaag                                              25

<210> SEQ ID NO 78
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 78
cagguggaug aaacucaguu uaaga                                              25

```
<210> SEQ ID NO 79
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 79
agguggauga aacucaguuu aagaa                                    25

<210> SEQ ID NO 80
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 80
gguggaugaa acucaguuua agaag                                    25

<210> SEQ ID NO 81
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 81
guggaugaaa cucaguuuaa gaaga                                    25

<210> SEQ ID NO 82
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 82
uggaugaaac ucaguuuaag aagat                                    25

<210> SEQ ID NO 83
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 83
ggaugaaacu caguuuaaga agatc                                    25

<210> SEQ ID NO 84
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 84
gaugaaacuc aguuuaagaa gaucc                                    25

<210> SEQ ID NO 85
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 85
augaaacuca guuuagaag aucct                                              25

<210> SEQ ID NO 86
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 86
ugaaacucag uuuagaaga uccuc                                              25

<210> SEQ ID NO 87
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 87
gaaacucagu uuagaagau ccucg                                              25

<210> SEQ ID NO 88
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 88
aaacucaguu uagaagauc cucgg                                              25

<210> SEQ ID NO 89
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 89
aacucaguuu aagaagaucc ucggc                                             25

<210> SEQ ID NO 90
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 90
acucaguuua agaagauccu cggct                                             25

<210> SEQ ID NO 91
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 91
cucaguuuaa gaagauccuc ggcta                                             25
```

```
<210> SEQ ID NO 92
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 92
ucaguuuaag aagauccucg gcuac                                                 25

<210> SEQ ID NO 93
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 93
caguuuaaga agauccucgg cuaca                                                 25

<210> SEQ ID NO 94
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 94
aguuuaagaa gauccucggc uacat                                                 25

<210> SEQ ID NO 95
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 95
guuuaagaag auccucggcu acatc                                                 25

<210> SEQ ID NO 96
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 96
uuuaagaaga uccucggcua cauca                                                 25

<210> SEQ ID NO 97
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 97
uuaagaagau ccucggcuac aucaa                                                 25

<210> SEQ ID NO 98
<211> LENGTH: 25
<212> TYPE: RNA
<213> ORGANISM: Artificial Sequence
<220> FEATURE:
<223> OTHER INFORMATION: Synthetic Polynucleotide
```

<400> SEQUENCE: 98
uaagaagauc cucggcuaca ucaac                                          25

<210> SEQ ID NO 99
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 99
aagaagaucc ucggcuacau caaca                                          25

<210> SEQ ID NO 100
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 100
agaagauccu cggcuacauc aacac                                          25

<210> SEQ ID NO 101
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 101
gaagauccuc ggcuacauca acacg                                          25

<210> SEQ ID NO 102
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 102
aagauccucg gcuacaucaa cacgg                                          25

<210> SEQ ID NO 103
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 103
agauccucgg cuacaucaac acggg                                          25

<210> SEQ ID NO 104
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 104
ugcugcugac cgugguuacu ucauc                                          25

```
<210> SEQ ID NO 105
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 105
gcugcugacc gugguuacuu caucc                                   25

<210> SEQ ID NO 106
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 106
cugcugaccg ugguuacuuc aucca                                   25

<210> SEQ ID NO 107
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 107
gcugaccgug guuacuucau ccagc                                   25

<210> SEQ ID NO 108
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 108
ccagugaugc agauccugaa guuca                                   25

<210> SEQ ID NO 109
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 109
agugaugcag auccugaagu ucaag                                   25

<210> SEQ ID NO 110
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 110
gugaugcaga uccugaaguu caaga                                   25

<210> SEQ ID NO 111
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 111
ugaugcagau ccugaaguuc aagac                                         25

<210> SEQ ID NO 112
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 112
gaugcagauc cugaaguuca agacc                                         25

<210> SEQ ID NO 113
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 113
augcagaucc ugaaguucaa gacca                                         25

<210> SEQ ID NO 114
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 114
gcagauccug aaguucaaga ccata                                         25

<210> SEQ ID NO 115
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 115
cagauccuga aguucaagac cauag                                         25

<210> SEQ ID NO 116
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 116
agauccugaa guucaagacc auaga                                         25

<210> SEQ ID NO 117
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 117
gauccugaag uucaagacca uagag                                         25
```

<210> SEQ ID NO 118
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 118
uccugaaguu caagaccaua gagga                                          25

<210> SEQ ID NO 119
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 119
aaguucaaga ccauagagga ggutg                                          25

<210> SEQ ID NO 120
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 120
gcugucuuca caaaggauuu ggaca                                          25

<210> SEQ ID NO 121
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 121
gucuucacaa aggauuugga caagg                                          25

<210> SEQ ID NO 122
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 122
gcaggcauac acugaaguga aaact                                          25

<210> SEQ ID NO 123
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 123
caggcauaca cugaagugaa aactg                                          25

<210> SEQ ID NO 124
<211> LENGTH: 25
<212> TYPE: DNA
<213> ORGANISM: Artificial Sequence
<220> FEATURE:
<223> OTHER INFORMATION: Synthetic Polynucleotide

```
<400> SEQUENCE: 124
aggcauacac ugaagugaaa acugt                                              25

<210> SEQ ID NO 125
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 125
ggcauacacu gaagugaaaa cugtc                                              25

<210> SEQ ID NO 126
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 126
gcauacacug aagugaaaac uguca                                              25

<210> SEQ ID NO 127
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 127
auacacugaa gugaaaacug ucaca                                              25

<210> SEQ ID NO 128
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 128
uacacugaag ugaaaacugu cacag                                              25

<210> SEQ ID NO 129
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 129
cugaagugaa aacugucaca gucaa                                              25

<210> SEQ ID NO 130
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 130
gucaaagugc cucagaagaa cucat                                              25
```

```
<210> SEQ ID NO 131
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 131
caaagugccu cagaagaacu cauaa                                     25

<210> SEQ ID NO 132
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 132
aagugccuca gaagaacuca uaaga                                     25

<210> SEQ ID NO 133
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 133
agugccucag aagaacucau aagaa                                     25

<210> SEQ ID NO 134
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 134
gugccucaga agaacucaua agaat                                     25

<210> SEQ ID NO 135
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 135
ugccucagaa gaacucauaa gaatc                                     25

<210> SEQ ID NO 136
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 136
ccucagaaga acucauaaga aucat                                     25

<210> SEQ ID NO 137
<211> LENGTH: 25
<212> TYPE: DNA
<213> ORGANISM: Artificial Sequence
<220> FEATURE:
<223> OTHER INFORMATION: Synthetic Polynucleotide
```

<400> SEQUENCE: 137
cucagaagaa cucauaagaa ucatg                                              25

<210> SEQ ID NO 138
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 138
ucagaagaac ucauaagaau caugc                                              25

<210> SEQ ID NO 139
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 139
cagaagaacu cauaagaauc augca                                              25

<210> SEQ ID NO 140
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 140
agaagaacuc auaagaauca ugcaa                                              25

<210> SEQ ID NO 141
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 141
gaagaacuca uaagaaucau gcaag                                              25

<210> SEQ ID NO 142
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 142
aagaacucau aagaaucaug caagc                                              25

<210> SEQ ID NO 143
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 143
gaacucauaa gaaucaugca agctt                                              25

```
<210> SEQ ID NO 144
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 144
aacucauaag aaucaugcaa gcutc                                          25

<210> SEQ ID NO 145
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 145
cccucagcca uugauggaaa guuca                                          25

<210> SEQ ID NO 146
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 146
ccucagccau ugauggaaag uucag                                          25

<210> SEQ ID NO 147
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 147
ucagccauug auggaaaguu cagca                                          25

<210> SEQ ID NO 148
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 148
cagccauuga uggaaaguuc agcaa                                          25

<210> SEQ ID NO 149
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 149
agccauugau ggaaaguuca gcaag                                          25

<210> SEQ ID NO 150
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 150
gccauugaug gaaaguucag caaga                                          25

<210> SEQ ID NO 151
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 151
ccauugaugg aaaguucagc aagat                                          25

<210> SEQ ID NO 152
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 152
cauugaugga aaguucagca agatc                                          25

<210> SEQ ID NO 153
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 153
auugauggaa aguucagcaa gauca                                          25

<210> SEQ ID NO 154
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 154
uugauggaaa guucagcaag aucag                                          25

<210> SEQ ID NO 155
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 155
ugauggaaag uucagcaaga ucagc                                          25

<210> SEQ ID NO 156
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 156
gauggaaagu ucagcaagau cagca                                          25
```

```
<210> SEQ ID NO 157
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 157
auggaaaguu cagcaagauc agcaa                                              25

<210> SEQ ID NO 158
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 158
uggaaaguuc agcaagauca gcaac                                              25

<210> SEQ ID NO 159
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 159
ggaaaguuca gcaagaucag caaca                                              25

<210> SEQ ID NO 160
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 160
gaaaguucag caagaucagc aacaa                                              25

<210> SEQ ID NO 161
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 161
aaaguucagc aagaucagca acaaa                                              25

<210> SEQ ID NO 162
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 162
aaguucagca agaucagcaa caaaa                                              25

<210> SEQ ID NO 163
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 163
aucagcaaca aaaccaagaa aaatg                                              25

<210> SEQ ID NO 164
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 164
cagcaacaaa accaagaaaa augat                                              25

<210> SEQ ID NO 165
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 165
agcaacaaaa ccaagaaaaa ugatc                                              25

<210> SEQ ID NO 166
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 166
acaaaaccaa gaaaaaugau ccutg                                              25

<210> SEQ ID NO 167
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 167
caaaaccaag aaaaaugauc cuugc                                              25

<210> SEQ ID NO 168
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 168 agaaaauga uccuugcgug cugaa                                               25

<210> SEQ ID NO 169
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 169
aaaaaugauc cuugcgugcu gaata                                              25
```

```
<210> SEQ ID NO 170
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 170
aaaaugaucc uugcgugcug aauat                                  25

<210> SEQ ID NO 171
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 171
aaaugauccu ugcgugcuga auatc                                  25

<210> SEQ ID NO 172
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 172
aaugauccuu gcgugcugaa uauct                                  25

<210> SEQ ID NO 173
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 173
augauccuug cgugcugaau auctg                                  25

<210> SEQ ID NO 174
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 174
ugauccuugc gugcugaaua ucuga                                  25

<210> SEQ ID NO 175
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 175
gauccuugcg ugcugaauau cugaa                                  25

<210> SEQ ID NO 176
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 176
uccuugcgug cugaauaucu gaaaa                                              25

<210> SEQ ID NO 177
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 177
ccuugcgugc ugaauaucug aaaag                                              25

<210> SEQ ID NO 178
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 178
cuugcgugcu gaauaucuga aaaga                                              25

<210> SEQ ID NO 179
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 179
uugcgugcug aauaucugaa aagag                                              25

<210> SEQ ID NO 180
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 180
ugcgugcuga auaucugaaa agaga                                              25

<210> SEQ ID NO 181
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 181
gcgugcugaa uaucugaaaa gagaa                                              25

<210> SEQ ID NO 182
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 182
cgugcugaau aucugaaaag agaaa                                              25
```

```
<210> SEQ ID NO 183
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 183
gugcugaaua ucugaaaaga gaaat                                          25

<210> SEQ ID NO 184
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 184
ugcugaauau cugaaaagag aaatt                                          25

<210> SEQ ID NO 185
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 185
gcugaauauc ugaaaagaga aautt                                          25

<210> SEQ ID NO 186
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 186
cugaauaucu gaaaagagaa auutt                                          25

<210> SEQ ID NO 187
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 187
ugaauaucug aaaagagaaa uuutt                                          25

<210> SEQ ID NO 188
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 188
gaauaucuga aaagagaaau uuutc                                          25

<210> SEQ ID NO 189
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 189
aauaucugaa aagagaaauu uuucc                                              25

<210> SEQ ID NO 190
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 190
auaucugaaa agagaaauuu uucct                                              25

<210> SEQ ID NO 191
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 191
aucugaaaag agaaauuuuu ccuac                                              25

<210> SEQ ID NO 192
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 192
gaaaagagaa auuuuccua caaaa                                               25

<210> SEQ ID NO 193
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 193
aaaagagaaa uuuuccuac aaaat                                               25

<210> SEQ ID NO 194
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 194
agagaaauuu uccuacaaa auctc                                               25

<210> SEQ ID NO 195
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 195
gagaaauuuu uccuacaaaa ucuct                                              25
```

<210> SEQ ID NO 196
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 196
agaaauuuuu ccuacaaaau cuctt                                    25

<210> SEQ ID NO 197
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 197
cuugggucaa gaaaguucua gaatt                                    25

<210> SEQ ID NO 198
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 198
gggucaagaa aguucuagaa uuuga                                    25

<210> SEQ ID NO 199
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 199
ggucaagaaa guucuagaau uugaa                                    25

<210> SEQ ID NO 200
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 200
gucaagaaag uucuagaauu ugaat                                    25

<210> SEQ ID NO 201
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 201
ucaagaaagu ucuagaauuu gaatt                                    25

<210> SEQ ID NO 202
<211> LENGTH: 25
<212> TYPE: DNA
<213> ORGANISM: Artificial Sequence
<220> FEATURE:
<223> OTHER INFORMATION: Synthetic Polynucleotide

```
<400> SEQUENCE: 202
caagaaaguu cuagaauuug aautg                                              25

<210> SEQ ID NO 203
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 203
aagaaaguuc uagaauuuga auuga                                              25

<210> SEQ ID NO 204
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 204
agaaaguucu agaauugaa uugat                                               25

<210> SEQ ID NO 205
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 205
gaaaguucua gaauuugaau ugata                                              25

<210> SEQ ID NO 206
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 206
aaaguucuag aauugaauu gauaa                                               25

<210> SEQ ID NO 207
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 207
aaguucuaga auugaauug auaaa                                               25

<210> SEQ ID NO 208
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 208
aguucuagaa uugaauuga uaaac                                               25
```

-continued

```
<210> SEQ ID NO 209
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 209
guucuagaau uugaauugau aaaca                                    25

<210> SEQ ID NO 210
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 210
uucuagaauu ugaauugaua aacat                                    25

<210> SEQ ID NO 211
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 211
ucuagaauuu gaauugauaa acatg                                    25

<210> SEQ ID NO 212
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 212
cuagaauuug aauugauaaa caugg                                    25

<210> SEQ ID NO 213
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 213
uagaauuuga auugauaaac auggt                                    25

<210> SEQ ID NO 214
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 214
agaauuugaa uugauaaaca uggtg                                    25

<210> SEQ ID NO 215
<211> LENGTH: 25
<212> TYPE: RNA
<213> ORGANISM: Artificial Sequence
<220> FEATURE:
<223> OTHER INFORMATION: Synthetic Polynucleotide
```

<400> SEQUENCE: 215
gaauuugaau ugauaaacau ggugg                                    25

<210> SEQ ID NO 216
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 216
uaagaguaua ugaggaaccu uuuaa                                    25

<210> SEQ ID NO 217
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 217
aagaguauau gaggaaccuu uuaaa                                    25

<210> SEQ ID NO 218
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 218
agaguauaug aggaaccuuu uaaac                                    25

<210> SEQ ID NO 219
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 219
gaguauauga ggaaccuuuu aaacg                                    25

<210> SEQ ID NO 220
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 220
aguauaugag gaaccuuuua aacga                                    25

<210> SEQ ID NO 221
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 221
guauaugagg aaccuuuuaa acgac                                    25

```
<210> SEQ ID NO 222
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 222
uauaugagga accuuuuaaa cgaca                                              25

<210> SEQ ID NO 223
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 223
augaggaacc uuuuaaacga caaca                                              25

<210> SEQ ID NO 224
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 224
gaggaaccuu uuaaacgaca acaat                                              25

<210> SEQ ID NO 225
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 225
aggaaccuuu uaaacgacaa caata                                              25

<210> SEQ ID NO 226
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 226
gaaccuuuua aacgacaaca auact                                              25

<210> SEQ ID NO 227
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 227
aaccuuuuaa acgacaacaa uactg                                              25

<210> SEQ ID NO 228
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 228
accuuuuaaa cgacaacaau acugc                                              25

<210> SEQ ID NO 229
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 229
ccuuuuaaac gacaacaaua cugct                                              25

<210> SEQ ID NO 230
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 230
cuuuuaaacg acaacaauac ugcta                                              25

<210> SEQ ID NO 231
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 231
uaaacgacaa caauacugcu agctt                                              25

<210> SEQ ID NO 232
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 232
aaacgacaac aauacugcua gcutt                                              25

<210> SEQ ID NO 233
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 233
aacgacaaca auacugcuag cuutc                                              25

<210> SEQ ID NO 234
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 234
cgacaacaau acugcuagcu uucag                                              25
```

```
<210> SEQ ID NO 235
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 235
gacaacaaua cugcuagcuu ucagg                                    25

<210> SEQ ID NO 236
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 236
acaacaauac ugcuagcuuu cagga                                    25

<210> SEQ ID NO 237
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 237
caacaauacu gcuagcuuuc aggat                                    25

<210> SEQ ID NO 238
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 238
aacaauacug cuagcuuuca ggatg                                    25

<210> SEQ ID NO 239
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 239
acaauacugc uagcuuucag gauga                                    25

<210> SEQ ID NO 240
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 240
caauacugcu agcuuucagg augat                                    25

<210> SEQ ID NO 241
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 241
aauacugcua gcuuucagga ugatt                                          25

<210> SEQ ID NO 242
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 242
auacugcuag cuuucaggau gautt                                          25

<210> SEQ ID NO 243
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 243
uacugcuagc uuucaggaug auutt                                          25

<210> SEQ ID NO 244
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 244
acugcuagcu uucaggauga uuutt                                          25

<210> SEQ ID NO 245
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 245
cugcuagcuu ucaggaugau uuuta                                          25

<210> SEQ ID NO 246
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 246
ugcuagcuuu caggaugauu uuuaa                                          25

<210> SEQ ID NO 247
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 247
gcuagcuuuc aggaugauuu uuaaa                                          25
```

```
<210> SEQ ID NO 248
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 248
cuagcuuuca ggaugauuuu uaaaa                                              25

<210> SEQ ID NO 249
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 249
agcuuucagg augauuuuua aaaaa                                              25

<210> SEQ ID NO 250
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 250
gcuuucagga ugauuuuuaa aaaat                                              25

<210> SEQ ID NO 251
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 251
cuuucaggau gauuuuuaaa aaata                                              25

<210> SEQ ID NO 252
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 252
uuucaggaug auuuuuaaaa aauag                                              25

<210> SEQ ID NO 253
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 253
uucaggauga uuuuuaaaaa auaga                                              25

<210> SEQ ID NO 254
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 254
ucaggaugau uuuuaaaaaa uagat                                         25

<210> SEQ ID NO 255
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 255
caggaugauu uuaaaaaau agatt                                          25

<210> SEQ ID NO 256
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 256
aggaugauuu uuaaaaaaua gautc                                         25

<210> SEQ ID NO 257
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 257
ggaugauuuu uaaaaauag auuca                                          25

<210> SEQ ID NO 258
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 258
gaugauuuuu aaaaauaga uucaa                                          25

<210> SEQ ID NO 259
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 259
augauuuuua aaaauagau ucaaa                                          25

<210> SEQ ID NO 260
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 260
ugauuuuuaa aaauagauu caaat                                          25
```

```
<210> SEQ ID NO 261
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 261
gauuuuuaaa aaauagauuc aaatg                                          25

<210> SEQ ID NO 262
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 262
auuuuuaaaa aauagauuca aaugt                                          25

<210> SEQ ID NO 263
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 263
uuuuuaaaaa auagauucaa augtg                                          25

<210> SEQ ID NO 264
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 264
aaacgcuucc uauaacucga guuta                                          25

<210> SEQ ID NO 265
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 265
uauaggggaa gaaaaagcua uugtt                                          25

<210> SEQ ID NO 266
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 266
auaggggaag aaaaagcuau ugutt                                          25

<210> SEQ ID NO 267
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 267 gggaagaaa aagcuauugu uuaca                                          25

<210> SEQ ID NO 268
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 268
gggaagaaaa agcuauuguu uacaa                                         25

<210> SEQ ID NO 269
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 269
ggaagaaaaa gcuauuguuu acaat                                         25

<210> SEQ ID NO 270
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 270
gaagaaaaag cuauuguuua caatt                                         25

<210> SEQ ID NO 271
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 271 aagaaaagc uauuguuuac aauta                                          25

<210> SEQ ID NO 272
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 272 agaaaagcu auuguuuaca auuat                                          25

<210> SEQ ID NO 273
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 273 gaaaagcua uuguuacaa uuata                                           25
```

```
<210> SEQ ID NO 274
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 274
aaaaagcuau uguuuacaau uauat                                    25

<210> SEQ ID NO 275
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 275
aaaagcuauu guuuacaauu auatc                                    25

<210> SEQ ID NO 276
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 276
aaagcuauug uuuacaauua uauca                                    25

<210> SEQ ID NO 277
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 277
aagcuauugu uuacaauuau aucac                                    25

<210> SEQ ID NO 278
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 278
agcuauuguu uacaauuaua ucacc                                    25

<210> SEQ ID NO 279
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 279
gcuauuguuu acaauuauau cacca                                    25

<210> SEQ ID NO 280
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 280
cuauuguuua caauuauauc accat                                              25

<210> SEQ ID NO 281
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 281
uauuguuuac aauuauauca ccatt                                              25

<210> SEQ ID NO 282
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 282
auuguuuaca auuauaucac cauta                                              25

<210> SEQ ID NO 283
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 283
uuguuuacaa uuauaucacc auuaa                                              25

<210> SEQ ID NO 284
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 284
uguuuacaau uauaucacca uuaag                                              25

<210> SEQ ID NO 285
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 285
guuuacaauu auaucaccau uaagg                                              25

<210> SEQ ID NO 286
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 286
uacaauuaua ucaccauuaa ggcaa                                              25
```

```
<210> SEQ ID NO 287
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 287
auuauaucac cauuaaggca acugc                                         25

<210> SEQ ID NO 288
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 288
acugcuacac ccugcuuugu auuct                                         25

<210> SEQ ID NO 289
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 289
cugcuacacc cugcuuugua uuctg                                         25

<210> SEQ ID NO 290
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 290
ugcuacaccc ugcuuuguau ucugg                                         25

<210> SEQ ID NO 291
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 291
ugaaaaucug guugcagaag accucgg                                       27

<210> SEQ ID NO 292
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 292
augaaaaucu gguugcagaa gaccucg                                       27

<210> SEQ ID NO 293
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 293
uuaugaaaau cugguugcag aagaccu                                              27

<210> SEQ ID NO 294
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 294
guuuaugaaa aucugguugc agaagac                                              27

<210> SEQ ID NO 295
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 295
uguuuaugaa aaucugguug cagaaga                                              27

<210> SEQ ID NO 296
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 296
uuguuuauga aaaucugguu gcagaag                                              27

<210> SEQ ID NO 297
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 297
auuguuuaug aaaacuggu ugcagaa                                               27

<210> SEQ ID NO 298
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 298
cauuguuuau gaaaaucugg uugcaga                                              27

<210> SEQ ID NO 299
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 299
ucauuguuua ugaaaaucug guugcag                                              27
```

```
<210> SEQ ID NO 300
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 300
uucauuguuu augaaaaucu gguugca                                              27

<210> SEQ ID NO 301
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 301
auucauuguu uaugaaaauc ugguugc                                              27

<210> SEQ ID NO 302
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 302
cauucauugu uuaugaaaau cugguug                                              27

<210> SEQ ID NO 303
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 303
ccauucauug uuuaugaaaa ucugguu                                              27

<210> SEQ ID NO 304
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 304
gccauucauu guuuaugaaa aucuggu                                              27

<210> SEQ ID NO 305

<400> SEQUENCE: 305

000

<210> SEQ ID NO 306

<400> SEQUENCE: 306

000

<210> SEQ ID NO 307
<211> LENGTH: 27
<212> TYPE: RNA
<213> ORGANISM: Artificial Sequence
```

```
<220> FEATURE:
<223> OTHER INFORMATION: Synthetic Polynucleotide

<400> SEQUENCE: 307
ugccauucau uguuuaugaa aaucugg                                    27

<210> SEQ ID NO 308
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 308
gugccauuca uuguuuauga aaaucug                                    27

<210> SEQ ID NO 309
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 309 ugggggaaugu uuuccugcug acggcau                                   27

<210> SEQ ID NO 310
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 310
guggggaaug uuuuccugcu gacggca                                    27

<210> SEQ ID NO 311
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 311
gccauugucc agggucucca aggccgc                                    27

<210> SEQ ID NO 312
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 312
ugccauuguc cagggucucc aaggccg                                    27

<210> SEQ ID NO 313
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 313
uugccauugu ccaggguucuc caaggcc                                   27
```

```
<210> SEQ ID NO 314
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 314
ggaccauguc caaauccacc agguagg                                          27

<210> SEQ ID NO 315
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 315
aggaccaugu ccaaauccac cagguag                                          27

<210> SEQ ID NO 316
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 316
gaggaccaug uccaaaucca ccaggua                                          27

<210> SEQ ID NO 317
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 317
ugaggaccau guccaaaucc accaggu                                          27

<210> SEQ ID NO 318
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 318
uugaggacca uguccaaauc caccagg                                          27

<210> SEQ ID NO 319
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 319
uuugaggacc auguccaaau ccaccag                                          27

<210> SEQ ID NO 320
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 320
auuugaggac cauguccaaa uccacca                                              27

<210> SEQ ID NO 321
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 321
cauuugagga ccauguccaa auccacc                                              27

<210> SEQ ID NO 322
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 322
gacauuugag gaccaugucc aaaucca                                              27

<210> SEQ ID NO 323
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 323
uccaugcuug caucaggagc gggaaau                                              27

<210> SEQ ID NO 324
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 324
uuccaugcuu gcaucaggag cgggaaa                                              27

<210> SEQ ID NO 325
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 325
cuuccaugcu ugcaucagga gcgggaa                                              27

<210> SEQ ID NO 326
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 326
gcuuccaugc uugcaucagg agcggga                                              27
```

<210> SEQ ID NO 327
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 327
agcuuccaug cuugcaucag gagcggg                                27

<210> SEQ ID NO 328
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 328
cagcuuccau gcuugcauca ggagcgg                                27

<210> SEQ ID NO 329
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 329
ccagcuucca ugcuugcauc aggagcg                                27

<210> SEQ ID NO 330
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 330
cccagcuucc augcuugcau caggagc                                27

<210> SEQ ID NO 331
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 331
cuucaucaca accacguuuc caguugc                                27

<210> SEQ ID NO 332
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 332
ccuucaucac aaccacguuu ccaguug                                27

<210> SEQ ID NO 333
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 333
accuucauca caaccacguu uccaguu                                27

<210> SEQ ID NO 334
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 334
uaccuucauc acaaccacgu uuccagu                                27

<210> SEQ ID NO 335
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 335
cuaccuucau cacaaccacg uuuccag                                27

<210> SEQ ID NO 336
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 336
gcuaccuuca ucacaaccac guuucca                                27

<210> SEQ ID NO 337
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 337
cagcuaccuu caucacaacc acguuuc                                27

<210> SEQ ID NO 338
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 338
ucagcuaccu ucaucacaac cacguuu                                27

<210> SEQ ID NO 339
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 339
cucagcuacc uucaucacaa ccacguu                                27

```
<210> SEQ ID NO 340
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 340
ucugcucagc uaccuucauc acaacca                                              27

<210> SEQ ID NO 341
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 341
gugucugcuc agcuaccuuc aucacaa                                              27

<210> SEQ ID NO 342
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 342
gugaaugcca cuuuguccac auccuca                                              27

<210> SEQ ID NO 343
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 343
ucacucucuu gagguugcug cucccag                                              27

<210> SEQ ID NO 344
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 344
gucacucucu ugagguugcu gcuccca                                              27

<210> SEQ ID NO 345
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 345
ggucacucuc uugagguugc ugcuccc                                              27

<210> SEQ ID NO 346
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 346
aggucacucu cuugagguug cugcucc                                27

<210> SEQ ID NO 347
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 347
aaggucacuc ucuuggagguu gcugcuc                               27

<210> SEQ ID NO 348
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 348
acuggcccug guugaagaac agggcga                               27

<210> SEQ ID NO 349
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 349
cacuggcccu gguugaagaa cagggcg                               27

<210> SEQ ID NO 350
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 350
gcacuggccc ugguugaaga acagggc                               27

<210> SEQ ID NO 351
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 351
agcacuggcc cugguugaag aacaggg                               27

<210> SEQ ID NO 352
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 352
cagcacuggc ccugguugaa gaacagg                               27
```

```
<210> SEQ ID NO 353
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 353
gcagcacugg cccugguuga agaacag                                           27

<210> SEQ ID NO 354
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 354
agcagcacug gcccugguug aagaaca                                           27

<210> SEQ ID NO 355
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 355
acagcagcac uggcccuggu ugaagaa                                           27

<210> SEQ ID NO 356
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 356
cacagcagca cuggcccugg uugaaga                                           27

<210> SEQ ID NO 357
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 357
ggcacagcag cacuggcccu gguugaa                                           27

<210> SEQ ID NO 358
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 358
ccuccugcac gaagguccgg gagccgg                                           27

<210> SEQ ID NO 359
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 359
uccuccugca cgaagguccg ggagccg                                          27

<210> SEQ ID NO 360
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 360
guccuccugc acgaagqucc gggagcc                                          27

<210> SEQ ID NO 361
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 361
uguccuccug cacgaagguc cgggagc                                          27

<210> SEQ ID NO 362
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 362
auguccuccu gcacgaaggu ccgggag                                          27

<210> SEQ ID NO 363
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 363
gauguccucc ugcacgaagg uccggga                                          27

<210> SEQ ID NO 364
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 364
cacaaacuca ucauagaugu ccuccug                                          27

<210> SEQ ID NO 365
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 365
ucccgaccac ccgagacuug gcccggg                                          27
```

```
<210> SEQ ID NO 366
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 366
uucccgacca cccgagacuu ggcccgg                                          27

<210> SEQ ID NO 367
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 367
cuuaaacuga guuucaucca ccugcgg                                          27

<210> SEQ ID NO 368
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 368
ucuuaaacug aguuucaucc accugcg                                          27

<210> SEQ ID NO 369
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 369
uucuuaaacu gaguuucauc caccugc                                          27

<210> SEQ ID NO 370
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 370
cuucuuaaac ugaguuucau ccaccug                                          27

<210> SEQ ID NO 371
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 371
ucuucuuaaa cugaguuuca uccaccu                                          27

<210> SEQ ID NO 372
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 372
aucuucuuaa acugaguuuc auccacc                                    27

<210> SEQ ID NO 373
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 373
gaucuucuua aacugaguuu cauccac                                    27

<210> SEQ ID NO 374
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 374
ggaucuucuu aaacugaguu ucaucca                                    27

<210> SEQ ID NO 375
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 375
aggaucuucu uaaacugagu uucaucc                                    27

<210> SEQ ID NO 376
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 376
gaggaucuuc uuaaacugag uuucauc                                    27

<210> SEQ ID NO 377
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 377
cgaggaucuu cuuaaacuga guuucau                                    27

<210> SEQ ID NO 378
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 378
ccgaggaucu ucuuaaacug aguuuca                                    27
```

```
<210> SEQ ID NO 379
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 379
gccgaggauc uucuuaaacu gaguuuc                                        27

<210> SEQ ID NO 380
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 380
agccgaggau cuucuuaaac ugaguuu                                        27

<210> SEQ ID NO 381
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 381
uagccgagga ucuucuuaaa cugaguu                                        27

<210> SEQ ID NO 382
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 382
guagccgagg aucuucuuaa acugagu                                        27

<210> SEQ ID NO 383
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 383
uguagccgag gaucuucuua aacugag                                        27

<210> SEQ ID NO 384
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 384
auguagccga ggaucuucuu aaacuga                                        27

<210> SEQ ID NO 385
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 385
gauguagccg aggaucuucu uaaacug                                       27

<210> SEQ ID NO 386
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 386
ugauguagcc gaggaucuuc uuaaacu                                       27

<210> SEQ ID NO 387
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 387
uugauguagc cgaggaucuu cuuaaac                                       27

<210> SEQ ID NO 388
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 388
guugauguag ccgaggaucu ucuuaaa                                       27

<210> SEQ ID NO 389
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 389
uguugaugua gccgaggauc uucuuaa                                       27

<210> SEQ ID NO 390
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 390
guguugaugu agccgaggau cuucuua                                       27

<210> SEQ ID NO 391
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 391
cguguugaug uagccgagga ucuucuu                                       27
```

```
<210> SEQ ID NO 392
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 392
ccguguugau guagccgagg aucuucu                                       27

<210> SEQ ID NO 393
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 393
cccguguuga uguagccgag gaucuuc                                       27

<210> SEQ ID NO 394
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 394
gaugaaguaa ccacggucag cagcaau                                       27

<210> SEQ ID NO 395
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 395
ggaugaagua accacgguca gcagcaa                                       27

<210> SEQ ID NO 396
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 396
uggaugaagu aaccacgguc agcagca                                       27

<210> SEQ ID NO 397
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 397
gcuggaugaa guaaccacgg ucagcag                                       27

<210> SEQ ID NO 398
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 398
ugaacuucag gaucugcauc acuggcc                                              27

<210> SEQ ID NO 399
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 399
cuugaacuuc aggaucugca ucacugg                                              27

<210> SEQ ID NO 400
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 400
ucuugaacuu caggaucugc aucacug                                              27

<210> SEQ ID NO 401
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 401
gucuugaacu ucaggaucug caucacu                                              27

<210> SEQ ID NO 402
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 402
ggucuugaac uucaggaucu gcaucac                                              27

<210> SEQ ID NO 403
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 403
uggucuugaa cuucaggauc ugcauca                                              27

<210> SEQ ID NO 404
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 404
uauggucuug aacuucagga ucugcau                                              27
```

```
<210> SEQ ID NO 405
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 405
cuauggucuu gaacuucagg aucugca                                         27

<210> SEQ ID NO 406
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 406
ucuauggucu ugaacuucag gaucugc                                         27

<210> SEQ ID NO 407
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 407
cucuaugguc uugaacuuca ggaucug                                         27

<210> SEQ ID NO 408
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 408
uccucuaugg ucuugaacuu caggauc                                         27

<210> SEQ ID NO 409
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 409
caaccuccuc uauggucuug aacuuca                                         27

<210> SEQ ID NO 410
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 410
uguccaaauc cuuugugaag acagcug                                         27

<210> SEQ ID NO 411
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 411 ccuguccaa auccuuugug aagacag                                          27

<210> SEQ ID NO 412
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 412
aguuuucacu ucaguguaug ccugcag                                         27

<210> SEQ ID NO 413
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 413 caguuucac uucaguguau gccugca                                          27

<210> SEQ ID NO 414
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 414
acaguuuuca cuucagugua ugccugc                                         27

<210> SEQ ID NO 415
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 415
gacaguuuuc acuucagugu augccug                                         27

<210> SEQ ID NO 416
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 416
ugacaguuuu cacuucagug uaugccu                                         27

<210> SEQ ID NO 417
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 417
ugugacaguu uucacuucag uguaugc                                         27
```

```
<210> SEQ ID NO 418
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 418
cugugacagu uuucacuuca guguaug                                27

<210> SEQ ID NO 419
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 419
uugacuguga caguuucac uucagug                                 27

<210> SEQ ID NO 420
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 420
augaguucuu cugaggcacu uugacug                                27

<210> SEQ ID NO 421
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 421
uuaugaguuc uucugaggca cuuugac                                27

<210> SEQ ID NO 422
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 422
ucuuaugagu ucuucugagg cacuuug                                27

<210> SEQ ID NO 423
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 423
uucuuaugag uucuucugag gcacuuu                                27

<210> SEQ ID NO 424
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 424
auucuuauga guucuucuga ggcacuu                                              27

<210> SEQ ID NO 425
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 425
gauucuuaug aguucuucug aggcacu                                              27

<210> SEQ ID NO 426
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 426
augauucuua ugaguucuuc ugaggca                                              27

<210> SEQ ID NO 427
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 427
caugauucuu augaguucuu cugaggc                                              27

<210> SEQ ID NO 428
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 428
gcaugauucu uaugaguucu ucugagg                                              27

<210> SEQ ID NO 429
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 429
ugcaugauuc uuaugaguuc uucugag                                              27

<210> SEQ ID NO 430
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 430
uugcaugauu cuuaugaguu cuucuga                                              27
```

```
<210> SEQ ID NO 431
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 431
cuugcaugau ucuuaugagu ucuucug                                           27

<210> SEQ ID NO 432
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 432
gcuugcauga uucuuaugag uucuucu                                           27

<210> SEQ ID NO 433
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 433
aagcuugcau gauucuuaug aguucuu                                           27

<210> SEQ ID NO 434
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 434
gaagcuugca ugauucuuau gaguucu                                           27

<210> SEQ ID NO 435
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 435
ugaacuuucc aucaauggcu gagggag                                           27

<210> SEQ ID NO 436
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 436
cugaacuuuc caucaauggc ugaggga                                           27

<210> SEQ ID NO 437
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 437
ugcugaacuu uccaucaaug gcugagg                                              27

<210> SEQ ID NO 438
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 438
uugcugaacu uccaucaau ggcugag                                               27

<210> SEQ ID NO 439
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 439
cuugcugaac uuuccaucaa uggcuga                                              27

<210> SEQ ID NO 440
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 440
ucuugcugaa cuuuccauca auggcug                                              27

<210> SEQ ID NO 441
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 441
aucuugcuga acuuuccauc aauggcu                                              27

<210> SEQ ID NO 442
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 442
gaucuugcug aacuuuccau caauggc                                              27

<210> SEQ ID NO 443
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 443
ugaucuugcu gaacuuucca ucaaugg                                              27
```

```
<210> SEQ ID NO 444
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 444
cugaucuugc ugaacuuucc aucaaug                                              27

<210> SEQ ID NO 445
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 445
gcugaucuug cugaacuuuc caucaau                                              27

<210> SEQ ID NO 446
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 446
ugcugaucuu gcugaacuuu ccaucaa                                              27

<210> SEQ ID NO 447
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 447
uugcugaucu ugcugaacuu uccauca                                              27

<210> SEQ ID NO 448
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 448
guugcugauc uugcugaacu uuccauc                                              27

<210> SEQ ID NO 449
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 449
uguugcugau cuugcugaac uuuccau                                              27

<210> SEQ ID NO 450
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 450
uuguugcuga ucuugcugaa cuuucca                              27

<210> SEQ ID NO 451
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 451
uuuguugcug aucuugcuga acuuucc                              27

<210> SEQ ID NO 452
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 452
uuuuguugcu gaucuugcug aacuuuc                              27

<210> SEQ ID NO 453
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 453 cauuuucuu gguuuguug cugaucu                                27

<210> SEQ ID NO 454
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 454 aucauuuuc uugguuugu ugcugau                                27

<210> SEQ ID NO 455
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 455
gaucauuuuu cuugguuug uugcuga                               27

<210> SEQ ID NO 456
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 456
caaggaucau uuucuuggu uuguug                                27
```

```
<210> SEQ ID NO 457
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 457
gcaaggauca uuuucuugg uuuguu                                          27

<210> SEQ ID NO 458
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 458
uucagcacgc aaggaucauu uuucuug                                        27

<210> SEQ ID NO 459
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 459
uauucagcac gcaaggauca uuuuucu                                        27

<210> SEQ ID NO 460
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 460
auauucagca cgcaaggauc auuuuuc                                        27

<210> SEQ ID NO 461
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 461
gauauucagc acgcaaggau cauuuuu                                        27

<210> SEQ ID NO 462
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 462
agauauucag cacgcaagga ucauuuu                                        27

<210> SEQ ID NO 463
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 463
cagauauuca gcacgcaagg aucauuu                                        27

<210> SEQ ID NO 464
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 464
ucagauauuc agcacgcaag gaucauu                                        27

<210> SEQ ID NO 465
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 465
uucagauauu cagcacgcaa ggaucau                                        27

<210> SEQ ID NO 466
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 466
uuuucagaua uucagcacgc aaggauc                                        27

<210> SEQ ID NO 467
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 467
cuuuucagau auucagcacg caaggau                                        27

<210> SEQ ID NO 468
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 468
ucuuuucaga uauucagcac gcaagga                                        27

<210> SEQ ID NO 469
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 469
cucuuuucag auauucagca cgcaagg                                        27
```

```
<210> SEQ ID NO 470
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 470
ucucuuuuca gauauucagc acgcaag                                      27

<210> SEQ ID NO 471
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 471
uucucuuuuc agauauucag cacgcaa                                      27

<210> SEQ ID NO 472
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 472
uuucucuuuu cagauauuca gcacgca                                      27

<210> SEQ ID NO 473
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 473
auuucucuuu ucagauauuc agcacgc                                      27

<210> SEQ ID NO 474
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 474
aauuucucuu uucagauauu cagcacg                                      27

<210> SEQ ID NO 475
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 475
aaauuucucu uuucagauau ucagcac                                      27

<210> SEQ ID NO 476
<211> LENGTH: 27
<212> TYPE: RNA
<213> ORGANISM: Artificial Sequence
<220> FEATURE:
<223> OTHER INFORMATION: Synthetic Polynucleotide
```

-continued

<400> SEQUENCE: 476
aaaauuucuc uuuucagaua uucagca 27

<210> SEQ ID NO 477
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 477
aaaaauuucu cuuuucagau auucagc 27

<210> SEQ ID NO 478
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 478
gaaaaauuuc ucuuuucaga uauucag 27

<210> SEQ ID NO 479
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 479
ggaaaaauuu cucuuuucag auauuca 27

<210> SEQ ID NO 480
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 480
aggaaaaauu ucucuuuuca gauauuc 27

<210> SEQ ID NO 481
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 481
guaggaaaaa uuucucuuuu cagauau 27

<210> SEQ ID NO 482
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 482
uuuuguagga aaaauuucuc uuuucag 27

```
<210> SEQ ID NO 483
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 483
auuuuguagg aaaaauuucu cuuuuca                                              27

<210> SEQ ID NO 484
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 484
gagauuuugu aggaaaaauu ucucuuu                                              27

<210> SEQ ID NO 485
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 485
agagauuuug uaggaaaaau uucucuu                                              27

<210> SEQ ID NO 486
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 486
aagagauuuu guaggaaaaa uuucucu                                              27

<210> SEQ ID NO 487
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 487
aauucuagaa cuuucuugac ccaagag                                              27

<210> SEQ ID NO 488
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 488
ucaaauucua gaacuuucuu gacccaa                                              27

<210> SEQ ID NO 489
<211> LENGTH: 27
<212> TYPE: RNA
<213> ORGANISM: Artificial Sequence
<220> FEATURE:
<223> OTHER INFORMATION: Synthetic Polynucleotide
```

<400> SEQUENCE: 489
uucaaauucu agaacuuucu ugaccca                                              27

<210> SEQ ID NO 490
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 490
auucaaauuc uagaacuuuc uugaccc                                              27

<210> SEQ ID NO 491
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 491
aauucaaauu cuagaacuuu cuugacc                                              27

<210> SEQ ID NO 492
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 492
caauucaaau ucuagaacuu ucuugac                                              27

<210> SEQ ID NO 493
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 493
ucaauucaaa uucuagaacu uucuuga                                              27

<210> SEQ ID NO 494
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 494
aucaauucaa auucuagaac uuucuug                                              27

<210> SEQ ID NO 495
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 495
uaucaauuca aauucuagaa cuuucuu                                              27

```
<210> SEQ ID NO 496
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 496
uuaucaauuc aaauucuaga acuuucu                                              27

<210> SEQ ID NO 497
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 497
uuuaucaauu caaauucuag aacuuuc                                              27

<210> SEQ ID NO 498
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 498
guuuaucaau ucaaauucua gaacuuu                                              27

<210> SEQ ID NO 499
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 499
uguuuaucaa uucaaauucu agaacuu                                              27

<210> SEQ ID NO 500
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 500
auguuuauca auucaaauuc uagaacu                                              27

<210> SEQ ID NO 501
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 501
cauguuuauc aauucaaauu cuagaac                                              27

<210> SEQ ID NO 502
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 502
ccauguuuau caauucaaau ucuagaa                                        27

<210> SEQ ID NO 503
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 503
accauguuua ucaauucaaa uucuaga                                        27

<210> SEQ ID NO 504
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 504
caccauguuu aucaauucaa auucuag                                        27

<210> SEQ ID NO 505
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 505
ccaccauguu uaucaauuca aauucua                                        27

<210> SEQ ID NO 506
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 506
uuaaaagguu ccucauauac ucuuacc                                        27

<210> SEQ ID NO 507
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 507
uuuaaaaggu uccucauaua cucuuac                                        27

<210> SEQ ID NO 508
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 508
guuuaaaagg uuccucauau acucuua                                        27
```

-continued

```
<210> SEQ ID NO 509
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 509
cguuuaaaag guuccucaua uacucuu                                              27

<210> SEQ ID NO 510
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 510
ucguuuaaaa gguuccucau auacucu                                              27

<210> SEQ ID NO 511
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 511
gucguuuaaa agguuccuca uauacuc                                              27

<210> SEQ ID NO 512
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 512
ugucguuuaa aagguuccuc auauacu                                              27

<210> SEQ ID NO 513
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 513
uguugucguu uaaaagguuc cucauau                                              27

<210> SEQ ID NO 514
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 514
auuguugucg uuuaaaaggu uccucau                                              27

<210> SEQ ID NO 515
<211> LENGTH: 27
<212> TYPE: RNA
<213> ORGANISM: Artificial Sequence
<220> FEATURE:
<223> OTHER INFORMATION: Synthetic Polynucleotide
```

<400> SEQUENCE: 515
uauuguuguc guuuaaaagg uuccuca          27

<210> SEQ ID NO 516
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 516
aguauuguug ucguuuaaaa gguuccu          27

<210> SEQ ID NO 517
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 517
caguauuguu gucguuuaaa agguucc          27

<210> SEQ ID NO 518
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 518
gcaguauugu ugucguuuaa aagguuc          27

<210> SEQ ID NO 519
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 519
agcaguauug uugucguuua aaagguu          27

<210> SEQ ID NO 520
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 520
uagcaguauu guugucguuu aaaaggu          27

<210> SEQ ID NO 521
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 521
aagcuagcag uauuguuguc guuuaaa          27

```
<210> SEQ ID NO 522
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 522
aaagcuagca guauuguugu cguuuaa                                              27

<210> SEQ ID NO 523
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 523
gaaagcuagc aguauuguug ucguuua                                              27

<210> SEQ ID NO 524
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 524
cugaaagcua gcaguauugu ugucguu                                              27

<210> SEQ ID NO 525
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 525
ccugaaagcu agcaguauug uugucgu                                              27

<210> SEQ ID NO 526
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 526
uccugaaagc uagcaguauu guugucg                                              27

<210> SEQ ID NO 527
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 527
auccugaaag cuagcaguau uguuguc                                              27

<210> SEQ ID NO 528
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 528
cauccugaaa gcuagcagua uuguugu                                              27

<210> SEQ ID NO 529
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 529
ucauccugaa agcuagcagu auuguug                                              27

<210> SEQ ID NO 530
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 530
aucauccuga aagcuagcag uauuguu                                              27

<210> SEQ ID NO 531
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 531
aaucauccug aaagcuagca guauugu                                              27

<210> SEQ ID NO 532
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 532
aaaucauccu gaaagcuagc aguauug                                              27

<210> SEQ ID NO 533
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 533
aaaaucaucc ugaaagcuag caguauu                                              27

<210> SEQ ID NO 534
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 534
aaaaaucauc cugaaagcua gcaguau                                              27
```

```
<210> SEQ ID NO 535
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 535
uaaaaaucau ccugaaagcu agcagua                                              27

<210> SEQ ID NO 536
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 536
uuaaaaauca uccugaaagc uagcagu                                              27

<210> SEQ ID NO 537
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 537
uuuaaaaauc auccugaaag cuagcag                                              27

<210> SEQ ID NO 538
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 538
uuuuaaaaau cauccugaaa gcuagca                                              27

<210> SEQ ID NO 539
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 539
uuuuuuaaaa aucauccuga aagcuag                                              27

<210> SEQ ID NO 540
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 540
auuuuuuaaa aaucauccug aaagcua                                              27

<210> SEQ ID NO 541
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 541
uauuuuuuaa aaaucauccu gaaagcu                                              27

<210> SEQ ID NO 542
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 542
cuauuuuuua aaaucaucc ugaaagc                                               27

<210> SEQ ID NO 543
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 543
ucuauuuuuu aaaaucauc cugaaag                                               27

<210> SEQ ID NO 544
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 544
aucuauuuuu uaaaaaucau ccugaaa                                              27

<210> SEQ ID NO 545
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 545
aaucuauuuu uuaaaaauca uccugaa                                              27

<210> SEQ ID NO 546
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 546
gaaucuauuu uuuaaaaauc auccuga                                              27

<210> SEQ ID NO 547
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 547
ugaaucuauu uuuuaaaaau cauccug                                              27
```

```
<210> SEQ ID NO 548
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 548
uugaaucuau uuuuuaaaaa ucauccu                                        27

<210> SEQ ID NO 549
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 549
uuugaaucua uuuuuuaaaa aucaucc                                        27

<210> SEQ ID NO 550
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 550
auuugaaucu auuuuuuaaa aaucauc                                        27

<210> SEQ ID NO 551
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 551
cauuugaauc uauuuuuuaa aaaucau                                        27

<210> SEQ ID NO 552
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 552
acauuugaau cuauuuuuua aaaauca                                        27

<210> SEQ ID NO 553
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 553
cacauuugaa ucuauuuuuu aaaaauc                                        27

<210> SEQ ID NO 554
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 554
uaaacucgag uuauaggaag cguuuca                                              27

<210> SEQ ID NO 555
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 555
aacaauagcu uuucuuccc cuauaaa                                               27

<210> SEQ ID NO 556
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 556
aaacaauagc uuuucuucc ccuauaa                                               27

<210> SEQ ID NO 557
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 557
uguaaacaau agcuuuuucu uccccua                                              27

<210> SEQ ID NO 558
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 558
uuguaaacaa uagcuuuuuc uuccccu                                              27

<210> SEQ ID NO 559
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 559
auuguaaaca auagcuuuuu cuucccc                                              27

<210> SEQ ID NO 560
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 560
aauuguaaac aauagcuuuu ucuuccc                                              27
```

```
<210> SEQ ID NO 561
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 561
uaauuguaaa caauagcuuu uucuucc                                           27

<210> SEQ ID NO 562
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 562
auaauuguaa acaauagcuu uucuuc                                            27

<210> SEQ ID NO 563
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 563
uauaauugua aacaauagcu uuucuu                                            27

<210> SEQ ID NO 564
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 564
auauaauugu aaacaauagc uuuucu                                            27

<210> SEQ ID NO 565
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 565
gauauaauug uaaacaauag cuuuuc                                            27

<210> SEQ ID NO 566
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 566
ugauauaauu guaaacaaua gcuuuuu                                           27

<210> SEQ ID NO 567
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 567
gugauauaau uguaaacaau agcuuuu                                            27

<210> SEQ ID NO 568
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 568
ggugauauaa uuguaaacaa uagcuuu                                            27

<210> SEQ ID NO 569
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 569
uggugauaua auuguaaaca auagcuu                                            27

<210> SEQ ID NO 570
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 570
auggugauau aauuguaaac aauagcu                                            27

<210> SEQ ID NO 571
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 571
aauggugaua uaauuguaaa caauagc                                            27

<210> SEQ ID NO 572
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 572
uaauggugau auaauuguaa acaauag                                            27

<210> SEQ ID NO 573
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 573
uuaaugguga uauaauugua aacaaua                                            27
```

```
<210> SEQ ID NO 574
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 574
cuuaauggug auauaauugu aaacaau                                        27

<210> SEQ ID NO 575
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 575
ccuuaauggu gauauaauug uaaacaa                                        27

<210> SEQ ID NO 576
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 576
uugccuuaau ggugauauaa uuguaaa                                        27

<210> SEQ ID NO 577
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 577
gcaguugccu uaauggugau auaauug                                        27

<210> SEQ ID NO 578
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 578
agaauacaaa gcagggugua gcaguug                                        27

<210> SEQ ID NO 579
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 579
cagaauacaa agcagggugu agcaguu                                        27

<210> SEQ ID NO 580
<211> LENGTH: 27
<212> TYPE: RNA
<213> ORGANISM: Artificial Sequence
<220> FEATURE:
<223> OTHER INFORMATION: Synthetic Polynucleotide
```

<400> SEQUENCE: 580
ccagaauaca aagcagggug uagcagu                    27

<210> SEQ ID NO 581
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 581
uucauaaaca augaauggca gcagccgaaa ggcugc          36

<210> SEQ ID NO 582
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 582
ucauaaacaa ugaauggcaa gcagccgaaa ggcugc          36

<210> SEQ ID NO 583
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 583
gaaacguggu ugugaugaag gcagccgaaa ggcugc          36

<210> SEQ ID NO 584
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 584
guugugauga agguagcuga gcagccgaaa ggcugc          36

<210> SEQ ID NO 585
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 585
gguggaugaa acucaguuua gcagccgaaa ggcugc          36

<210> SEQ ID NO 586
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 586
caguuuaaga agauccucgg gcagccgaaa ggcugc          36

```
<210> SEQ ID NO 587
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 587
uuuaagaaga uccucggcua gcagccgaaa ggcugc                              36

<210> SEQ ID NO 588
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 588
guucuagaau uugaauugau gcagccgaaa ggcugc                              36

<210> SEQ ID NO 589
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 589
ccuuuuaaac gacaacaaua gcagccgaaa ggcugc                              36

<210> SEQ ID NO 590
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 590
augauuuuua aaaauagau gcagccgaaa ggcugc                               36

<210> SEQ ID NO 591
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 591
ugccauucau uguuuaugaa gg                                             22

<210> SEQ ID NO 592
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 592
uugccauuca uuguuuauga gg                                             22

<210> SEQ ID NO 593
<211> LENGTH: 22
<212> TYPE: RNA
<213> ORGANISM: Artificial Sequence
<220> FEATURE:
<223> OTHER INFORMATION: Synthetic Polynucleotide
```

<400> SEQUENCE: 593
cuucaucaca accacguuuc gg						22

<210> SEQ ID NO 594
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 594
ucagcuaccu ucaucacaac gg						22

<210> SEQ ID NO 595
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 595
uaaacugagu uucauccacc gg						22

<210> SEQ ID NO 596
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 596
ccgaggaucu ucuuaaacug gg						22

<210> SEQ ID NO 597
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 597
uagccgagga ucuucuuaaa gg						22

<210> SEQ ID NO 598
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 598
aucaauucaa auucuagaac gg						22

<210> SEQ ID NO 599
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 599
uauuguuguc guuuaaaagg gg						22

```
<210> SEQ ID NO 600
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 600
aucuauuuuu uaaaaaucau gg                                              22

<210> SEQ ID NO 601
<211> LENGTH: 93
<212> TYPE: DNA
<213> ORGANISM: Homo sapiens

<400> SEQUENCE: 601
aaccagcagc ccgaggtctt ctgcaaccag attttcataa acaatgaatg gcacgatgcc     60
gtcagcagga aaacattccc caccgtcaat ccg                                  93

<210> SEQ ID NO 602
<211> LENGTH: 101
<212> TYPE: DNA
<213> ORGANISM: Homo sapiens

<400> SEQUENCE: 602
acctacctgg cggccttgga gaccctggac aatggcaagc cctatgtcat ctcctacctg     60
gtggatttgg acatggtcct caaatgtctc cggtattatg c                        101

<210> SEQ ID NO 603
<211> LENGTH: 51
<212> TYPE: DNA
<213> ORGANISM: Homo sapiens

<400> SEQUENCE: 603
ccgtggaatt tcccgctcct gatgcaagca tggaagctgg gcccagcctt g              51

<210> SEQ ID NO 604
<211> LENGTH: 59
<212> TYPE: DNA
<213> ORGANISM: Homo sapiens

<400> SEQUENCE: 604
gccttggcaa ctggaaacgt ggttgtgatg aaggtagctg agcagacacc cctcaccgc      59

<210> SEQ ID NO 605
<211> LENGTH: 71
<212> TYPE: DNA
<213> ORGANISM: Homo sapiens

<400> SEQUENCE: 605
gagcaggggc cgcaggtgga tgaaactcag tttaagaaga tcctcggcta catcaacacg     60
gggaagcaag a                                                          71

<210> SEQ ID NO 606
<211> LENGTH: 52
<212> TYPE: DNA
<213> ORGANISM: Homo sapiens

<400> SEQUENCE: 606
tctcttgggt caagaaagtt ctagaatttg aattgataaa catggtgggt tg             52
```

```
<210> SEQ ID NO 607
<211> LENGTH: 93
<212> TYPE: DNA
<213> ORGANISM: Homo sapiens

<400> SEQUENCE: 607
tgagggtaag agtatatgag gaaccttta aacgacaaca atactgctag ctttcaggat      60
gatttttaaa aaatagattc aaatgtgtta tcc                                  93

<210> SEQ ID NO 608
<211> LENGTH: 2076
<212> TYPE: DNA
<213> ORGANISM: Homo sapiens

<400> SEQUENCE: 608
attggctgcc gcgcggggcg gggagcgggg tcggctcagt ggccctgaga ccctagctct      60
gctctcggtc cgctcgctgt ccgctagccc gctgcgatgt tgcgcgctgc cgcccgcttc     120
gggccccgcc tgggccgccg cctcttgtca gccgccgcca cccaggccgt gcctgccccc     180
aaccagcagc ccgaggtctt ctgcaaccag attttcataa acaatgaatg gcacgatgcc     240
gtcagcagga aaacattccc caccgtcaat ccgtccactg gagaggtcat ctgtcaggta     300
gctgaagggg acaaggaaga tgtggacaag gcagtgaagg ccgcccgggc cgccttccag     360
ctgggctcac cttggcgccg catggacgca tcacacaggg gccggctgct gaaccgcctg     420
gccgatctga tcgagcggga ccggacctac ctggcggcct ggagaccct ggacaatggc     480 aagccctatg tcatctccta cctggtggat ttggacatgg tcctcaaatg tctccggtat     540
tatgccggct gggctgataa gtaccacggg aaaaccatcc ccattgacgg agacttcttc     600
agctacacac gccatgaacc tgtggggtg tgcgggcaga tcattccgtg gaatttcccg     660
ctcctgatgc aagcatggaa gctgggccca gccttggcaa ctggaaacgt ggttgtgatg     720
aaggtagctg agcagacacc cctcaccgcc ctctatgtgg ccaacctgat caaggaggct     780
ggctttcccc ctggtgtggt caacattgtg cctggatttg gccccacggc tggggccgcc     840
attgcctccc atgaggatgt ggacaaagtg gcattcacag ctccactga gattggccgc     900 gtaatccagg ttgctgctgg gagcagcaac ctcaagagag tgaccttgga gctgggggg     960 aagagcccca acatcatcat gtcagatgcc gatatggatt gggccgtgga acaggcccac    1020
ttcgccctgt tcttcaacca gggccagtgc tgctgtgccg gctcccggac cttcgtgcag    1080
gaggacatct atgatgagtt tgtggagcgg agcgttgccc gggccaagtc tcgggtggtc    1140
gggaacccct ttgatagcaa gaccgagcag gggccgcagg tggatgaaac tcagtttaag    1200
aagatcctcg gctacatcaa cacggggaag caagagggg cgaagctgct gtgtggtggg    1260
ggcattgctg ctgaccgtgg ttacttcatc cagcccactg tgtttggaga tgtgcaggat    1320
ggcatgacca tcgccaagga ggagatcttc gggccagtga tgcagatcct gaagttcaag    1380
accatagagg aggttgttgg gagagccaac aattccacgt acgggctggc cgcagctgtc    1440
ttcacaaagg atttggacaa ggccaattac ctgtcccagg ccctccaggc gggcactgtg    1500
tgggtcaact gctatgatgt gtttggagcc cagtcaccct ttggtggcta caagatgtcg    1560
gggagtggcc gggagttggg cgagtacggg ctgcaggcat acactgaagt gaaaactgtc    1620
acagtcaaag tgcctcagaa gaactcataa gaatcatgca agcttcctcc ctcagccatt    1680 gatgaaagt tcagcaagat cagcaacaaa accaagaaaa atgatccttg cgtgctgaat    1740
atctgaaaag agaaattttt cctacaaaat ctcttgggtc aagaaagttc tagaatttga    1800
```

```
attgataaac atggtgggtt ggctgagggt aagagtatat gaggaaccct ttaaacgaca    1860
acaatactgc tagcttttcag gatgattttt aaaaaataga ttcaaatgtg ttatcctctc    1920
tctgaaacgc ttcctataac tcgagtttat aggggaagaa aaagctattg tttacaatta    1980
tatcaccatt aaggcaactg ctacaccctg ctttgtattc tgggctaaga ttcattaaaa    2040
actagctgct cttaacttac aaaaaaaaaa aaaaaa                              2076

<210> SEQ ID NO 609
<211> LENGTH: 2124
<212> TYPE: DNA
<213> ORGANISM: Macaca fascicularis

<400> SEQUENCE: 609
ccctgccctc cgtccgctcg cagcccgcta tcctgctgcc atgttgcgtg ctgccgcccg      60
cttcgggccc cgcctgggcc tccgcttctt gtcagccgcc gccacccagg ccgtgcccgc     120
ccccaaccag cagcccgagg tcttctgcaa caaggacttc agctcccaga agccaggact     180
tggctgttgg acttccagtg ctggagtggc cagggctgtc agtgaaagct tatggaatgc     240
gtgggtgaat gaatctcaac ttttacaaaa caaaatcttc ataaacaatg aatggcacaa     300
tgccgtcagc aggaaaacat tccccacagt caatccgtcc actggagagg tcatctgcca     360
ggtagctgaa ggggacaagg aagatgtgga caaggcagtg aaggccgccc gggccgcctt     420
ccagctgggc tcaccttggc gtcgcatgga cgcgtcacac aggggccggc tgctgaaccg     480
gctggctgat ctgatcgagc gggaccggac ctacctggcg ccttggagac tctggacaa      540 tggcaaaccc tatgtcacct cctacctggt ggatttggac atggtcctca aatgtctccg     600
gtattatgcc ggctgggctg ataagtacca cgggaaaacc attcccattg acggagactt     660
cttcagctac acccgccatg aacctgtggg ggtgtgcggg cagatcattc cgtggaattt     720
cccactcctg atgcaagcat ggaagctggg cccagccttg gcgactggaa acgtggttgt     780
gatgaaggta gctgagcaga cacccctcac tgccctctat gtggccaacc tgatcaagga     840
ggccggcttt ccccctggtg tggtcaacat tgttcctgga tttggcccca gccggggc      900 cgccatcgcc tccatgagg atgtggacaa agtggcattc acaggctcca ccgagattgg     960
ccgcctcatc caggttgctg ccgggagcag caatctcaag agagtgacct tggagctggg    1020
gggaaagagc cccaacatca tcatgtcaga tgccgacatg gactgggccg tggagcaggc    1080
ccacttcgcc ctgttcttca accagggcca atgctgctgt gctggctccc ggaccttcgt    1140
gcaggaggac atctatgacg agtttgtgga gcggagcgtt gcccgggcca agtctcgggt    1200
ggtcgggaac ccctttgaca gcaagaccga gcagggaccg caggtggatg aaactcagtt    1260
taagaagatc ctcggctaca tcaacactgg gaaacaagag ggggcgaagc tgctgtgtgg    1320
tgggggcatt gctgctgacc gtggttactt catccagccc accgtgtttg agatgtgca     1380 ggatggcatg accatcgcca aggaggagat cttcggccca gtgatgcaga tcctgaagtt    1440
caagaccata gaggaagttg ttgggagagc caacaattcc acgtacgggc tggccgcagc    1500
tgtcttcaca aaggatttgg acaaggccaa ttacctgtcc caggccctcc aggcgggcac    1560
cgtgtgggtc aactgctatg atgtgtttgg agcccagtca ccctttggcg gctacaagat    1620
gtcgggcagt ggccgggagc tgggcgagta cggcctgcag gcatacactg aagtgaaaac    1680
tatcacagtc aaagtgcctc agaagaactc ataagaacca tgtgggcttt ctccctcagc    1740
cattgatgga aagttcagca agatcagcga caaaccaag aaaatgatc cttgcgtgct     1800 gaatatctga aaagagaaat tcttcctaca aaatctcttg ggtcaagaaa gttctagaat    1860
```

```
ttgaattgat aaacatggtg ggttggctga gggtaagagt ctatgagaaa ccttttaaat    1920
gacaacaata ctgctagctt tcagggtgca ttttaaaaa atagattcaa atgtcttatc    1980
ctctctctga aacgcctcct gtaacttgag tttataggg aagaaaaagc cattgtttac    2040
aattatatca gcatcaaggc aactgctaca ccctgctttg tattctgggc taagattcat    2100
taaaaacaag ctgctctcaa ctta                                          2124

<210> SEQ ID NO 610
<211> LENGTH: 3883
<212> TYPE: DNA
<213> ORGANISM: Mus musculus

<400> SEQUENCE: 610
attctcttcg ccgccatatc tgcacagatg tgagccttag gcgccagcca ccctgctagg      60
agcgcacacc actctggcta ggcttttctca gggttctgca aactccatct ctgacttggc     120
tttgggagcc aggggtcgcg ccccttaggc cgtgagggc tgggactccc tgaccacgcc      180
cccgtgtctc cgcctcccat tggcggctgc aggggggcgga ggcgaggact tgttcttcaa     240
cgctgcagtc gccctccgat cggcaaggct tctctcggct ccgttcggct cggctcgccc     300
atttcagttc agttcgggtc agttaagctc cgctcagttc agcatgctgc gcgccgcact     360
caccactgtc cgccgcggac cgcgcctgag ccgcctgttg tccgccgccg ccaccagcgc     420
ggtgccagcc cccaaccatc agcctgaggt cttctgcaac cagatcttca ttaacaatga     480
gtggcacgac gccgtcagca ggaaaacatt tcccaccgtc aacccttcca caggggaggt     540
catctgccag gtggccgaag ggaacaagga ggacgtagac aaggcagtga aggctgctcg     600
tgcagccttc cagctgggct cgccctggcg ccgcatggat gcatctgacc ggggccggct     660
gttgtaccga ttggcggatc tcattgaacg ggaccggacc tacctagcgg ccttggagac     720
cctggacaac ggcaagcctt atgtcatctc gtacctggtg gatttggaca tggtcctgaa     780
atgtctccgc tattacgctg gctgggctga caagtaccat gggaaaacca ttcccatcga     840
cggcgacttc ttcagctata cccgccatga gcctgtgggc gtgtgtggac agatcattcc     900
gtggaacttc ccgctcctga tgcaagcatg gaaactgggc ccagccctgg caaccgggaa     960
cgtggtggtg atgaaggtgg ccgagcagac accgctcacc gcgctctacg tggccaactt    1020
gatcaaggag gcaggctttc cccctggcgt ggtcaatatc gttcccggat tcggccctac    1080
cgccggggct gccatcgcat cccatgaggg tgtggacaaa gtggcgttca caggctccac    1140
ggaggttggt cacctaatcc aggtggccgc cgggagcagc aacctcaaga gagtaaccct    1200
ggagctgggg ggaaagagtc ccaacatcat catgtccgac gctgacatgg actgggctgt    1260
ggagcaggcc cactttgccc tgttcttcaa ccagggccag tgctgctgcg caggctcccg    1320
gaccttcgtg caggagaatg tgtatgacga attcgtggaa cgcagcgtgg ctcgggccaa    1380
gtctcgggtg gtggggaacc ccttcgacac ccggacggag caggggcctc aggtggatga    1440
aactcagttt aagaagatcc tcggctacat caaatcggga caacaagaag gggcgaagct    1500
gctgtgtggt ggggcgctg ccgcggaccg tggctacttt atccagccca ccgtgttcgg    1560
ggacgtaaaa gacggcatga ccattgccaa ggaggagatc tttggaccag tgatgcaaat    1620
cctcaaattc aagaccatcg aggaggttgt ggggcgggcc aatgattcta gtatgggct    1680 ggcagccgcc gtcttcacaa aggacctgga taaagccaat tacctgtccc aagctctgca    1740
ggctggcact gtgtgatca actgctacga tgtgtttggg gccagtgtctc catttggggg    1800 ctataagatg tcaggagtg gcagggagct gggcgagtat ggcctgcagg cgtacacaga    1860
```

```
agtgaagacg gttactgtca aagtgccaca gaagaactcg taaagcggca tgcctgcttc  1920
ctcagcccgc acccgaaaac ccaacaagat atactgagaa aaaccgccac acacactgcg  1980
cctccaaaga gaaacccctt caccaaagtg tcttgggtca agaaagaatt ttataaacag  2040
ggcggggctg gtgggggga aagctcctga taaactgggt aggggatgaa gctcaatgca   2100
gaccgatcac gcgtccagat gtgcaggatg ctgccttcaa cctgcagtcc ctaagcagca  2160
aatgagcaat aaaaatcagc agatcaaagc cacggggtca gttctctaag acgtaaattc  2220
tgagtcttat ctctgttgca ttccgtaact ctctgctttg ggaggagaca aggccgtcct  2280
tagaattgaa ttagctctgt ggaacactag cgccttggtg tttactggtc agaagtcatg  2340
aaaggcagga cccctctcta ttcctggata cacgggacgc caggatgtcc ccactatttg  2400
gtgatatcat gtatatctca ttaccctcat ccccatcttg gtacctggga tcttggttct  2460
cacaagtaat tctaggctga cgaggaggga tgtaagctaa agggagggga gtcactattc  2520
ttggctgcag ctacattttg gaatttcaca ctggcctatc tcacaggcca gaggaggtag  2580
tgacacccgt ttgatccttt ccaagggtga gccaggttag gtttcaacca agggacctca  2640
cggctcggca tcagttgcat gctgctaact aacctggagt cgattcagcc aaaagacagt  2700
ttccagaagt ggctctgttc tcccaatctg ttctgcggcc tctttgaggc acagagcaga  2760
gcagagccat gtcatgtgca cagtgcaagg tctgcctctc gaactaccag aaccaagaga  2820
gattggaggt attagtgaca gtggcctgat ggaggtggca ggtgatgcc  cgtgaaggta  2880
gattttcagg gaataagaga atgtggcagt gactggcagc tgcaatgcag actctggttc  2940
aggctatggt cactgcagat gcctggatgt gtgacagatg tgatgacatt gctgaaagac  3000
agagggaccc actcccagtg gaaggccaag agagctcttg agcagggctc cagttacgtg  3060
agctttctcc ctcttgtacc agaaggttcc attcctagag gttttagcta cctgtgacct  3120
ctgccctgtg tataaatggg gttactgtga ctatcccaac cctgccctgt cctaaagtac  3180
cttcaagggc caccttgtgc ccaacctgta gattattccc tatacagaaa tgctcatgat  3240
gtttggcata aaaaaaaat taagccagca attagcaata gtcattgtga gaagttacac  3300
aactcttggt gccgctacgc ttgtgttttg gggtgttgag ttagctctgc atgggtgctg  3360
caatactcaa tcctggaagc ccaggagcca agatggttgc tcgtagctga taggtgggca  3420
aatatgccac gtgggtacaa cggctgcagg catgatgctc acatcgggca cagggccgca  3480
ccgatgcatg cagcctggac cagtgtgtgc ttattttcag aatttccgtt tatactctta  3540
tgctatgcat gacgattagc tgcctggtac ctgccctgag cagggataag caggtcaagt  3600
ccaaggtcca caggagctgg gaagcttagg ggcgaaggtc acagatctta ctcacctagt  3660
gagtgaacaa ggcgtggaga gcaagctgcc atcacaggca caagaaacgg acggtgagct  3720
tagctttaga actagccagt cagaggcaga gctgagggta gaaggctgat gaagccctga  3780
agttgtcctt cgacctccat atacacatcc ctgtatgtgc atgcgcactc aatgaaataa  3840
ataagtaaat acaattttta aagatcaaaa aaaaaaaaa aaa                     3883
```

COMPOSITIONS AND METHODS FOR INHIBITING ALDH2 EXPRESSION

RELATED APPLICATIONS

The application is a national stage filing under U.S.C. § 371 of PCT International Application PCT/US2019/013672, filed Jan. 15, 2019, which claims the benefit under 35 U.S.C. § 119(e) to U.S. Provisional Application No. 62/617,692, filed Jan. 16, 2018, and entitled "COMPOSITIONS AND METHODS FOR INHIBITING ALDH2 EXPRESSION," the entire contents of which are incorporated herein by reference.

FIELD OF THE INVENTION

The present application relates to oligonucleotides and uses thereof, particularly uses relating to the treatment of alcoholism and associated conditions.

REFERENCE TO THE SEQUENCE LISTING

The present application is being filed along with a Sequence Listing in electronic format. The Sequence Listing is provided as a filed entitled Dicerna_174867_SEQ.txt created on Jul. 9, 2020 which is 128 kilobytes size. The information in electronic format of the Sequence Listing is incorporated herein by reference in its entirety.

BACKGROUND OF THE INVENTION

Acetaldehyde is an intermediary in the oxidation of alcohol by the body. When acetaldehyde metabolism is inhibited, acetaldehyde accumulates, resulting in the occurrence of toxic symptoms and great discomfort. Mitochondrial aldehyde dehydrogenase (ALDH2) is an enzyme that has a major role in detoxification of acetaldehyde in the body. Genetic polymorphisms of human ALDH2 have been well surveyed among a wide range of ethnic groups. Individuals heterozygous or homozygous for the abnormal gene have lower ALDH2 enzymatic activity, and this deficiency is manifested by facial flushing, nausea, and cardiac palpitations following alcohol consumption. Studies have revealed a reduced prevalence of alcoholism among these individuals, which has been attributed to these unpleasant effects. Therefore, interference with ALDH2 activity can decrease a human's alcohol tolerance and desire to consume alcohol. Pharmacological compounds targeting ALDH2 have been used to induce alcohol aversion in humans.

For example, disulfiram is a compound which interferes with the metabolism of acetaldehyde in vivo by inhibiting ALDH2 enzyme. Alcohol consumption within 12 hours of disulfiram administration can produce facial flushing, throbbing in head and neck, nausea, vomiting, sweating, and dizziness, among other symptoms. Disulfiram has clinical limitations, however, due to a range of side-effects, such as drowsiness, headache and, less often, neurotoxicity. Moreover, because daily administration is typically required for disulfiram and similar therapeutics to be effective, these drugs suffer from extremely poor patient compliance.

BRIEF SUMMARY OF THE INVENTION

Aspects of the disclosure relate to oligonucleotides and related methods for treating alcoholism in a subject. In some embodiments, potent RNAi oligonucleotides have been developed for selectively inhibiting ALDH2 expression in a subject. In some embodiments, the RNAi oligonucleotides are useful for reducing ALDH2 activity, and thereby decreasing alcohol tolerance and/or the desire to consume alcohol. In some embodiments, key regions of ALDH2 mRNA (referred to as hotspots) have been identified herein that are particularly amenable to targeting using such oligonucleotide-based approaches (See Example 1). In some embodiments, RNAi oligonucleotides provided herein incorporate modified phosphates, nicked tetraloop structures, and/or other modifications that improve activity, bioavailability and/or minimize the extent of enzymatic degradation after in vivo administration. In some embodiments, because the RNAi oligonucleotides provided herein can produce persistent reductions in ALDH2 activity, they overcome compliance issues associated with daily administration of existing small molecule inhibitors of ALDH2.

One aspect of the present disclosure provides oligonucleotides for reducing expression of ALDH2. In some embodiments, the oligonucleotides comprise an antisense strand comprising a sequence as set forth in any one of SEQ ID NOs: 591-600. In some embodiments, the oligonucleotides further comprise a sense strand that comprises a sequence as set forth in any one of SEQ ID NOs: 581-590. In some embodiments, the antisense strand consists of a sequence as set forth in any one of SEQ ID NOs: 591-600. In some embodiments, the sense strand consists of a sequence as set forth in any one of SEQ ID NOs: 581-590.

One aspect of the present disclosure provides oligonucleotides for reducing expression of ALDH2, in which the oligonucleotides comprise an antisense strand of 15 to 30 nucleotides in length. In some embodiments, the antisense strand has a region of complementarity to a target sequence of ALDH2 as set forth in any one of SEQ ID NOs: 601-607. In some embodiments, the region of complementarity is at least 15, at least 16, at least 17, at least 18, at least 19, at least 20, or at least 21 contiguous nucleotides in length. In some embodiments, the region of complementarity is fully complementary to the target sequence of ALDH2. In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the duplex region is at least 15, at least 16, at least 17, at least 18, at least 19, at least 20, or at least 21 nucleotides in length. In some embodiments, the region of complementarity to ALDH2 is at least 19 contiguous nucleotides in length. In some embodiments, the sense strand comprises a sequence as set forth in any one of SEQ ID NOs: 581-590. In some embodiments, the sense strand consists of a sequence as set forth in any one of SEQ ID NOs: 581-590. In some embodiments, the antisense strand comprises a sequence as set forth in any one of SEQ ID NOs: 591-600. In some embodiments, the antisense strand consists of a sequence as set forth in any one of SEQ ID NOs: 591-600. In some embodiments, the sense strand comprises at its 3'-end a stem-loop set forth as: S1-L-S2, in which S1 is complementary to S2, and in which L forms a loop between S1 and S2 of 3 to 5 nucleotides in length.

Another aspect of the present disclosure provides an oligonucleotide for reducing expression of ALDH2, the oligonucleotide comprising an antisense strand and a sense strand, in which the antisense strand is 21 to 27 nucleotides in length and has a region of complementarity to ALDH2, in which the sense strand comprises at its 3'-end a stem-loop set forth as: S1-L-S2, in which S1 is complementary to S2, and in which L forms a loop between S1 and S2 of 3 to 5 nucleotides in length, and in which the antisense strand and the sense strand form a duplex structure of at least 19 nucleotides in length but are not covalently linked. In some embodiments, the region of complementarity is fully complementary to at least 15, at least 16, at least 17, at least 18, at least 19, at least 20, or at least 21 contiguous nucleotides of ALDH2 mRNA. In some embodiments, L is a tetraloop. In some embodiments, L is 4 nucleotides in length. In some embodiments, L comprises a sequence set forth as GAAA. In some embodiments, the antisense strand is 27 nucleotides in length and the sense strand is 25 nucleotides in length. In some embodiments, the antisense strand and sense strand form a duplex region of 25 nucleotides in length.

In some embodiments, an oligonucleotide further comprises a 3'-overhang sequence on the antisense strand of two nucleotides in length. In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in a decreased ethanol tolerance in a subject. In some embodiments, the method results in a inhibition of ethanol intake by a subject. In some embodiments, the method results in a decreased desire of a subject to consume ethanol. In some embodiments, the subject to be treated suffers from alcoholism.

Another aspect of the present disclosure provides an oligonucleotide for reducing expression of ALDH2, the oligonucleotide comprising a sense strand of 15 to 40 nucleotides in length and an antisense strand of 15 to 30 nucleotides in length, in which the sense strand forms a duplex region with the antisense strand, in which the sense strand comprises a sequence as set forth in any one of SEQ ID NOs: 581-590 and results in a the antisense strand comprises a complementary sequence selected from SEQ ID NOs: 591-600.

In some embodiments, the oligonucleotide comprises a pair of sense and antisense strands selected from a row of the table set forth in Table 4.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

Figure 9:
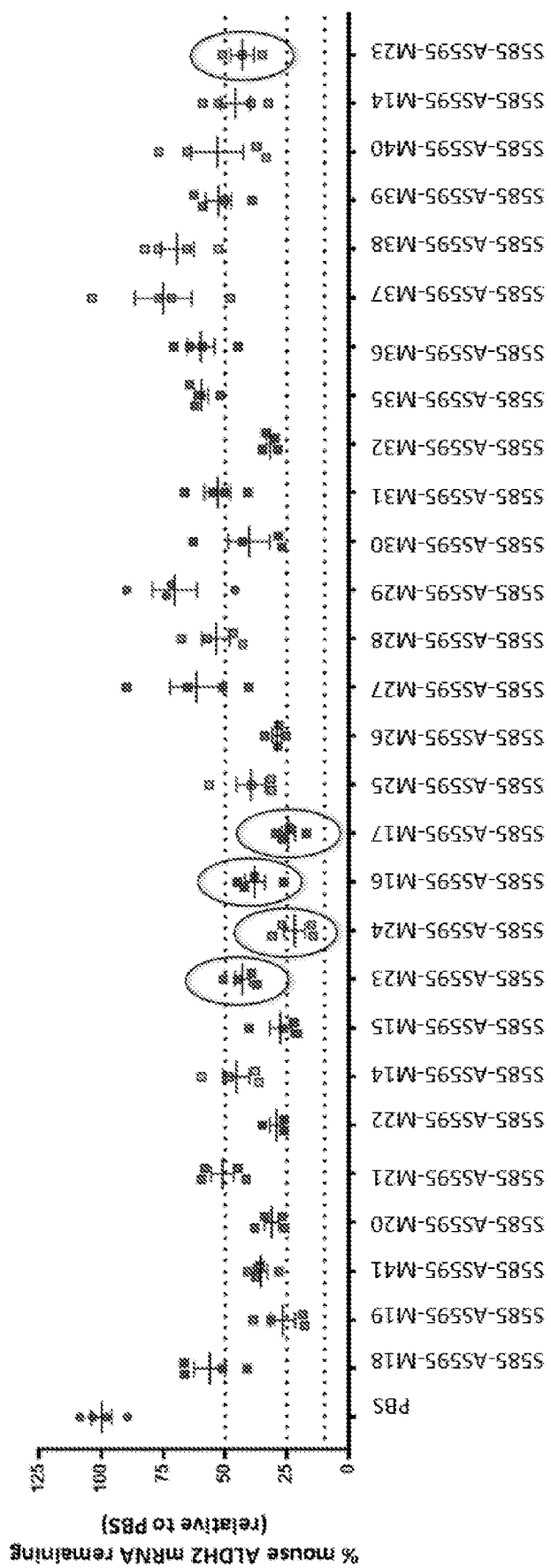

FIG. 9 is a graph showing the result of an in vivo assay screening GalNAc-conjugated ALDH2 oligonucleotides with different modification patterns to identify the modification pattern(s) that enhance the activity of the oligonucleotides in reducing ALDH2 mRNA level in mice.

Figure 10:
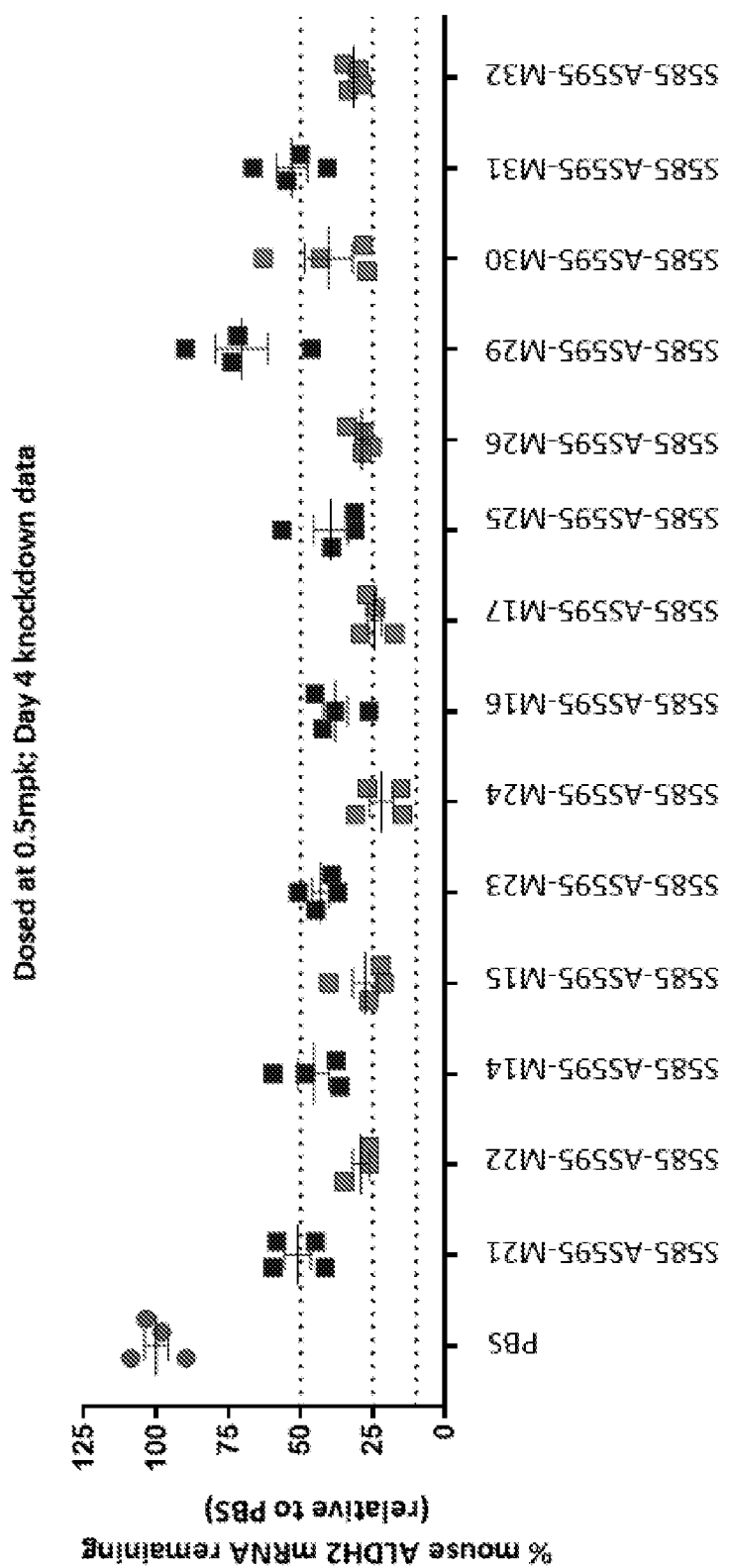

FIG. 10 a graph showing the comparison of the activities of GalNac-conjugated ALDH2 oligonucleotides with different modification patterns in reducing ALDH2 mRNA level in mice. Oligonucleotides were subcutaneously administered to mice at 0.5 mg/kg. The data was normalized to PBS control and showed the amount of ALDH2 mRNA remaining at day 4 following administration.

Figure 11:
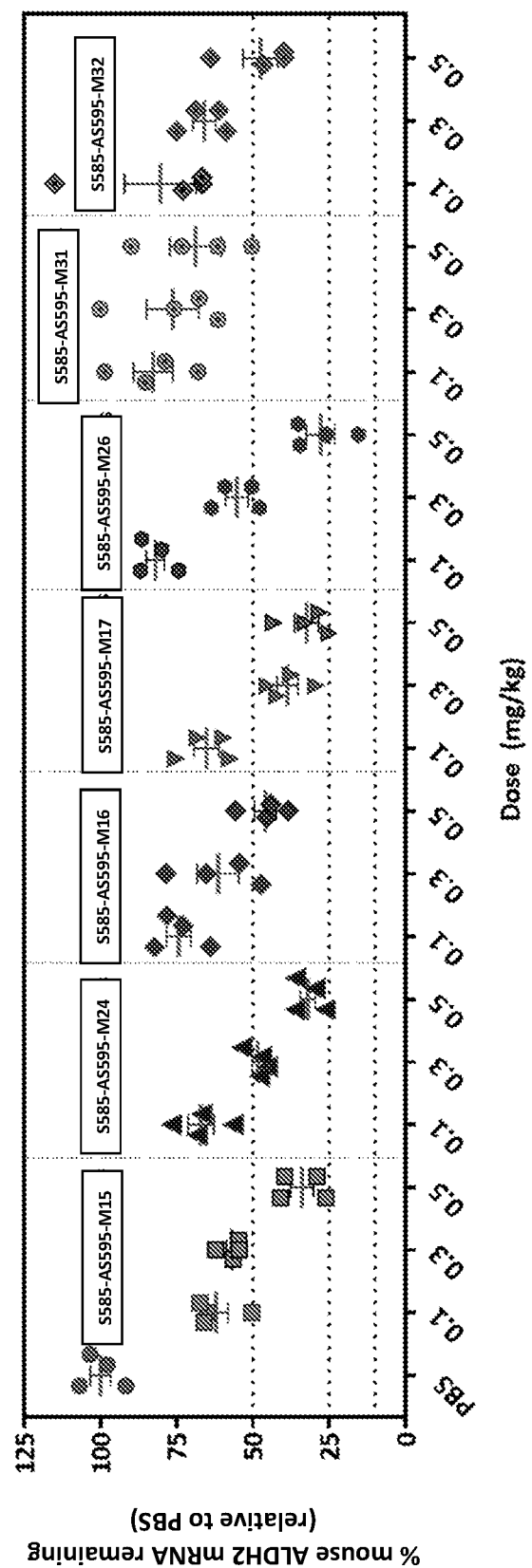

FIG. 11 is a graph showing the results of a dose titration study of the indicated GalNac-conjugated ALDH2 oligonucleotides in CD-1 mice. Oligonucleotides were subcutaneously administered to mice at 0.1, 0.3, or 0.5 mg/kg. The data was normalized to PBS control and showed the amount of ALDH2 mRNA remaining 72 hours after administration of the oligonucleotides.

Figure 12:
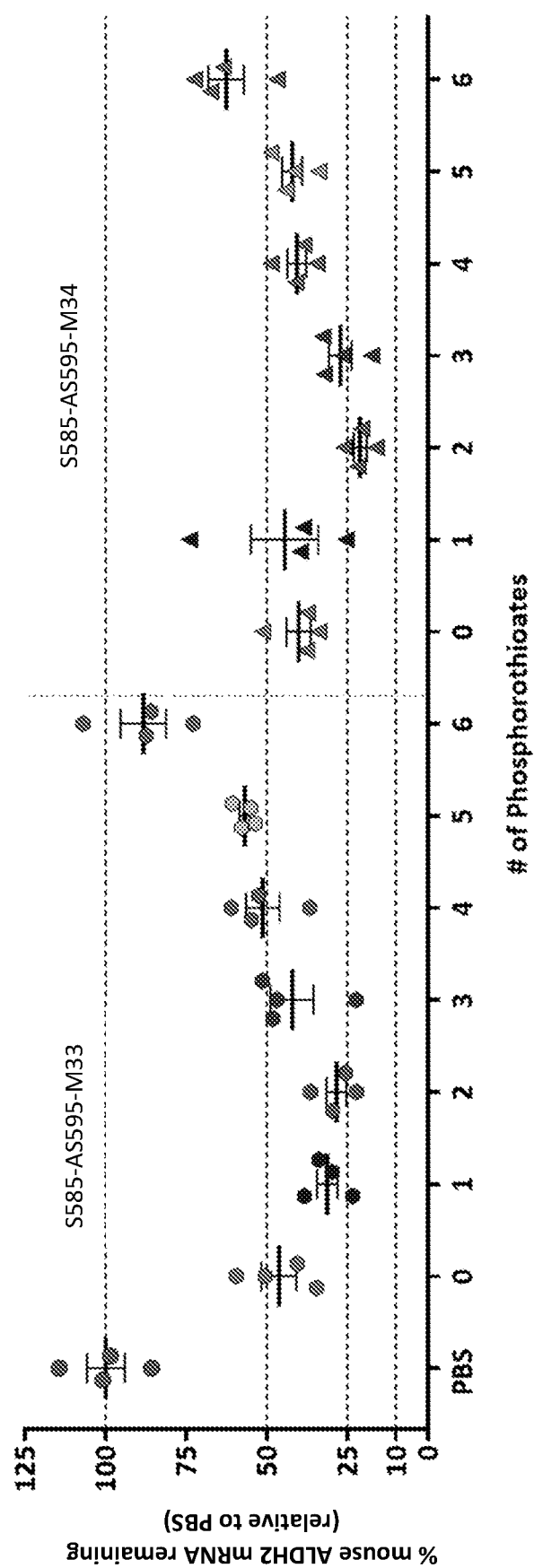

FIG. 12 is a graph showing the comparison of ALDH2 mRNA suppression activities of a GalNac-conjugated ALDH2 oligonucleotide with different modification patterns. Oligonucleotides were subcutaneously administered to mice at 0.5 mg/kg. The data was normalized to PBS control and showed the amount of ALDH2 mRNA remaining at day 4 following administration.

Figure 13:
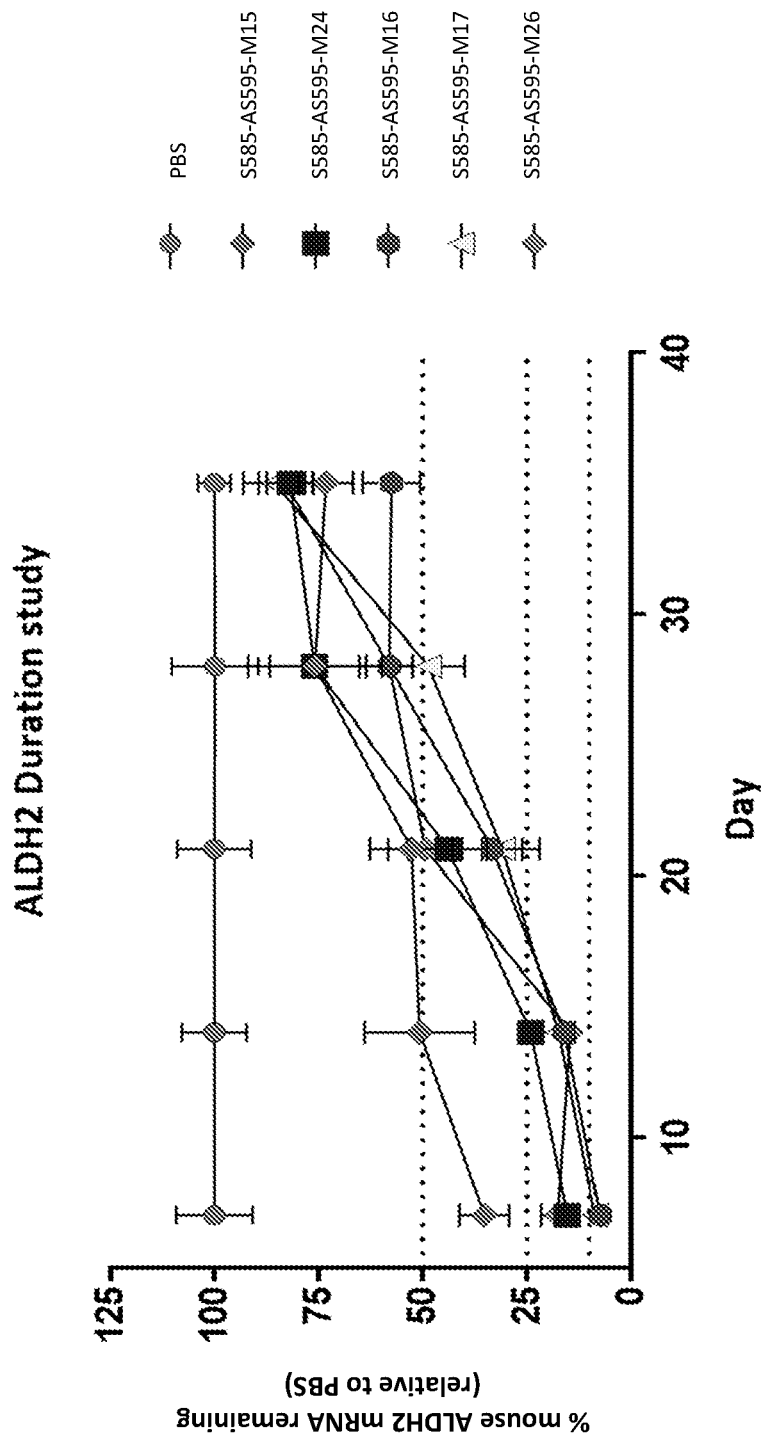

FIG. 13 is a graph showing the results of a duration study of the indicated GalNac-conjugated ALDH2 oligonucleotides in mice. Oligonucleotides were subcutaneously administered to mice at 3 mg/kg. The data was normalized to PBS control and showed the amount of ALDH2 mRNA remaining up to day 35 following administration.

DETAILED DESCRIPTION OF THE INVENTION

According to some aspects, the disclosure provides oligonucleotides targeting ALDH2 mRNA that are effective for reducing ALDH2 expression in cells, particularly liver cells (e.g., hepatocytes) for the treatment of alcoholism. Accordingly, in related aspects, the disclosure provided methods of treating alcoholism that involve selectively reducing ALDH2 gene expression in liver. In certain embodiments, ALDH2 targeting oligonucleotides provided herein are designed for delivery to selected cells of target tissues (e.g., liver hepatocytes) to treat alcoholism in a subject.

Further aspects of the disclosure, including a description of defined terms, are provided below.

I. Definitions

Alcoholism: As used herein, the term, "alcoholism" refers to repeated use of ethanol by an individual despite recurrent adverse consequences, which may or may not be combined with tolerance, withdrawal, and/or an uncontrollable drive to consume alcohol. Alcoholism may be classified as alcohol abuse, alcohol use disorder or alcohol dependence. A variety of approaches may be used to identify an individual suffering from alcoholism. For example, the World Health Organization has established the Alcohol Use Disorders Identification Test (AUDIT) as a tool for identifying potential alcohol misuse, including dependence and other similar tests have been developed, including the Michigan Alcohol Screening Test (MAST). Laboratory tests may be used to evaluate blood markers for detecting chronic use and/or relapse in alcohol drinking, including tests to detect levels of gamma-glutamyl transferase (GGT), mean corpuscular volume (red blood cell size), aspartate aminotransferase (AST), alanine aminotransferase (ALT), carbohydrate-deficient transferring (CDT), ethyl glucuronide (EtG), ethyl sulfate (EtS), and/or phosphatidylethanol (PEth). Animal models (e.g., mouse models) of alcoholism have been established (see, e.g., Rijk H, Crabbe J C, Rigter H. A mouse model of alcoholism. Physiol Behav. 1982 November; 29(5):833-9; Elizabeth Brandon-Warner, et al., Rodent Models of Alcoholic Liver Disease: Of Mice and Men. Alcohol. 2012 December; 46(8): 715-725; and Adeline Bertola, et al., Mouse model of chronic and binge ethanol feeding (the NIAAA model). Nature Protocols 8,627-637 (2013).)

ALDH2: As used herein, the term, "ALDH2" refers to the aldehyde dehydrogenase 2 family (mitochondrial) gene. ALDH2 encodes proteins that belong to the aldehyde dehydrogenase family of proteins and that function as the second enzyme of the oxidative pathway of alcohol metabolism that synthesizes acetate (acetic acid) from ethanol. Homologs of ALDH2 are conserved across a range of species, including human, mouse, rat, non-human primate species, and others (see, e.g., NCBI HomoloGene:55480.) ALDH2 also has homology with other aldehyde dehydrogenase encoding genes, including, for example, ALDH1A1. In humans, ALDH2 encodes at least two transcripts, namely NM_000690.3 (variant 1) and NM_001204889.1 (variant 2), each encoding a different isoform, NP_000681.2 (isoform 1) and NP_001191818.1 (isoform 2), respectively. Transcript variant 2 lacks an in-frame exon in the 5' coding region, compared to transcript variant 1, and encodes a shorter isoform (2), compared to isoform 1. Polymorphisms in ALDH2 have been identified (see, e.g., Chang J S, Hsiao J R, Chen C H. ALDH2 polymorphism and alcohol-related cancers in Asians: a public health perspective. J Biomed Sci. 2017 Mar. 3; 24(1):19. Review.)

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administering: As used herein, the terms "administering" or "administration" means to provide a substance (e.g., an oligonucleotide) to a subject in a manner that is pharmacologically useful (e.g., to treat a condition in the subject).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Complementary: As used herein, the term "complementary" refers to a structural relationship between nucleotides (e.g., two nucleotide on opposing nucleic acids or on opposing regions of a single nucleic acid strand) that permits the nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have nucleotide sequences that are complementary to each other so as to form regions of complementarity, as described herein.

Deoxyribonucleotide: As used herein, the term "deoxyribonucleotide" refers to a nucleotide having a hydrogen at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. In certain embodiments, a modified nucleotide comprises a 2'-O-methyl or a 2'-F substitution at the 2' position of the ribose ring.

Nicked Tetraloop Structure: A "nicked tetraloop structure" is a structure of a RNAi oligonucleotide characterized by the presence of separate sense (passenger) and antisense (guide) strands, in which the sense strand has a region of complementarity to the antisense strand such that the two strands form a duplex, and in which at least one of the strands, generally the sense strand, extends from the duplex in which the extension contains a tetraloop and two self-complementary sequences forming a stem region adjacent to the tetraloop, in which the tetraloop is configured to stabilize the adjacent stem region formed by the self-complementary sequences of the at least one strand.

Oligonucleotide: As used herein, the term "oligonucleotide" refers to a short nucleic acid, e.g., of less than 100 nucleotides in length. An oligonucleotide can comprise ribonucleotides, deoxyribonucleotides, and/or modified nucleotides including, for example, modified ribonucleotides. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, International Patent Application PCT/US2017/049909, filed on Sep. 1, 2017, U.S. Provisional Application Nos. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to ALDH2 mRNA sequence) may result in a decrease in the amount of RNA transcript, protein and/or enzymatic activity (e.g., encoded by the ALDH2 gene) compared to a cell that is not treated with the double-stranded oligonucleotide. Similarly, "reducing expression" as used herein refers to an act that results in reduced expression of a gene (e.g., ALDH2).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides (e.g., a target nucleotide sequence within an mRNA) to permit hybridization between the two sequences of nucleotides under appropriate hybridization conditions, e.g., in a phosphate buffer, in a cell, etc. A region of complementarity may be fully complementary to a nucleotide sequence (e.g., a target nucleotide sequence present within an mRNA or portion thereof). For example, a region of complementarity that is fully complementary to a nucleotide sequence present in an mRNA has a contiguous sequence of nucleotides that is complementary, without any mismatches or gaps, to a corresponding sequence in the mRNA. Alternatively, a region of complementarity may be partially complementary to a nucleotide sequence (e.g., a nucleotide sequence present in an mRNA or portion thereof). For example, a region of complementary that is partially complementary to a nucleotide sequence present in an mRNA has a contiguous sequence of nucleotides that is complementary to a corresponding sequence in the mRNA but that contains one or more mismatches or gaps (e.g., 1, 2, 3, or more mismatches or gaps) compared with the corresponding sequence in the mRNA, provided that the region of complementarity remains capable of hybridizing with the mRNA under appropriate hybridization conditions.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C. or at least 75° C. in 10 mM $NaHPO_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include but are not limited to non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors i. ALDH2 Targeting Oligonucleotides

Potent oligonucleotides have been identified herein through examination of the ALDH2 mRNA, including mRNAs of multiple different species (human, cynomolgus monkey, and mouse (see, e.g., Example 1)) and in vitro and in vivo testing. Such oligonucleotides can be used to achieve therapeutic benefit for alcoholic subjects by reducing ALDH2 activity, and consequently, by decreasing alcohol tolerance and/or the desire to consume alcohol. For example, potent RNAi oligonucleotides are provided herein that have a sense strand comprising, or consisting of, a sequence as set forth in any one of SEQ ID NO: 581-590 and an antisense strand comprising, or consisting of, a complementary sequence selected from SEQ ID NO: 591-600, as is also arranged the table provided in Table 4 (e.g., a sense strand comprising a sequence as set forth in SEQ ID NO: 581 and an antisense strand comprising a sequence as set forth in SEQ ID NO: 591).

The sequences can be put into multiple different oligonucleotide structures (or formats). For example, in some embodiments, the sequences can be incorporated into oligonucleotides that comprise sense and antisense strands that are both in the range of 17 to 36 nucleotides in length. In some embodiments, oligonucleotides incorporating such sequences are provided that have a tetraloop structure within a 3' extension of their sense strand, and two terminal overhang nucleotides at the 3' end of its antisense strand. In some embodiments, the two terminal overhang nucleotides are GG. Typically, one or both of the two terminal GG nucleotides of the antisense strand is or are not complementary to the target.

In some embodiments, oligonucleotides incorporating such sequences are provided that have sense and antisense strands that are both in the range of 21 to 23 nucleotides in length. In some embodiments, a 3' overhang is provided on the sense, antisense, or both sense and antisense strands that is 1 or 2 nucleotides in length. In some embodiments, an oligonucleotide has a guide strand of 23 nucleotides and a passenger strand of 21 nucleotides, in which the 3'-end of passenger strand and 5'-end of guide strand form a blunt end and where the guide strand has a two nucleotide 3' overhang.

In some embodiments, it has been discovered that certain regions of ALDH2 mRNA are hotspots for targeting because they are more amenable than other regions to oligonucleotide-based inhibition. In some embodiments, a hotspot region of ALDH2 comprises, or consists of, a sequence as set forth in any one of SEQ ID NOs:601-607. These regions of ALDH2 mRNA may be targeted using oligonucleotides as discussed herein for purposes of inhibiting ALDH2 mRNA expression.

Accordingly, in some embodiments, oligonucleotides provided herein are designed so as to have regions of complementarity to ALDH2 mRNA (e.g., within a hotspot of ALDH2 mRNA) for purposes of targeting the mRNA in cells and inhibiting its expression. The region of complementarity is generally of a suitable length and base content to enable annealing of the oligonucleotide (or a strand thereof) to ALDH2 mRNA for purposes of inhibiting its expression.

In some embodiments, an oligonucleotide disclosed herein comprises a region of complementarity (e.g., on an antisense strand of a double-stranded oligonucleotide) that is at least partially complementary to a sequence as set forth in SEQ ID NOs: 1-14 and 17-290, which include sequences mapping to within hotspot regions of ALDH2 mRNA. In some embodiments, an oligonucleotide disclosed herein comprises a region of complementarity (e.g., on an antisense strand of a double-stranded oligonucleotide) that is fully complementary to a sequence as set forth in SEQ ID NOs: 1-14 and 17-290. In some embodiments, a region of complementarity of an oligonucleotide that is complementary to contiguous nucleotides of a sequence as set forth in SEQ ID NOs: 1-14 and 17-290 spans the entire length of an antisense strand. In some embodiments, a region of complementarity of an oligonucleotide that is complementary to contiguous nucleotides of a sequence as set forth in any one of SEQ ID NOs: 1-14 and 17-290 spans a portion of the entire length of an antisense strand (e.g., all but two nucleotides at the 3' end of the antisense strand). In some embodiments, an oligonucleotide disclosed herein comprises a region of complementarity (e.g., on an antisense strand of a double-stranded oligonucleotide) that is at least partially (e.g., fully) complementary to a contiguous stretch of nucleotides spanning nucleotides 1-19 of a sequence as set forth in SEQ ID NOs: 581-590.

In some embodiments, the region of complementarity is at least 12, at least 13, at least 14, at least 15, at least 16, at least 17, at least 18, at least 19, at least 20, at least 21, at least 22, at least 23, at least 24, at least 25 nucleotides in length. In some embodiments, an oligonucleotide provided herein has a region of complementarity to ALDH2 that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to ALDH2 that is 12, 13, 14, 15, 16, 17, 18, 19, 20, 21, 22, 23, 24, 25, 26, 27, 28, 29 or 30 nucleotides in length.

In some embodiments, a region of complementarity to ALDH2 may have one or more mismatches compared with a corresponding sequence of ALDH2 mRNA. A region of complementarity on an oligonucleotide may have up to 1, up to 2, up to 3, up to 4, up to 5, etc. mismatches provided that it maintains the ability to form complementary base pairs with ALDH2 mRNA under appropriate hybridization conditions. Alternatively, a region of complementarity on an oligonucleotide may have no more than 1, no more than 2, no more than 3, no more than 4, or no more than 5 mismatches provided that it maintains the ability to form complementary base pairs with ALDH2 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with ALDH2 mRNA under appropriate hybridization conditions.

Still, in some embodiments, double-stranded oligonucleotides provided herein comprise, of consist of, a sense strand having a sequence as set forth in any one of SEQ ID NO: 1-14 and 17-290 and an antisense strand comprising a complementary sequence selected from SEQ ID NO: 291-304 and 307-580, as is arranged in the table provided in Table 4 (e.g., a sense strand comprising a sequence as set forth in SEQ ID NO: 1 and an antisense strand comprising a sequence as set forth in SEQ ID NO: 291).

ii. Oligonucleotide Structures

There are a variety of structures of oligonucleotides that are useful for targeting ALDH2 in the methods of the present disclosure, including RNAi, miRNA, etc. Any of the structures described herein or elsewhere may be used as a framework to incorporate or target a sequence described herein (e.g., a hotpot sequence of ALDH2 such as those illustrated in SEQ ID NOs: 601-607). Double-stranded oligonucleotides for targeting ALDH2 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, double-stranded oligonucleotides for reducing the expression of ALDH2 expression engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, oligonucleotides may be in the range of 21 to 23 nucleotides in length. In some embodiments, oligonucleotides may have an overhang (e.g., of 1, 2, or 3 nucleotides in length) in the 3' end of the sense and/or antisense strands. In some embodiments, oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. See, for example, U.S. Pat. Nos. 9,012,138, 9,012,621, and 9,193,753, the contents of each of which are incorporated herein for their relevant disclosures.

In some embodiments, an oligonucleotide of the invention has a 36 nucleotide sense strand that comprises an region extending beyond the antisense-sense duplex, where the extension region has a stem-tetraloop structure where the stem is a six base pair duplex and where the tetraloop has four nucleotides. In certain of those embodiments, three or four of the tetraloop nucleotides are each conjugated to a monovalent GalNac ligand.

In some embodiments, an oligonucleotide of the invention comprises a 25 nucleotide sense strand and a 27 nucleotide antisense strand that when acted upon by a dicer enzyme results in an antisense strand that is incorporated into the mature RISC.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of ALDH2 are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, an oligonucleotide disclosed herein for targeting ALDH2 comprises an antisense strand comprising or consisting of a sequence as set forth in any one of SEQ ID NOs: 291-304, 307-580, and 591-600. In some embodiments, an oligonucleotide comprises an antisense strand comprising or consisting of at least 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 291-304, 307-580, and 591-600.

In some embodiments, a double-stranded oligonucleotide may have an antisense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least 12 nucleotides in length (e.g., at least 12, at least 15, at least 19, at least 21, at least 25, at least 27, at least 30, at least 35, or at least 38 nucleotides in length). In some embodiments, an oligonucleotide may have an antisense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide disclosed herein for targeting ALDH2 comprises or consists of a sense strand sequence as set forth in in any one of SEQ ID NOs: 1-14, 17-290, and 581-590. In some embodiments, an oligonucleotide has a sense strand that comprises or consists of at least 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 1-14, 17-290, and 581-590.

In some embodiments, an oligonucleotide may have a sense strand (or passenger strand) of up to 40 nucleotides in length (e.g., up to 40, up to 35, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 35, or at least 38 nucleotides in length). In some embodiments, an oligonucleotide may have a sense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, a sense strand comprises a stem-loop structure at its 3'-end. In some embodiments, a sense strand comprises a stem-loop structure at its 5'-end. In some embodiments, a stem is a duplex of 2, 3, 4, 5, 6, 7, 8, 9, 10, 11, 12, 13, or 14 nucleotides in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide provided herein comprises sense and antisense strands, such that there is a 3'-overhang on either the sense strand or the antisense strand, or both the sense and antisense strand. In some embodiments, oligonucleotides provided herein have one 5'end that is thermodynamically less stable compared to the other 5' end. In some embodiments, an asymmetric oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7 or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary to the target. In some embodiments, the last one or two nucleotides at the 3' end of the antisense strand are not complementary to the target. In some embodiments, the 5' end and/or the 3' end of a sense or antisense strand has an inverted cap nucleotide.

e. Mismatches

In some embodiments, there is one or more (e.g., 1, 2, 3, 4, 5) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

iii. Single-Stranded Oligonucleotides

In some embodiments, an oligonucleotide for reducing ALDH2 expression as described herein is single-stranded. Such structures may include, but are not limited to single-stranded RNAi oligonucleotides. Recent efforts have demonstrated the activity of single-stranded RNAi oligonucleotides (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier (e.g., "naked delivery"), it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every sugar is modified at the 2'-position. These modifications may be reversible or irreversible. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. In certain embodiments, the 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro, 2'-O-methyl, or 2'-O-methoxyethyl. However, a large variety of 2' position modifications that have been developed for use in oligonucleotides can be employed in oligonucleotides disclosed herein. See, e.g., Bramsen et al., Nucleic Acids Res., 2009, 37, 2867-2881. In some embodiments, a modification in a sugar comprises a modification of the sugar ring, which may comprise modification of one or more carbons of the sugar ring. For example, a modification of a sugar of a nucleotide may comprise a linkage between the 2'-carbon and a 1'-carbon or 4'-carbon of the sugar. For example, the linkage may comprise an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

5'-terminal phosphate groups of oligonucleotides may or in some circumstances enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, International Patent Application PCT/US2017/049909, filed on Sep. 1, 2017, U.S. Provisional Application Nos. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—CH$_2$—PO(OH)$_2$ or —O—CH$_2$—PO(OR)$_2$, in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$, or a protecting group. In certain embodiments, the alkyl group is CH$_2$CH$_3$. More typically, R is independently selected from H, CH$_3$, or CH$_2$CH$_3$.

c. Modified Internucleoside Linkages

In some embodiments, the oligonucleotide may comprise a modified internucleoside linkage. In some embodiments, phosphate modifications or substitutions may result in an oligonucleotide that comprises at least one (e.g., at least 1, at least 2, at least 3 or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base Modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower T$_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher T$_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., *Nature Biotechnology*, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. *J. Am. Chem. Soc.* 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., International Patent Application PCT/US2017/048239 and U.S. Prov. Appl. No. 62/378,635, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand, as described, for example, in International Patent Application Publication WO 2016/100401, which was published on Jun. 23, 2016, the relevant contents of which are incorporated herein by reference.

In some embodiments, it is desirable to target an oligonucleotide that reduces the expression of ALDH2 to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable. In some embodiments, a duplex extension (up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of ALDH2. Such compositions can be suitably formulated such that when administered to a subject, either into the immediate environment of a target cell or systemically, a sufficient portion of the oligonucleotides enter the cell to reduce ALDH2 expression. Any of a variety of suitable oligonucleotide formulations can be used to deliver oligonucleotides for the reduction of ALDH2 as disclosed herein. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS)

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Typically. the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing ALDH2 expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing ALDH2 Expression in Cells

In some embodiments, methods are provided for delivering to a cell an effective amount any one of oligonucleotides disclosed herein for purposes of reducing expression of ALDH2 in the cell. Methods provided herein are useful in any appropriate cell type. In some embodiments, a cell is any cell that expresses ALDH2 (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of ALDH2 solely in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of ALDH2 expression (e.g., RNA, protein). In some embodiments, the extent to which an oligonucleotide provided herein reduces levels of expression of ALDH2 is evaluated by comparing expression levels (e.g., mRNA or protein levels of ALDH2 to an appropriate control (e.g., a level of ALDH2 expression in a cell or population of cells to which an oligonucleotide has not been delivered or to which a negative control has been delivered). In some embodiments, an appropriate control level of ALDH2 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of ALDH2 expression in a cell. In some embodiments, the reduction in levels of ALDH2 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of ALDH2. The appropriate control level may be a level of ALDH2 expression in a cell or population of cells that has not been contacted with an oligonucleotide as described herein. In some embodiments, the effect of delivery of an oligonucleotide to a cell according to a method disclosed herein is assessed after a finite period of time. For example, levels of ALDH2 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing ALDH2 expression for the treatment of alcoholism in a subject. In some embodiments, the methods may comprise administering to a subject in need thereof an effective amount of any one of the oligonucleotides disclosed herein. Such treatments could be used, for example, to decrease ethanol tolerance in a subject, thereby inhibiting ethanol intake by the subject (e.g., by decreasing the desire of the subject to consume ethanol). The present disclosure provides for both prophylactic and therapeutic methods of treating a subject at risk of (or susceptible to) alcoholism and/or a disease or disorder associated with alcoholism.

In certain aspects, the disclosure provides a method for preventing in a subject, a disease or disorder as described herein by administering to the subject a therapeutic agent (e.g., an oligonucleotide or vector or transgene encoding same). In some embodiments, the subject to be treated is a subject who will benefit therapeutically from a reduction in the amount of ALDH2 protein, e.g., in the liver.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intramuscular injection), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

In some embodiments, oligonucleotides are administered at a dose in a range of 0.1 mg/kg to 25 mg/kg (e.g., 1 mg/kg to 5 mg/kg). In some embodiments, oligonucleotides are administered at a dose in a range of 0.1 mg/kg to 5 mg/kg or in a range of 0.5 mg/kg to 5 mg/kg.

As a non-limiting set of examples, the oligonucleotides of the instant disclosure would typically be administered once per year, twice per year, quarterly (once every three months), bi-monthly (once every two months), monthly, or weekly.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Figure 1:
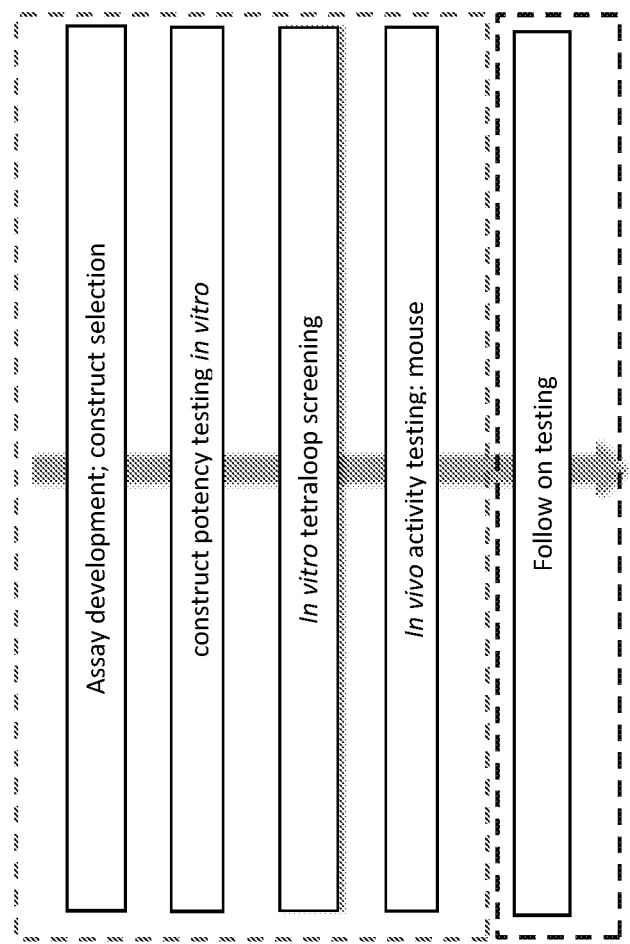
FIG. 1 is a flowchart depicting the experimental design used to select compounds for testing in cell and animal models and to develop double-stranded oligonucleotides for reducing expression of ALDH2.

Example 1: Development of ALDH2 Oligonucleotide Inhibitors Using Human and Mouse Cell-Based Assays FIG. 1 shows a workflow using human and mouse-based assays to develop candidate oligonucleotides for inhibition of ALDH2 expression. First, a computer-based algorithm was used to generate candidate oligonucleotide sequences (25-27-mer) for ALDH2 inhibition. Cell-based assays and PCR assays were then employed for evaluation of candidate oligonucleotides for their ability to reduce ALDH2 expression.

The computer-based algorithm provided oligonucleotides that were complementary to the human ALDH2 mRNA (SEQ ID NO: 608, Table 1), of which certain sequences were also complementary to the cynomolgus monkey ALDH2 mRNA (SEQ ID NO:609, Table 1) and/or the mouse ALDH2 mRNA (SEQ ID NO: 610, Table 1).

TABLE 1

Sequences of human, cynomolgus monkey and mouse ALDH2 mRNA

| Species | GenBank RefSeq # | SEQ ID NO. |
| --- | --- | --- |
| Human | NM_000690.3 | 608 |
| Cynomolgus Monkey | XM_005572278.2 | 609 |
| Mouse | NM_009656.4 | 610 |

Figure 2:
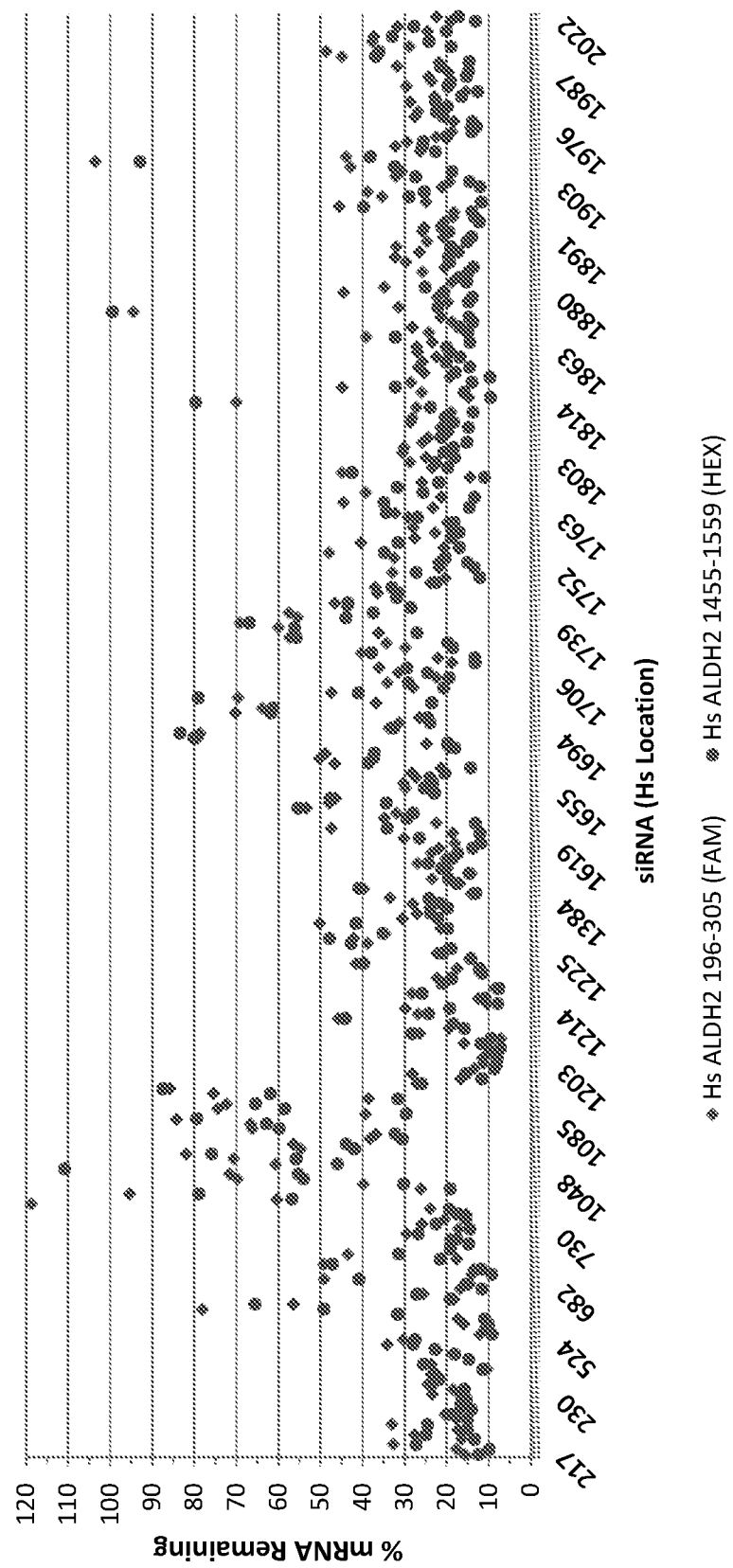
FIG. 2 is a graph showing the percent of ALDH2 mRNA remaining after a screen of 288 ALDH2 oligonucleotides in HepG2 cells. The nucleotide position in NM_000690.3 that corresponds to the 3' end of the sense strand of each siRNA is indicated on the x-axis.
Figure 3A:
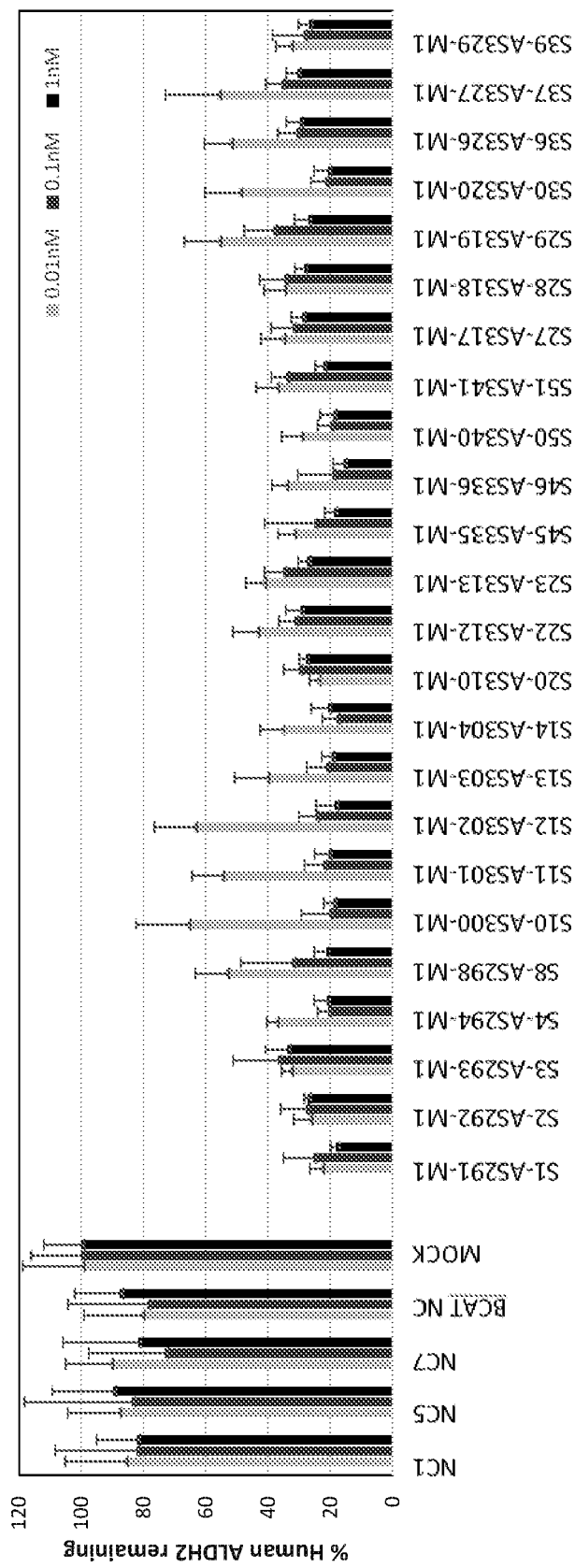
FIGS. 3A-3D are a set of graphs showing the percentage of mRNA remaining after ALDH2 oligonucleotide screening of 96 ALDH2 oligonucleotides at three different concentrations (1 nM, 0.1 nM and 0.01 nM) in HepG2 cells.
Figure 3B:
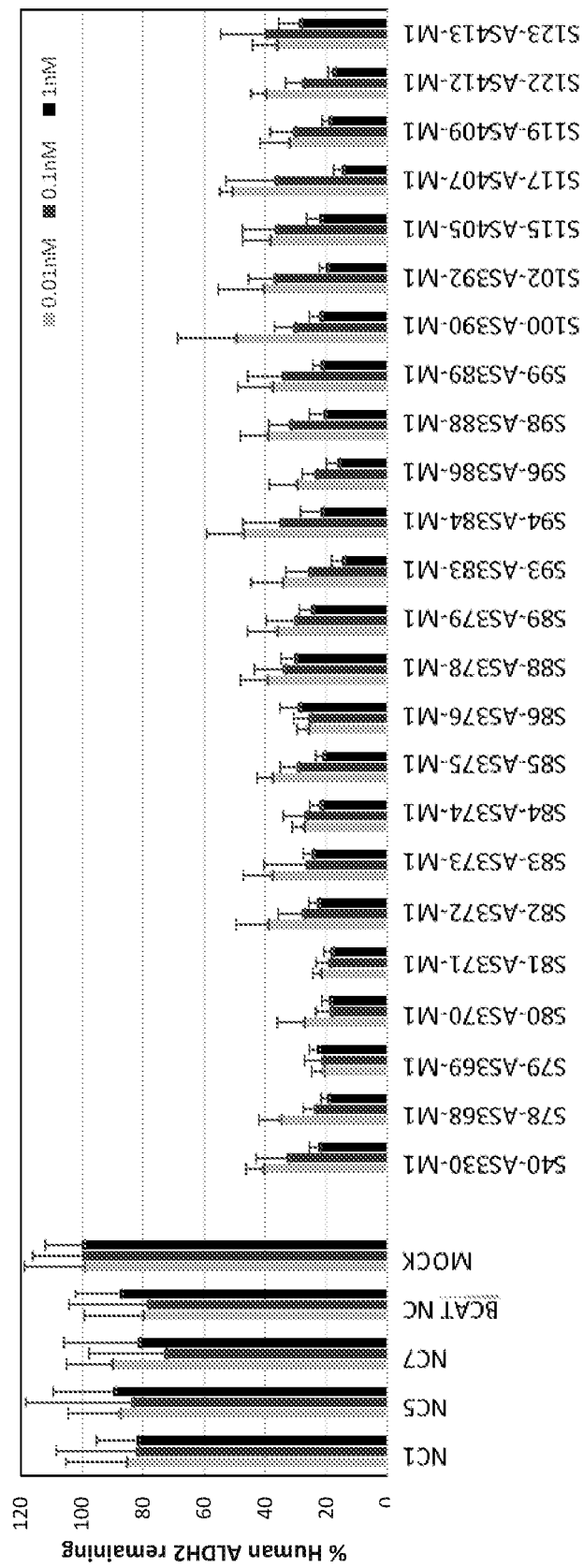
Figure 3C:
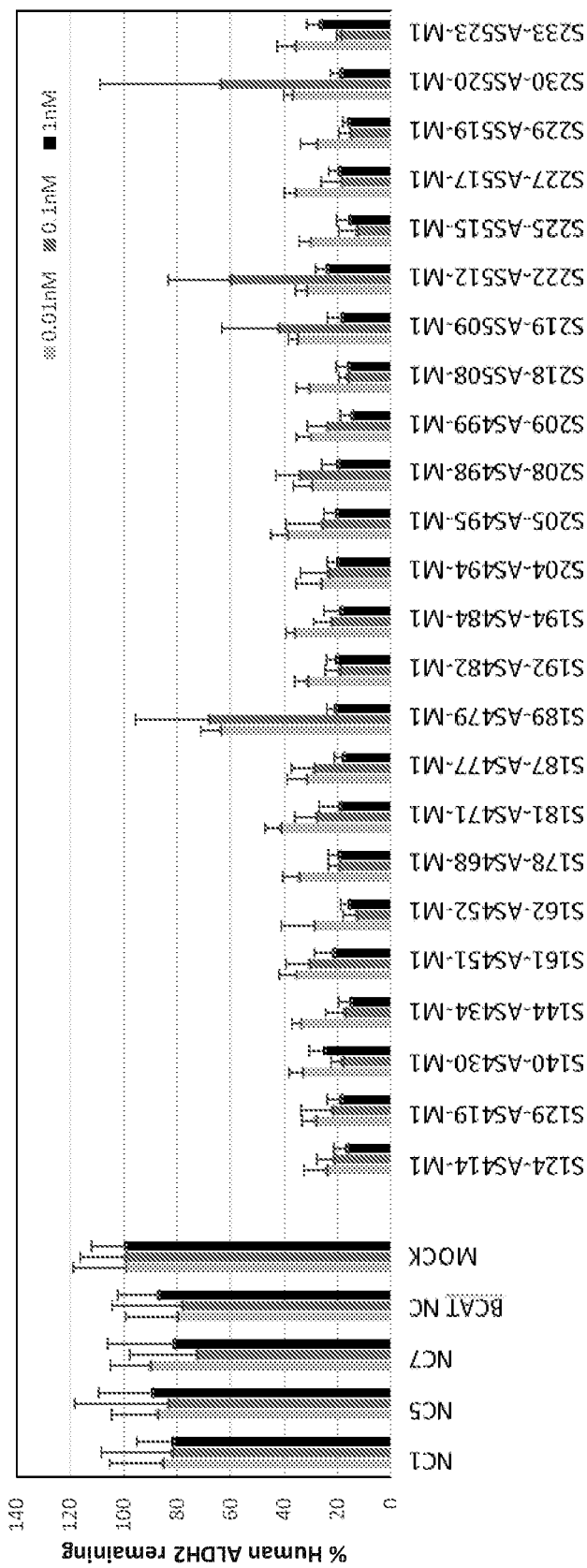
Figure 3D:
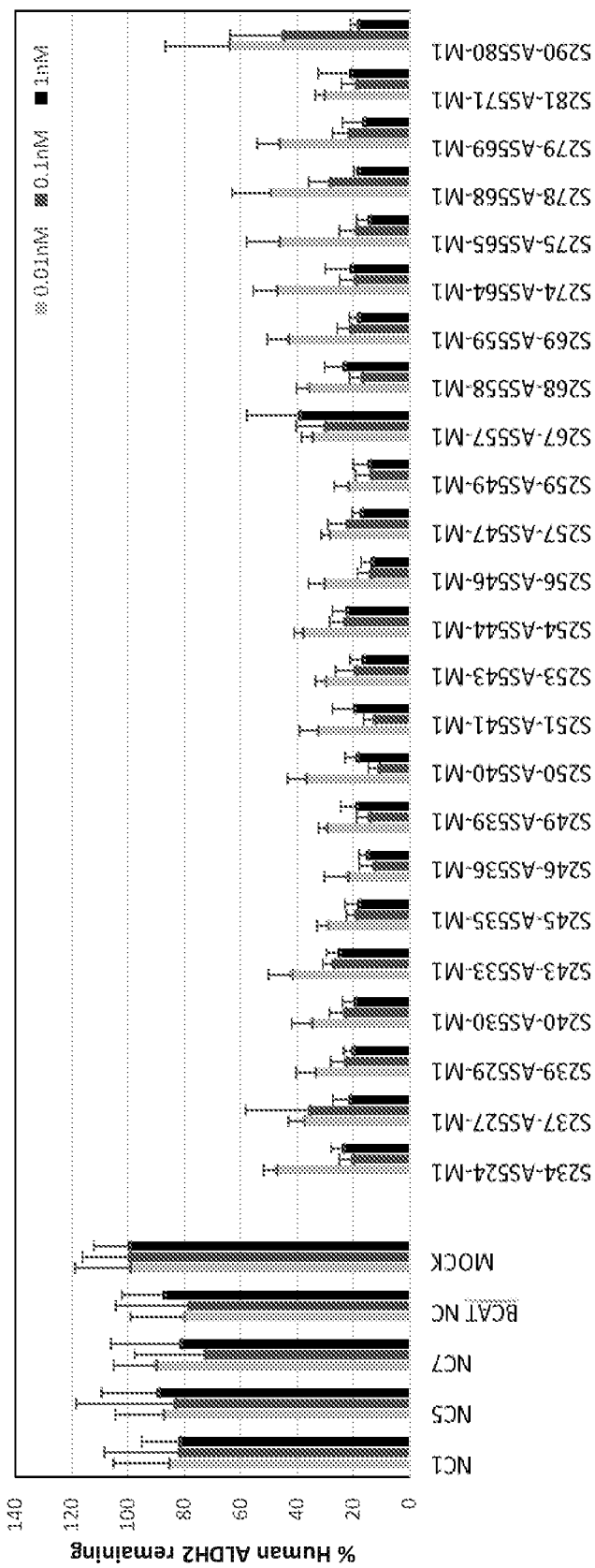

Of the oligonucleotides that the algorithm provided, 288 oligonucleotides were selected as candidates for experimental evaluation in a HepG2 cell-based assay. In this assay, HepG2, human hepatoma cells expressing ALDH2 were transfected with the oligonucleotides. Cells were maintained for a period of time following transfection and then levels of remaining ALDH2 mRNA were interrogated using TAQMAN®-based qPCR assays. Two qPCR assays, a 3' assay and a 5' assay, were used to determine mRNA levels as measured by HEX and FAM probes, respectively. The results of the HepG2 cell-based assay with the 288 oligonucleotides are shown in FIG. 2. The percent mRNA remaining is shown for each of the 3' assay (circle shapes) and the 5' assay (diamond shapes). Oligonucleotides resulting in less than or equal to 25% mRNA remaining compared to negative controls were considered hits. Oligonucleotides with low complementarity to the human genome were used as negative controls.

Based on the activity and locations of these oligonucleotides, hotspots on the human ALDH2 mRNA were defined. A hotspot was identified as a stretch on the human ALDH2 mRNA sequence associated with at least one oligonucleotide resulting in mRNA levels that were less than or equal to 25% in either assay compared with controls. Accordingly, the following hotspots within the human ALDH2 mRNA sequence were identified: 181-273; 445-539; 646-696; 691-749; 1165-1235; 1770-1821; and 1824-1916.

The sequences of the hotspots are outlined in Table 2.

TABLE 2

Sequences of Hotspots

| Hotspot Position In Human ALDH2 mRNA | Sequence | SEQ ID NO. |
| --- | --- | --- |
| 181-273 | AACCAGCAGCCCGAGGTCTTCTG CAACCAGATTTTCATAAACAATG AATGGCACGATGCCGTCAGCAGG AAAACATTCCCCACCGTCAATCC G | 601 |
| 445-539 | ACCTACCTGGCGGCCTTGGAGAC CCTGGACAATGGCAAGCCCTATG TCATCTCCTACCTGGTGGATTTG GACATGGTCCTCAAATGT CTCCGGTATTATGC | 602 |

TABLE 2-continued

Sequences of Hotspots

| Hotspot Position In Human ALDH2 mRNA | Sequence | SEQ ID NO. |
| --- | --- | --- |
| 646-696 | CCGTGGAATTTCCCGCTCCTGA TGCAAGCATGGAAGCTGGGCCC AGCCTTG | 603 |
| 691-749 | GCCTTGGCAACTGGAAACGTGG TTGTGATGAAGGTAGCTGAGCA GACACCCCTCACCGC | 604 |
| 1165-1235 | GAGCAGGGGCCGCAGGTGGATG AAACTCAGTTTAAGAAGATCCT CGGCTACATCAACACGGGGAAG CAAGA | 605 |
| 1770-1821 | TCTCTTGGGTCAAGAAAGTTCT AGAATTTGAATTGATAAACATG GTGGGTTG | 606 |
| 1824-1916 | TGAGGGTAAGAGTATATGAGGA ACCTTTTAAACGACAACAATAC TGCTAGCTTTCAGGATGATTTT TAAAAAATAGATTCAAATGTG TTATCC | 607 |

Dose Response Analysis

Of the 288 oligonucleotides evaluated in the initial HepG2 cell-based assay, 96 particularly active oligonucleotides were selected as hits based on their ability to knock down ALDH2 levels and were subjected to a secondary screen.

In this secondary screen, the candidate oligonucleotides were tested using the same assay as in the primary screen, but at three different concentrations (1 nM, 0.1 nM and 0.01 nM) (FIGS. 3A-3D). The target mRNA levels were normalized based on splicing factor, arginine/serine-rich 9 (SFRS9), a housekeeping gene that provides a stable expression reference across samples, to generate the percent mRNA shown in FIGS. 3A-3D. The tested oligonucleotides in each of FIGS. 3A-3D are shown compared to negative control sequences (NC1, NC5, NC7, BCAT NC) and mock transfection. All 96 oligonucleotides had the same modification pattern, designated M1, which contains a combination of ribonucleotides, deoxyribonucleotides and 2'-O-methyl modified nucleotides. The sequences of the 96 oligonucleotides tested are provided in Table 3 (data for SEQ ID NOs. 15-16 and 305-306 not shown in FIGS. 3A-3D).

TABLE 3

Candidate oligonucleotide Sequences for HepG2 Cell-Based Assay

| Hs | Cm | Mm | Sense SEQ ID NO. | Corresponding Antisense SEQ ID NO. |
| --- | --- | --- | --- | --- |
| X | X | X | 20, 27-30, 36, 37, 39-40, 78-86, 88-89, 93-94, 96, 98-100, 102 | 310, 317-320, 326, 327, 329-330, 368-376, 378-379, 383-384, 386, 388-390, 392 |
| X | X |  | 45-46, 50-51, 115, 117, 119, 122-124, 161, 178, 181, 187, 189, 204-205, 208-209, 237, 239-240, 290 | 335-336, 340-341, 405, 407, 409, 412-414, 451, 468, 471, 477, 479, 494-495, 498-499, 527, 529-530, 580 |
| X |  | X | 1-2, 22-23 | 291-292, 312-313 |

TABLE 3-continued

Candidate oligonucleotide Sequences for HepG2 Cell-Based Assay

| Hs | Cm | Mm | Sense SEQ ID NO. | Corresponding Antisense SEQ ID NO. |
|---|---|---|---|---|
| X | | | 3-4, 8, 10-14, 129, 140, 144, 162, 192, 194, 218-219, 222, 225, 227, 229-230, 233-234, 243, 245-246, 249-251, 253-254, 256-257, 259, 267-269, 274-275, 278-279, 281 | 293-294, 298, 300-304, 419, 430, 434, 452, 482, 484, 508-509, 512, 515, 517, 519-520, 523-524, 533, 535-536, 539-541, 543-544, 546-547, 549, 557-559, 564-565, 568-569, 571 |

Hs: human, Cm: cynomolgus monkey, and Mm: mouse; the sense and antisense SEQ ID NO. columns provide the sense strand and respective antisense strand, in relative order, that are hybridized to make each oligonucleotide. For example, sense strand of SEQ ID NO: 1 hybridizes with antisense strand of SEQ ID NO: 291, and the sense strand of SEQ ID NO: 2 hybridizes with the antisense strand of SEQ ID NO: 293; each of the oligonucleotides tested had the same modification pattern.

Figure 4:
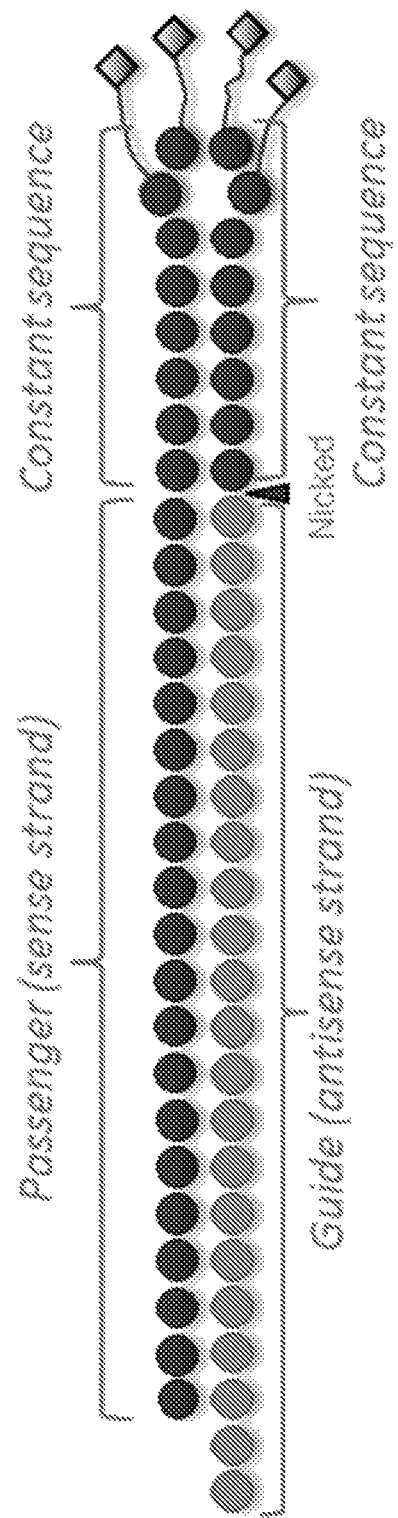
FIG. 4 is a schematic showing a non-limiting example of a double-stranded oligonucleotide with a nicked tetraloop structure that has been conjugated to four GalNAc moieties (diamond shapes).
Figure 5A:
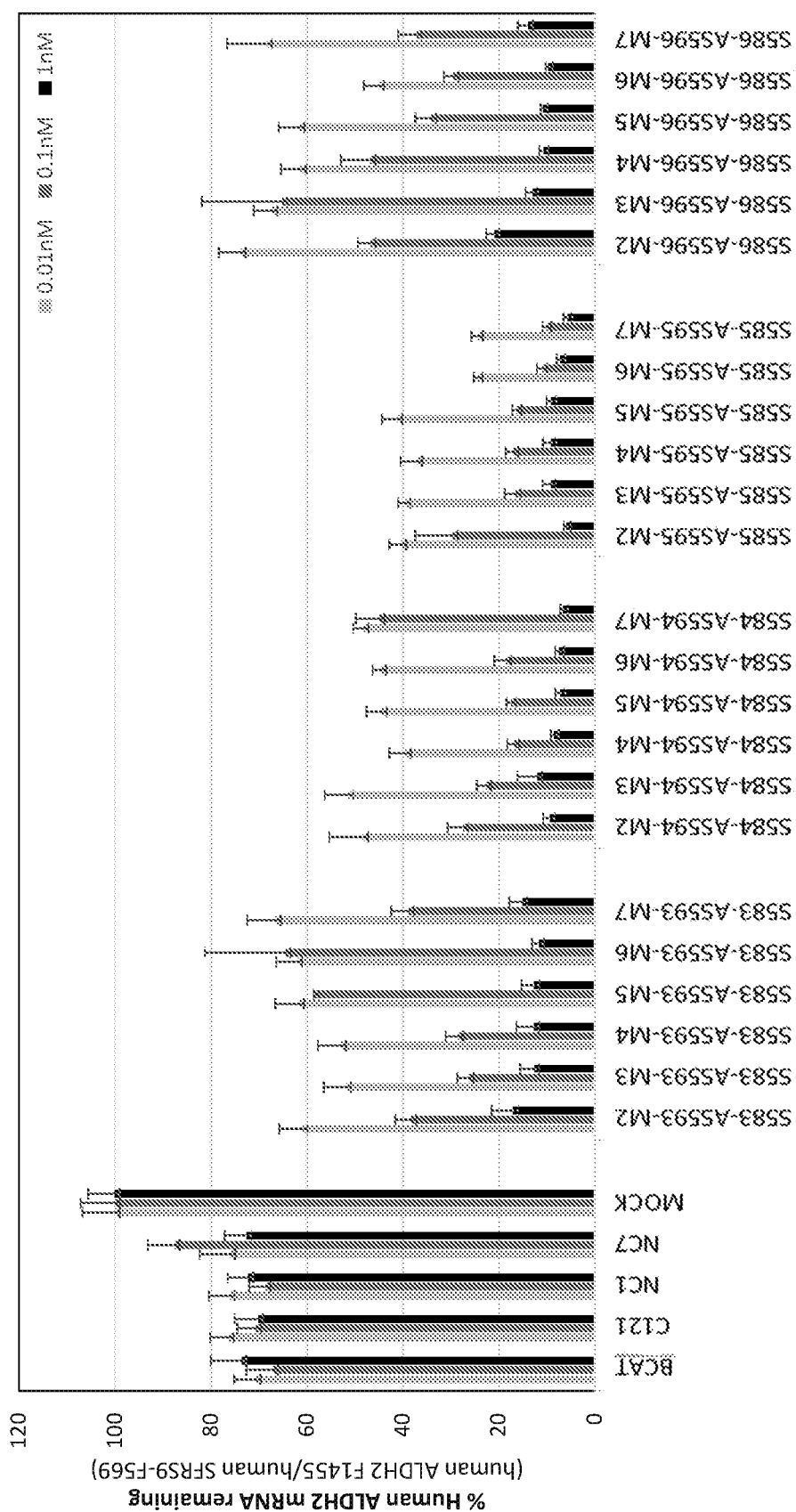
FIGS. 5A-5B are a set of graphs showing the results of screening in HepG2 cells using ALDH2 oligonucleotides of different base sequences in the nicked tetraloop structure, adapted to different modification patterns, and at three different concentrations (1 nM, 0.1 nM and 0.01 nM).
Figure 5B:
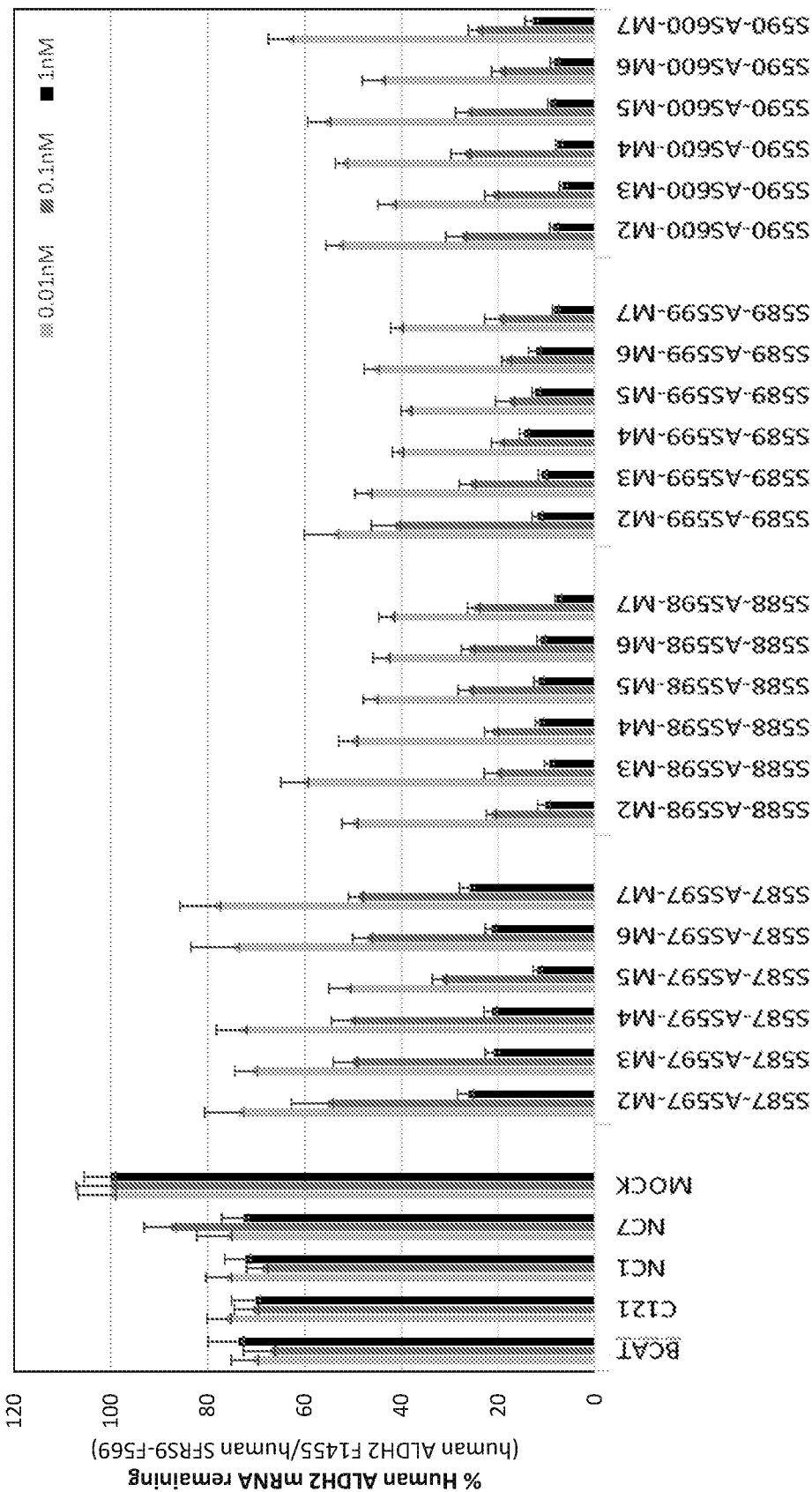

At this stage, eight best performing oligonucleotides from the testing were selected for further testing. The selected oligonucleotides were converted to nicked tetraloop structure formats (a 36-mer passenger strand with a 22-mer guide strand). See FIG. 4 for a generic tetraloop structure. These oligonucleotides were then tested as before, evaluating each oligonucleotide at three concentrations for its ability to reduce ALDH2 mRNA expression in HepG2 cells. FIGS. 5A-5B show data for oligonucleotides made from different base sequences with nicked tetraloop structures, each adapted to six different modification patterns. The target mRNA levels were normalized as described above to generate the percent mRNA shown in FIGS. 5A-5B, and the tested oligonucleotides in each of FIGS. 5A-5B are shown compared to negative control sequences (BCAT, C121, NC1, NC7) and mock transfection. Data for SEQ ID NOs: 581-582 and SEQ ID NOs: 591-592 are not shown in FIGS. 5A-5B.

Figure 6:
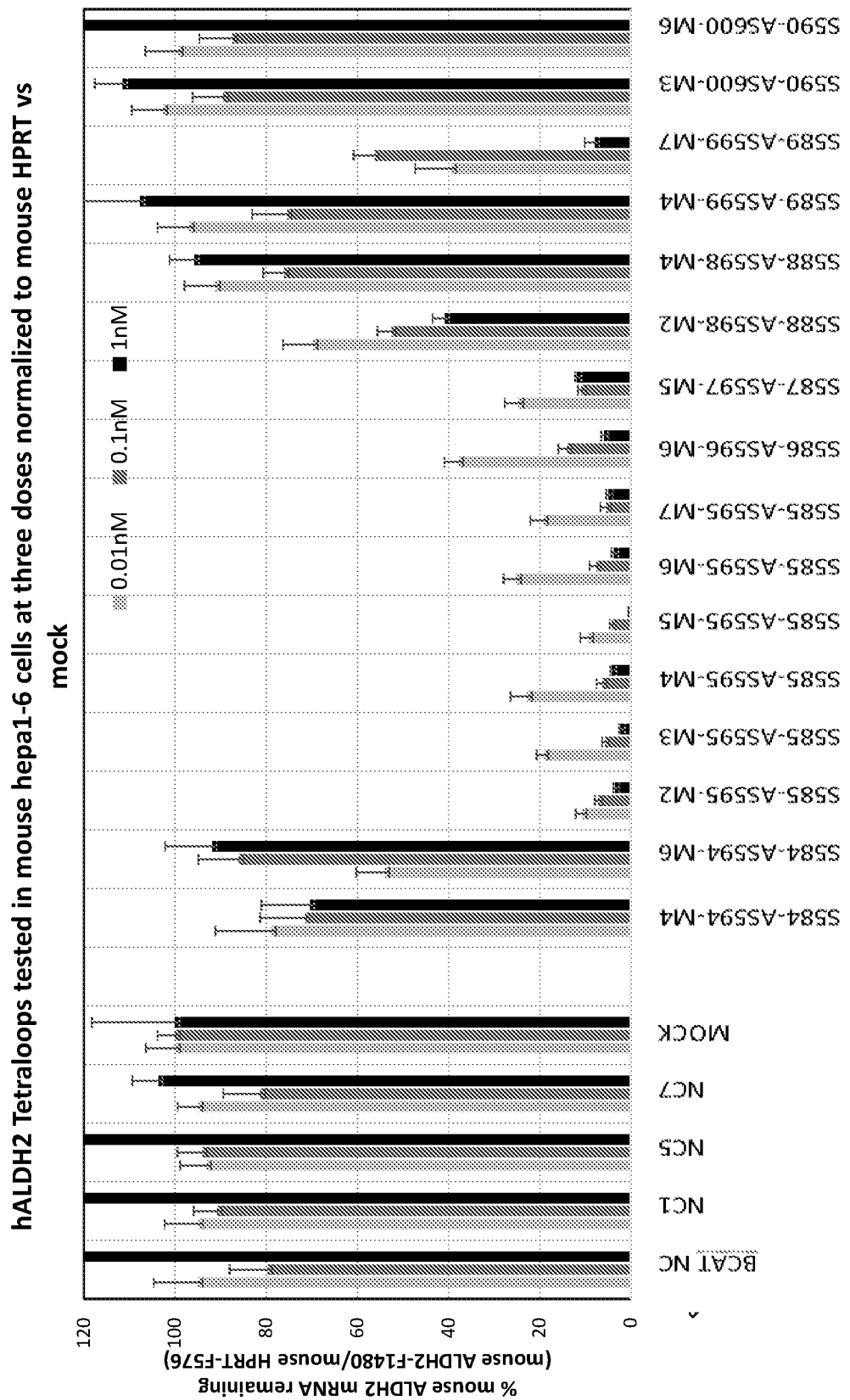
FIG. 6 is a graph showing the results of screening in Hepa1-6 cells using ALDH2 oligonucleotides of different base sequences in the nicked tetraloop structure, adapted to different modification patterns, and at three different concentrations (1 nM, 0.1 nM and 0.01 nM).

Certain tetraloop-modified oligonucleotides were further tested in Hepa1-6 cells using the same modification patterns for each compound (FIG. 6). The target mRNA levels were normalized based on hypoxanthine ribosyltransferase (HPRT), a housekeeping gene that provides a stable expression reference across samples. The tested oligonucleotides in FIG. 6 are shown compared to negative control sequences (BCAT NC, NC1, NC5, NC7) and mock transfection.

In Vivo Murine Experimentation

Data from the above in vitro experiments were assessed to identify tetraloops and modification patterns that would improve delivery properties while maintaining activity for reduction of ALDH2 expression in the mouse hepatocytes. Based on this analysis, select oligonucleotides were then conjugated to GalNAc moieties. Four GalNAc moieties were conjugated to nucleotides in the tetraloop of the sense strand. Conjugation was performed using a click linker. The GalNAc used was as shown below:

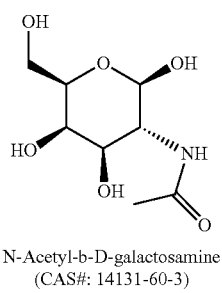

N-Acetyl-b-D-galactosamine
(CAS#: 14131-60-3)

Figure 7:
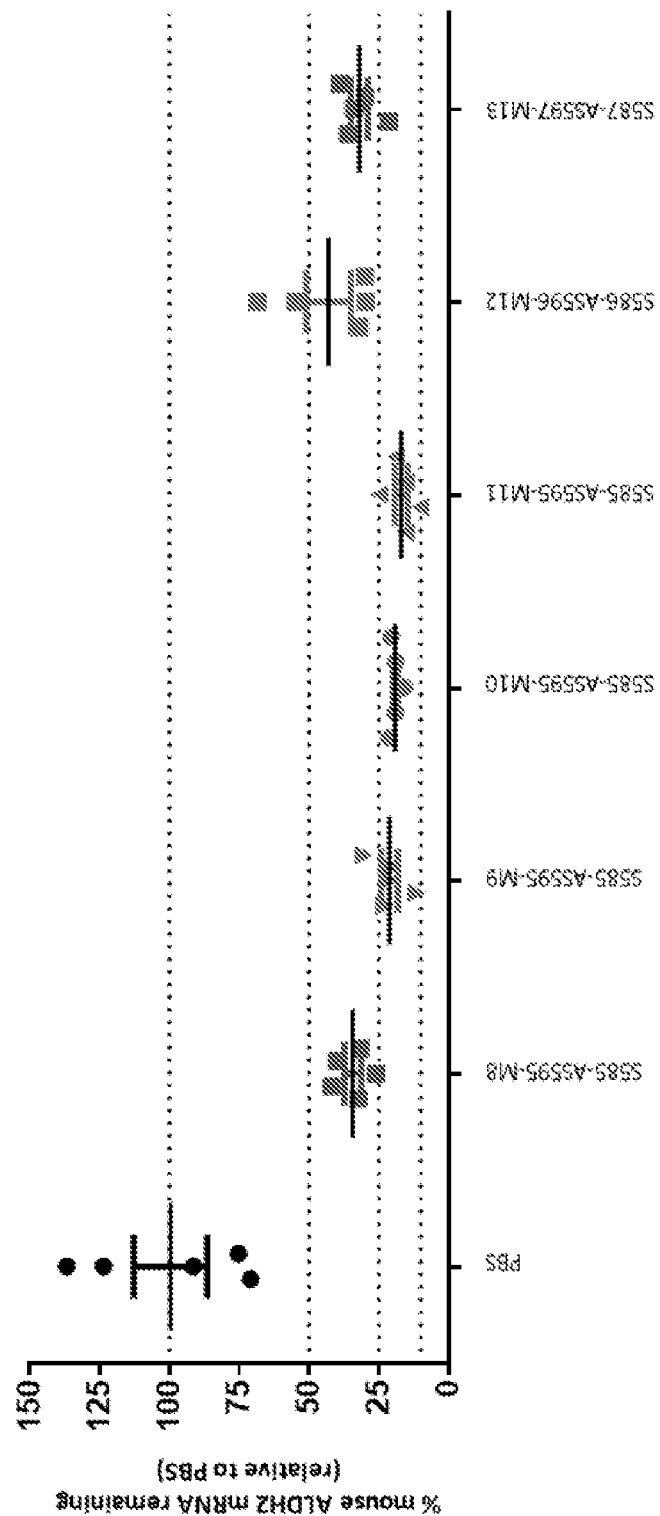
FIG. 7 is a graph showing an in vivo activity evaluation of GalNAc-conjugated ALDH2 oligonucleotides in a nicked tetraloop structure. Three different oligonucleotide sequences were tested. Oligonucleotides were subcutaneously administered to mice at 3 mg/kg. The data show the amount of ALDH2 mRNA remaining at day 4 following administration normalized to PBS control.

A total of six highly potent GalNAc-conjugated ALDH2 oligonucleotides from three different base sequences and having different modification patterns with nicked tetraloop structures were subcutaneously administered to CD-1 mice at 3 mg/kg. Mice were euthanized on day 4 following administration. Liver samples were obtained and RNA was extracted to evaluate ALDH2 mRNA levels by RT-qPCR. The percent ALDH2 mRNA as compared to PBS control mRNA was determined based on these measurements and is shown in FIG. 7.

Example 2: Duration Study of GalNAc-Conjugated ALDH2 Oligonucleotides in Non-Human Primates (NHP)

This study was designed to evaluate pharmacodynamics of a single dose of GalNAc-conjugated ALDH2 oligonucleotides with different modification patterns (e.g., modification patterns that have different numbers of 2'-fluoro modifications and/or different numbers of phosphorothioate linkages in the anti-sense strand). The GalNAc-conjugated ALDH2 oligonucleotides tested in this study were: S585-AS595-M14, S585-AS595-M15, S585-AS595-M16, S585-AS595-M17, S587-AS597-M23, and S587-AS597-M24. A single dose of the GalNAc-conjugated ALDH2 oligonucleotides were subcutaneously administered to non-human primates (n=4 for each group) at 3 mg/kg. Animals fasted overnight and serum samples and liver biopsies were collected prior to feeding the next morning. One pre-dose biopsy was collected for each animal during acclimation and three biopsies were collected 4, 8, or 12, or 16 weeks post administration. The biopsies were divided into two sections, one was flash-frozen and stored at −80° C. and the other was processed in RNAlater (ThermoFisher Scientific) and stored at 4° C. for mRNA level analyses.

Figure 8:
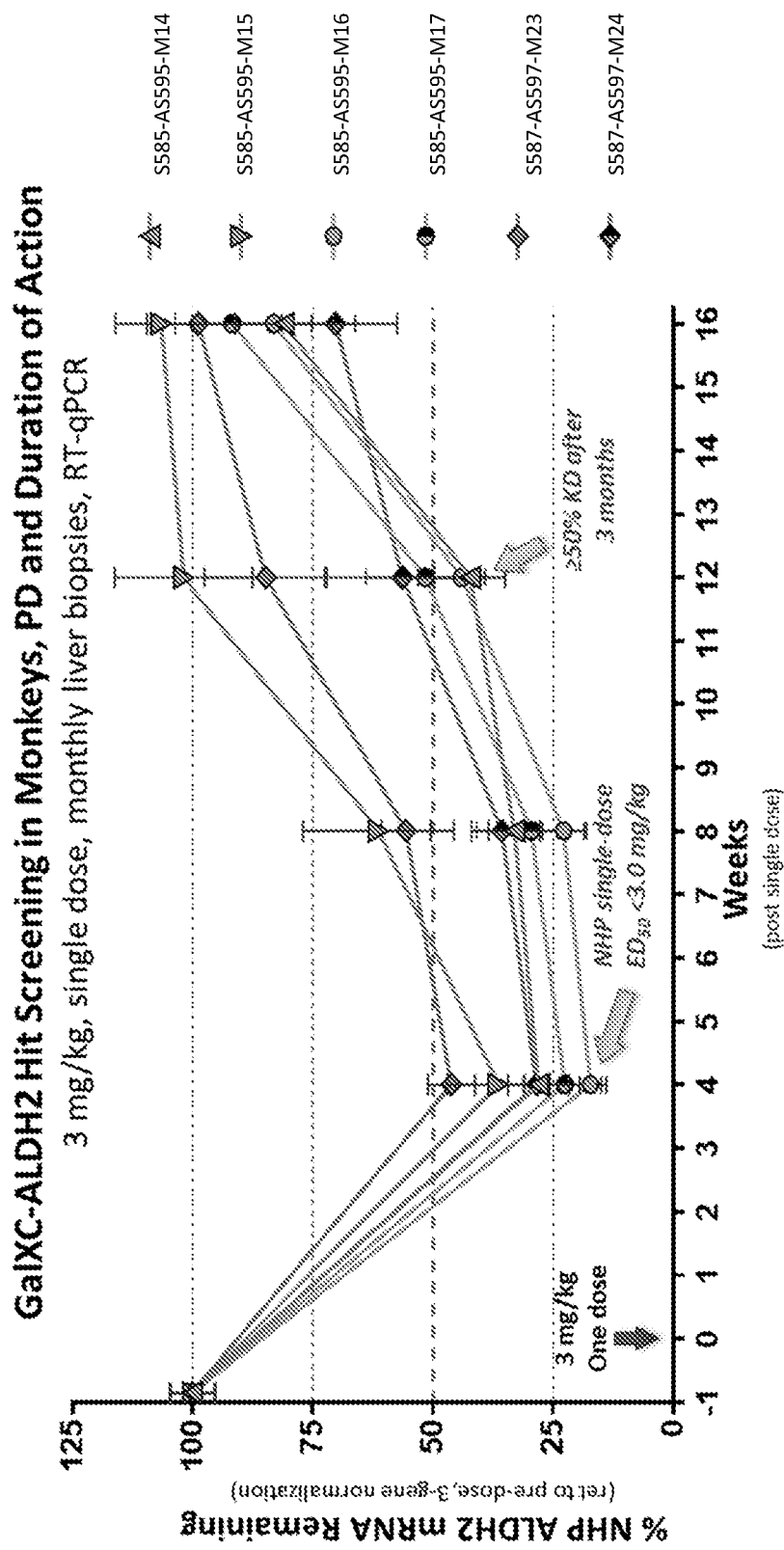
FIG. 8 is a graph showing the results of a duration study of GalNAc-conjugated ALDH2 oligonucleotides with different modification patterns in non-human primates (NHP). A single dose (3 mg/kg) of the oligonucleotides was subcutaneously administered to non-human primates. The data show the amount of ALDH2 mRNA remaining 4, 12, and 16 weeks following administration, relative to the amount of ALDH2 mRNA prior to administration. "*" means one non-human primate was euthanized and not included in the 16-week analysis.

The amount of ALDH2 mRNA remaining 4, 8, 12, or 16 weeks following administration, relative to the amount of ALDH2 mRNA prior to administration were analyzed by quantitative PCR (qPCR) and the results showed that four out of the six GalNAc-conjugated ALDH2 oligonucleotides achieved about 50% ALDH2 mRNA suppression and the effects maintained for three months after a single 3 mg/kg dose (FIG. 8). The results support a proposed dosing frequency of once-per-quarter or less in humans.

The serum samples were for stored liver function panel test, including Alanine Aminotransferase (ALT), Alkaline Phosphatase (ALP) Lactate Dehydrogenase (LDH), Gamma Glutamyl Transferase (GGT).

Example 3: Improving the GalNAc-Conjugated ALDH2 Oligonucleotides Using Different Modification Patterns The study was designed to evaluate the effect of different modification patterns on the activity of GalNAc-conjugated ALDH2 oligonucleotides in reducing ALDH2 mRNA level. As shown in FIG. 9, two GalNAc-conjugated ALDH2 oligonucleotides (S585-AS595 and S587-AS597) in an array of different modification patterns (M14-M40) were screened in an in vivo assay in mice for their activities in reducing ALDH2 mRNA level. Five GalNAc-conjugated ALDH2 oligonucleotides showed higher activities of reducing ALDH2 mRNA level (S585-AS595-M23, S585-AS595-M24, S585-AS595-M16, S585-AS595-M17, and S587-AS597-M23).

Several of the GalNAc-conjugated ALDH2 oligonucleotides tested in FIG. 9 were also tested for their in vivo activity in reducing ALDH2 mRNA level in mice. A single dose of the GalNAc-conjugated ALDH2 oligonucleotides were subcutaneously administered to mice at 0.5 mg/kg and the levels of ALDH2 mRNA in mice liver were evaluated by qPCR 4 days post administration. The results shows that modification patterns M22, M15, M24, M17, M26, M30, and M32 boosted the potency of the oligonucleotides tested compared to modification patterns M21, M14, M23, M16, M25, M29, and M31 (FIG. 10).

Next, the GalNAc-conjugated ALDH2 oligonucleotides that showed higher activities in reducing ALDH2 mRNA level in FIGS. 9 and 10 (S585-AS595-M15, S585-AS595-M16, S585-AS595-M17, S585-AS595-M24, S585-AS595-M26, S585-AS595-M31, S585-AS595-M32) were tested in a dose titration study in mice. The GalNAc-conjugated ALDH2 oligonucleotides were subcutaneously administered to mice at 0.1, 0.3, or 0.5 mg/kg and the levels of ALDH2 mRNA in mice liver were evaluated by qPCR 72 hours post administration. A dose-dependent response was observed for all the oligonucleotides tested (FIG. 11).

The effects of the numbers of phosphorothioate linkages on the activities of two GalNAc-conjugated ALDH2 oligonucleotides (S585-AS595-M33 and S585-AS595-M34) were evaluated. The oligonucleotides were further modified to contain 0, 1, 2, 3, 4, 5, or 6 phosphorothioate linkages at the 5' end of the antisense strand and were subcutaneously administered to mice at 0.5 mg/kg. Levels of remaining ALDH2 mRNA in mice liver were evaluated by qPCR 4 days post administration. The results showed that different numbers of phosphorothioate linkages had different impact on the potency of the GalNAc-conjugated ALDH2 oligonucleotides (FIG. 12).

Finally, the GalNAc-conjugated ALDH2 oligonucleotide (S585-AS595) with different modification patterns (M15, M16, M17, M24 and M26) were tested in a duration study. The GalNAc-conjugated ALDH2 oligonucleotides were subcutaneously administered to mice at 3 mg/kg and the levels of ALDH2 mRNA in mice liver were evaluated by qPCR 72 hours post administration. The results showed that the ALDHN2 mRNA suppression activities of the GalNAc-conjugated ALDH2 oligonucleotides tested lasted for at least 35 days (FIG. 13).

Materials and Methods

Transfection

For the first screen, Lipofectamine RNAiMAX™ was used to complex the oligonucleotides for efficient transfection. Oligonucleotides, RNAiMAX and Opti-MEM incubated together at room temperature for 20 minutes and then 50 µL of this mix was added per well to plates prior to transfection. Media was aspirated from a flask of actively passaging cells and the cells were incubated at 37° C. in the presence of trypsin for 3-5 minutes. After cells no longer adhered to the flask, cell growth media (lacking penicillin and streptomycin) was added to neutralize the trypsin and to suspend the cells. A 10 µL aliquot was removed and counted with a hemocytometer to quantify the cells on a per milliliter basis. For HeLa cells, 25,000 cells were seeded per well in 100 µL of media. A diluted cell suspension was added to the 96-well transfection plates, which already contained the oligonucleotides in Opti-MEM. The transfection plates were then incubated for 24 hours at 37° C. After 24 hours of incubation, media was aspirated from each well. Cells were lysed using the lysis buffer from the Promega RNA Isolation kit. The lysis buffer was added to each well. The lysed cells were then transferred to the Corbett XtractorGENE (QIAxtractor) for RNA isolation or stored at −80° C.

For subsequent screens and experiments, e.g., the secondary screen, Lipofectamine RNAiMAx was used to complex the oligonucleotides for reverse transfection. The complexes were made by mixing RNAiMAX and siRNAs in OptiMEM medium for 15 minutes. The transfection mixture was transferred to multi-well plates and cell suspension was added to the wells. After 24 hours incubation the cells were washed once with PBS and then lysed using lysis buffer from the Promega SV96 kit. The RNA was purified using the SV96 plates in a vacuum manifold. Four microliters of the purified RNA was then heated at 65° C. for 5 minutes and cooled to 4° C. The RNA was then used for reverse transcription using the High Capacity Reverse Transcription kit (Life Technologies) in a 10 microliter reaction. The cDNA was then diluted to 50 µL with nuclease free water and used for quantitative PCR with multiplexed 5'-endonuclease assays and SSoFast qPCR mastermix (Bio-Rad laboratories).

cDNA Synthesis

RNA was isolated from mammalian cells in tissue culture using the Corbett X-tractor Gene™ (QIAxtractor). A modified SuperScript II protocol was used to synthesize cDNA from the isolated RNA. Isolated RNA (approximately 5 ng/µL) was heated to 65° C. for five minutes and incubated with dNPs, random hexamers, oligo dTs, and water. The mixture was cooled for 15 seconds. An "enzyme mix," consisting of water, 5× first strand buffer, DTT, SUPERase•In™ (an RNA inhibitor), and SuperScript II RTase was added to the mixture. The contents were heated to 42° C. for one hour, then to 70° C. for 15 minutes, and then cooled to 4° C. using a thermocycler. The resulting cDNA was then subjected to SYBR®-based qPCR. The qPCR reactions were multiplexed, containing two 5' endonuclease assays per reaction.

qPCR Assays

Primer sets were initially screened using SYBR®-based qPCR. Assay specificity was verified by assessing melt curves as well as "minus RT" controls. Dilutions of cDNA template (10-fold serial dilutions from 20 ng and to 0.02 ng per reaction) from HeLa and Hepa1-6 cells are used to test human (Hs) and mouse (Mm) assays, respectively. qPCR assays were set up in 384-well plates, covered with Micro-Amp film, and run on the 7900HT from Applied Biosystems. Reagent concentrations and cycling conditions included the following: 2× SYBR mix, 10 µM forward primer, 10 µM reverse primer, DD H$_2$O, and cDNA template up to a total volume of 10 µL.

Cloning

PCR amplicons that displayed a single melt-curve were ligated into the pGEM®-T Easy vector kit from Promega according to the manufacturer's instructions. Following the manufacturer's protocol, JM109 High Efficiency cells were transformed with the newly ligated vectors. The cells were then plated on LB plates containing ampicillin and incubated at 37° C. overnight for colony growth.

PCR Screening and Plasmid Mini-Prep

PCR was used to identify colonies of *E. coli* that had been transformed with a vector containing the ligated amplicon of interest. Vector-specific primers that flank the insert were used in the PCR reaction. All PCR products were then run on a 1% agarose gel and imaged by a transilluminator following staining. Gels were assessed qualitatively to determine which plasmids appeared to contain a ligated amplicon of the expected size (approximately 300 bp, including the amplicon and the flanking vector sequences specific to the primers used).

The colonies that were confirmed transformants by PCR screening were then incubated overnight in cultures consisting of 2 mL LB broth with ampicillin at 37° C. with shaking. E. coli cells were then lysed, and the plasmids of interest were isolated using Promega's Mini-Prep kit. Plasmid concentration was determined by UV absorbance at 260 nm.

Plasmid Sequencing and Quantification

Purified plasmids were sequenced using the BigDye® Terminator sequencing kit. The vector-specific primer, T7, was used to give read lengths that span the insert. The following reagents were used in the sequencing reactions: water, 5× sequencing buffer, BigDye terminator mix, T7 primer, and plasmid (100 ng/μL) to a volume of 10 μL. The mixture was held at 96° C. for one minute, then subjected to 15 cycles of 96° C. for 10 seconds, 50° C. for 5 seconds, 60° C. for 1 minute, 15 seconds; 5 cycles of 96° C. for 10 seconds, 50° C. for 5 seconds, 60° C. for 1 minute, 30 seconds; and 5 cycles of 96° C. for 10 seconds, 50° C. for 5 seconds, and 60° C. for 2 minutes. Dye termination reactions were then sequenced using Applied Biosystems' capillary electrophoresis sequencers.

Sequence-verified plasmids were then quantified. They were linearized using a single cutting restriction endonuclease. Linearity was confirmed using agarose gel electrophoresis. All plasmid dilutions were made in TE buffer (pH 7.5) with 100 μg of tRNA per mL buffer to reduce non-specific binding of plasmid to the polypropylene vials.

The linearized plasmids were then serially diluted from 1,000,000 to 01 copies per μL and subjected to qPCR. Assay efficiency was calculated and the assays were deemed acceptable if the efficiency was in the range of 90-110%.

Multi-Plexing Assays

For each target, mRNA levels were quantified by two 5' nuclease assays. In general, several assays are screened for each target. The two assays selected displayed a combination of good efficiency, low limit of detection, and broad 5'→3' coverage of the gene of interest (GOI). Both assays against one GOI could be combined in one reaction when different fluorophores were used on the respective probes. Thus, the final step in assay validation was to determine the efficiency of the selected assays when they were combined in the same qPCR or "multi-plexed."

Linearized plasmids for both assays in 10-fold dilutions were combined and qPCR was performed. The efficiency of each assay was determined as described above. The accepted efficiency rate was 90-110%.

While validating multi-plexed reactions using linearized plasmid standards, $C_q$ values for the target of interest were also assessed using cDNA as the template. For human or mouse targets, HeLa and Hepa1-6 cDNA were used, respectively. The cDNA, in this case, was derived from RNA isolated on the Corbett (~5 ng/μl in water) from untransfected cells. In this way, the observed $C_q$ values from this sample cDNA were representative of the expected $C_q$ values from a 96-well plate transfection. In cases where $C_q$ values were greater than 30, other cell lines were sought that exhibit higher expression levels of the gene of interest. A library of total RNA isolated from via high-throughput methods on the Corbett from each human and mouse line was generated and used to screen for acceptable levels of target expression.

Description of Oligonucleotide Nomenclature

All oligonucleotides described herein are designated either $SN_1$-$ASN_2$-$MN_3$. The following designations apply:

$N_1$: sequence identifier number of the sense strand sequence $N_2$: sequence identifier number of the antisense strand sequence $N_3$: reference number of modification pattern, in which each number represents a pattern of modified nucleotides in the oligonucleotide.

For example, S27-AS317-M1 represents an oligonucleotide with a sense sequence that is set forth by SEQ ID NO: 27, an antisense sequence that is set forth by SEQ ID NO: 317, and which is adapted to a modification pattern identified as M1.

TABLE 4

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S1-AS291-M1 | GAGGUCUUCUGCAACCAGA UUUUCA | 1 | UGAAAAUCUGGUUGCAGAA GACCUCGG | 291 |
| S2-AS292-M1 | AGGUCUUCUGCAACCAGAU UUUCAT | 2 | AUGAAAAUCUGGUUGCAGA AGACCUCG | 292 |
| S3-AS293-M1 | GUCUUCUGCAACCAGAUUU UCAUAA | 3 | UUAUGAAAAUCUGGUUGCA GAAGACCU | 293 |
| S4-AS294-M1 | CUUCUGCAACCAGAUUUUC AUAAAC | 4 | GUUUAUGAAAAUCUGGUUG CAGAAGAC | 294 |
| S5-AS295-M1 | UUCUGCAACCAGAUUUUCA UAAACA | 5 | UGUUUAUGAAAAUCUGGUU GCAGAAGA | 295 |
| S6-AS296-M1 | UCUGCAACCAGAUUUUCAU AAACAA | 6 | UUGUUUAUGAAAAUCUGGU UGCAGAAG | 296 |
| S7-AS297-M1 | CUGCAACCAGAUUUUCAUA AACAAT | 7 | AUUGUUUAUGAAAAUCUGG UUGCAGAA | 297 |
| S8-AS298-M1 | UGCAACCAGAUUUUCAUA AACAATG | 8 | CAUUGUUUAUGAAAAUCUG GUUGCAGA | 298 |
| S9-AS299-M1 | GCAACCAGAUUUUCAUAA ACAAUGA | 9 | UCAUUGUUUAUGAAAAUCU GGUUGCAG | 299 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S10-AS300-M1 | CAACCAGAUUUUCAUAAAC AAUGAA | 10 | UUCAUUGUUUAUGAAAAUC UGGUUGCA | 300 |
| S11-AS301-M1 | AACCAGAUUUUCAUAAAC AAUGAAT | 11 | AUUCAUUGUUUAUGAAAAU CUGGUUGC | 301 |
| S12-AS302-M1 | ACCAGAUUUUCAUAAACA AUGAATG | 12 | CAUUCAUUGUUUAUGAAAA UCUGGUUG | 302 |
| S13-AS303-M1 | CCAGAUUUUCAUAAACAA UGAAUGG | 13 | CCAUUCAUUGUUUAUGAAA AUCUGGUU | 303 |
| S14-AS304-M1 | CAGAUUUUCAUAAACAAU GAAUGGC | 14 | GCCAUUCAUUGUUUAUGAA AAUCUGGU | 304 |
| S17-AS307-M1 | AGAUUUUCAUAAACAAUG AAUGGCA | 17 | UGCCAUUCAUUGUUUAUGA AAAUCUGG | 307 |
| S18-AS308-M1 | GAUUUUCAUAAACAAUGA AUGGCAC | 18 | GUGCCAUUCAUUGUUUAUG AAAAUCUG | 308 |
| S19-AS309-M1 | GCCGUCAGCAGGAAAACAU UCCCCA | 19 | UGGGGAAUGUUUUCCUGCU GACGGCAU | 309 |
| S20-AS310-M1 | CCGUCAGCAGGAAAACAUU CCCCAC | 20 | GUGGGGAAUGUUUUCCUGC UGACGGCA | 310 |
| S21-AS311-M1 | GGCCUUGGAGACCCUGGAC AAUGGC | 21 | GCCAUUGUCCAGGGUCUCC AAGGCCGC | 311 |
| S22-AS312-M1 | GCCUUGGAGACCCUGGACA AUGGCA | 22 | UGCCAUUGUCCAGGGUCUC CAAGGCCG | 312 |
| S23-AS313-M1 | CCUUGGAGACCCUGGACAA UGGCAA | 23 | UUGCCAUUGUCCAGGGUCU CCAAGGCC | 313 |
| S24-AS314-M1 | UACCUGGUGGAUUUGGAC AUGGUCC | 24 | GGACCAUGUCCAAAUCCAC CAGGUAGG | 314 |
| S25-AS315-M1 | ACCUGGUGGAUUUGGACA UGGUCCT | 25 | AGGACCAUGUCCAAAUCCA CCAGGUAG | 315 |
| S26-AS316-M1 | CCUGGUGGAUUUGGACAU GGUCCTC | 26 | GAGGACCAUGUCCAAAUCC ACCAGGUA | 316 |
| S27-AS317-M1 | CUGGUGGAUUUGGACAUG GUCCUCA | 27 | UGAGGACCAUGUCCAAAUC CACCAGGU | 317 |
| S28-AS318-M1 | UGGUGGAUUUGGACAUGG UCCUCAA | 28 | UUGAGGACCAUGUCCAAAU CCACCAGG | 318 |
| S29-AS319-M1 | GGUGGAUUUGGACAUGGU CCUCAAA | 29 | UUUGAGGACCAUC.UCCAAA UCCACCAG | 319 |
| S30-AS320-M1 | GUGGAUUUGGACAUGGUC CUCAAAT | 30 | AUUUGAGGACCAUGUCCAA AUCCACCA | 320 |
| S31 -AS321-M1 | UGGAUUUGGACAUGGUCC UCAAATG | 31 | CAUUUGAGGACCAUGUCCA AAUCCACC | 321 |
| S32-AS322-M1 | GAUUUGGACAUGGUCCUC AAAUGTC | 32 | GACAUUUGAGGACCAUGUC CAAAUCCA | 322 |
| S33-AS323-M1 | UUCCCGCUCCUGAUGCAAG CAUGGA | 33 | UCCAUGCUUGCAUCAGGAG CGGGAAAU | 323 |
| S34-AS324-M1 | UCCCGCUCCUGAUGCAAGC AUGGAA | 34 | UUCCAUGCUUGCAUCAGGA GCGGGAAA | 324 |
| S35-AS325-M1 | CCCGCUCCUGAUGCAAGCA UGGAAG | 35 | CUUCCAUGCUUGCAUCAGG AGCGGGAA | 325 |
| S36-AS326-M1 | CCGCUCCUGAUGCAAGCAU GGAAGC | 36 | GCUUCCAUGCUUGCAUCAG GAGCGGGA | 326 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S37-AS327-M1 | CGCUCCUGAUGCAAGCAUG GAAGCT | 37 | AGCUUCCAUGCUUGCAUCA GGAGCGGG | 327 |
| S38-AS328-M1 | GCUCCUGAUGCAAGCAUGG AAGCTG | 38 | CAGCUUCCAUGCUUGCAUC AGGAGCGG | 328 |
| S39-AS329-M1 | CUCCUGAUGCAAGCAUGGA AGCUGG | 39 | CCAGCUUCCAUGCUUGCAU CAGGAGCG | 329 |
| S40-AS330-M1 | UCCUGAUGCAAGCAUGGA AGCUGGG | 40 | CCCAGCUUCCAUGCUUGCA UCAGGAGC | 330 |
| S41-AS331-M1 | AACUGGAAACGUGGUUGU GAUGAAG | 41 | CUUCAUCACAACCACGUUU CCAGUUGC | 331 |
| S42-AS332-M1 | ACUGGAAACGUGGUUGUG AUGAAGG | 42 | CCUUCAUCACAACCACGUU UCCAGUUG | 332 |
| S43-AS333-M1 | CUGGAAACGUGGUUGUGA UGAAGGT | 43 | ACCUUCAUCACAACCACC.U UUCCAGUU | 333 |
| S44-AS334-M1 | UGGAAACGUGGUUGUGAU GAAGGTA | 44 | UACCUUCAUCACAACCACG UUUCCAGU | 334 |
| S45-AS335-M1 | GGAAACGUGGUUGUGAUG AAGGUAG | 45 | CUACCUUCAUCACAACCAC GUUUCCAG | 335 |
| S46-AS336-M1 | GAAACGUGGUUGUGAUGA AGGUAGC | 46 | GCUACCUUCAUCACAACCA CGUUUCCA | 336 |
| S47-AS337-M1 | AACGUGGUUGUGAUGAAG GUAGCTG | 47 | CAGCUACCUUCAUCACAAC CACGUUUC | 337 |
| S48-AS338-M1 | ACGUGGUUGUGAUGAAGG UAGCUGA | 48 | UCAGCUACCUUCAUCACAA CCACGUUU | 338 |
| S49-AS339-M1 | CGUGGUUGUGAUGAAGGU AGCUGAG | 49 | CUCAGCUACCUUCAUCACA ACCACGUU | 339 |
| S50-AS340-M1 | GUUGUGAUGAAGGUAGCU GAGCAGA | 50 | UCUGCUCAGCUACCUUCAU CACAACCA | 340 |
| S51-AS341-M1 | GUGAUGAAGGUAGCUGAG CAGACAC | 51 | GUGUCUGCUCAGCUACCUU CAUCACAA | 341 |
| S52-AS342-M1 | AGGAUGUGGACAAAGUGG CAUUCAC | 52 | GUGAAUGCCACUUUGUCCA CAUCCUCA | 342 |
| S53-AS343-M1 | GGGAGCAGCAACCUCAAGA GAGUGA | 53 | UCACUCUCUUGAGGUUGCU GCUCCCAG | 343 |
| S54-AS344-M1 | GGAGCAGCAACCUCAAGAG AGUGAC | 54 | GUCACUCUCUUGAGGUUGC UGCUCCCA | 344 |
| S55-AS345-M1 | GAGCAGCAACCUCAAGAGA GUGACC | 55 | GGUCACUCUCUUGAGGUUG CUGCUCCC | 345 |
| S56-AS346-M1 | AGCAGCAACCUCAAGAGAG UGACCT | 56 | AGGUCACUCUCUUGAGGUU GCUGCUCC | 346 |
| S57-AS347-M1 | GCAGCAACCUCAAGAGAGU GACCTT | 57 | AAGGUCACUCUCUUGAGGU UGCUGCUC | 347 |
| S58-AS348-M1 | GCCCUGUUCUUCAACCAGG GCCAGT | 58 | ACUGGCCCUGGUUGAAGAA CAGGGCGA | 348 |
| S59-AS349-M1 | CCCUGUUCUUCAACCAGGG CCAGTG | 59 | CACUGGCCCUGGUUGAAGA ACAGGGCG | 349 |
| S60-AS350-M1 | CCUGUUCUUCAACCAGGGC CAGUGC | 60 | GCACUGGCCCUGGUUGAAG AACAGGGC | 350 |
| S61-AS351-M1 | CUGUUCUUCAACCAGGGCC AGUGCT | 61 | AGCACUGGCCCUGGUUGAA GAACAGGG | 351 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S62-AS352-M1 | UGUUCUUCAACCAGGGCCAGUGCUG | 62 | CAGCACUGGCCCUGGUUGAAGAACAGG | 352 |
| S63-AS353-M1 | GUUCUUCAACCAGGGCCAGUGCUGC | 63 | GCAGCACUGGCCCUGGUUGAAGAACAG | 353 |
| S64-AS354-M1 | UUCUUCAACCAGGGCCAGUGCUGCT | 64 | AGCAGCACUGGCCCUGGUUGAAGAACA | 354 |
| S65-AS355-M1 | CUUCAACCAGGGCCAGUGCUGCUGT | 65 | ACAGCAGCACUGGCCCUGGUUGAAGAA | 355 |
| S66-AS356-M1 | UUCAACCAGGGCCAGUGCUGCUGTG | 66 | CACAGCAGCACUGGCCCUGGUUGAAGA | 356 |
| S67-AS357-M1 | CAACCAGGGCCAGUGCUGCUGUGCC | 67 | GGCACAGCAGCACUGGCCCUGGUUGAA | 357 |
| S68-AS358-M1 | GGCUCCCGGACCUUCGUGCAGGAGG | 68 | CCUCCUGCACGAAGGUCCGGGAGCCGG | 358 |
| S69-AS359-M1 | GCUCCCGGACCUUCGUGCAGGAGGA | 69 | UCCUCCUGCACGAAGGUCCGGGAGCCG | 359 |
| S70-AS360-M1 | CUCCCGGACCUUCGUGCAGGAGGAC | 70 | GUCCUCCUGCACGAAGGUCCGGGAGCC | 360 |
| S71-AS361-M1 | UCCCGGACCUUCGUGCAGGAGGACA | 71 | UGUCCUCCUGCACGAAGGUCCGGGAGC | 361 |
| S72-AS362-M1 | CCCGGACCUUCGUGCAGGAGGACAT | 72 | AUGUCCUCCUGCACGAAGGUCCGGGAG | 362 |
| S73-AS363-M1 | CCGGACCUUCGUGCAGGAGGACATC | 73 | GAUGUCCUCCUGCACGAAGGUCCGGGA | 363 |
| S74-AS364-M1 | GGAGGACAUCUAUGAUGAGUUUGTG | 74 | CACAAACUCAUCAUAGAUGUCCUCCUG | 364 |
| S75-AS365-M1 | CGGGCCAAGUCUCGGGUGGUCGGGA | 75 | UCCCGACCACCCGAGACUUGGCCCGGG | 365 |
| S76-AS366-M1 | GGGCCAAGUCUCGGGUGGUCGGGAA | 76 | UUCCCGACCACCCGAGACUUGGCCCGG | 366 |
| S77-AS367-M1 | GCAGGUGGAUGAAACUCAGUUUAAG | 77 | CUUAAACUGAGUUUCAUCCACCUGCGG | 367 |
| S78-AS368-M1 | CAGGUGGAUGAAACUCAGUUUAAGA | 78 | UCUUAAACUGAGUUUCAUCCACCUGCG | 368 |
| S79-AS369-M1 | AGGUGGAUGAAACUCAGUUUAAGAA | 79 | UUCUUAAACUGAGUUUCAUCCACCUGC | 369 |
| S80-AS370-M1 | GGUGGAUGAAACUCAGUUUAAGAAG | 80 | CUUCUUAAACUGAGUUUCAUCCACCUG | 370 |
| S81-AS371-M1 | GUGGAUGAAACUCAGUUUAAGAAGA | 81 | UCUUCUUAAACUGAGUUUCAUCCACCU | 371 |
| S82-AS372-M1 | UGGAUGAAACUCAGUUUAAGAAGAT | 82 | AUCUUCUUAAACUGAGUUUCAUCCACC | 372 |
| S83-AS373-M1 | GGAUGAAACUCAGUUUAAGAAGATC | 83 | GAUCUUCUUAAACUGAGUUUCAUCCAC | 373 |
| S84-AS374-M1 | GAUGAAACUCAGUUUAAGAAGAUCC | 84 | GGAUCUUCUUAAACUGAGUUUCAUCCA | 374 |
| S85-AS375-M1 | AUGAAACUCAGUUUAAGAAGAUCCT | 85 | AGGAUCUUCUUAAACUGAGUUUCAUCC | 375 |
| S86-AS376-M1 | UGAAACUCAGUUUAAGAAGAUCCTC | 86 | GAGGAUCUUCUUAAACUGAGUUUCAUC | 376 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S87-AS377-M1 | GAAACUCAGUUUAAGAAGAUCCUCG | 87 | CGAGGAUCUUCUUAAACUGAGUUUCAU | 377 |
| S88-AS378-M1 | AAACUCAGUUUAAGAAGAUCCUCGG | 88 | CCGAGGAUCUUCUUAAACUGAGUUUCA | 378 |
| S89-AS379-M1 | AACUCAGUUUAAGAAGAUCCUCGGC | 89 | GCCGAGGAUCUUCUUAAACUGAGUUUC | 379 |
| S90-AS380-M1 | ACUCAGUUUAAGAAGAUCCUCGGCT | 90 | AGCCGAGGAUCUUCUUAAACUGAGUUU | 380 |
| S91-AS381-M1 | CUCAGUUUAAGAAGAUCCUCGGCTA | 91 | UAGCCGAGGAUCUUCUUAAACUGAGUU | 381 |
| S92-AS382-M1 | UCAGUUUAAGAAGAUCCUCGGCUAC | 92 | GUAGCCGAGGAUCUUCUUAAACUGAGU | 382 |
| S93-AS383-M1 | CAGUUUAAGAAGAUCCUCGGCUACA | 93 | UGUAGCCGAGGAUCUUCUUAAACUGAG | 383 |
| S94-AS384-M1 | AGUUUAAGAAGAUCCUCGGCUACAT | 94 | AUGUAGCCGAGGAUCUUCUUAAACUGA | 384 |
| S95-AS385-M1 | GUUUAAGAAGAUCCUCGGCUACAUC | 95 | GAUGUAGCCGAGGAUCUUCUUAAACUG | 385 |
| S96-AS386-M1 | UUUAAGAAGAUCCUCGGCUACAUCA | 96 | UGAUGUAGCCGAGGAUCUUCUUAAACU | 386 |
| S97-AS387-M1 | UUAAGAAGAUCCUCGGCUACAUCAA | 97 | UUGAUGUAGCCGAGGAUCUUCUUAAAC | 387 |
| S98-AS388-M1 | UAAGAAGAUCCUCGGCUACAUCAAC | 98 | GUUGAUGUAGCCGAGGAUCUUCUUAAA | 388 |
| S99-AS389-M1 | AAGAAGAUCCUCGGCUACAUCAACA | 99 | UGUUGAUGUAGCCGAGGAUCUUCUUAA | 389 |
| S100-AS390-M1 | AGAAGAUCCUCGGCUACAUCAACAC | 100 | GUGUUGAUGUAGCCGAGGAUCUUCUUA | 390 |
| S101-AS391-M1 | GAAGAUCCUCGGCUACAUCAACACG | 101 | CGUGUUGAUGUAGCCGAGGAUCUUCUU | 391 |
| S102-AS392-M1 | AAGAUCCUCGGCUACAUCACACGG | 102 | CCGUGUUGAUGUAGCCGAGGAUCUUCU | 392 |
| S103-AS393-M1 | AGAUCCUCGGCUACAUCAACACGGG | 103 | CCCGUGUUGAUGUAGCCGAGGAUCUUC | 393 |
| S104-AS394-M1 | UGCUGCUGACCGUGGUUACUUCAUC | 104 | GAUGAAGUAACCACGGUCAGCAGCAAU | 394 |
| S105-AS395-M1 | GCUGCUGACCGUGGUUACUUCAUCC | 105 | GGAUGAAGUAACCACGGUCAGCAGCAA | 395 |
| S106-AS396-M1 | CUGCUGACCGUGGUUACUUCAUCCA | 106 | UGGAUGAAGUAACCACGGUCAGCAGCA | 396 |
| S107-AS397-M1 | GCUGACCGUGGUUACUUCAUCCAGC | 107 | GCUGGAUGAAGUAACCACGGUCAGCAG | 397 |
| S108-AS398-M1 | CCAGUGAUGCAGAUCCUGAAGUUCA | 108 | UGAACUUCAGGAUCUGCAUCACUGGCC | 398 |
| S109-AS399-M1 | AGUGAUGCAGAUCCUGAAGUUCAAG | 109 | CUUGAACUUCAGGAUCUGCAUCACUGG | 399 |
| S110-AS400-M1 | GUGAUGCAGAUCCUGAAGUUCAAGA | 110 | UCUUGAACUUCAGGAUCUGCAUCACUG | 400 |
| S111-AS401-M1 | UGAUGCAGAUCCUGAAGUUCAAGAC | 111 | GUCUUGAACUUCAGGAUCUGCAUCACU | 401 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S112-AS402-M1 | GAUGCAGAUCCUGAAGUUCAAGACC | 112 | GGUCUUGAACUUCAGGAUCUGCAUCAC | 402 |
| S113-AS403-M1 | AUGCAGAUCCUGAAGUUCAAGACCA | 113 | UGGUCUUGAACUUCAGGAUCUGCAUCA | 403 |
| S114-AS404-M1 | GCAGAUCCUGAAGUUCAAGACCATA | 114 | UAUGGUCUUGAACUUCAGGAUCUGCAU | 404 |
| S115-AS405-M1 | CAGAUCCUGAAGUUCAAGACCAUAG | 115 | CUAUGGUCUUGAACUUCAGGAUCUGCA | 405 |
| S116-AS406-M1 | AGAUCCUGAAGUUCAAGACCAUAGA | 116 | UCUAUGGUCUUGAACUUCAGGAUCUGC | 406 |
| S117-AS407-M1 | GAUCCUGAAGUUCAAGACCAUAGAG | 117 | CUCUAUGGUCUUGAACUUCAGGAUCUG | 407 |
| S118-AS408-M1 | UCCUGAAGUUCAAGACCAUAGAGGA | 118 | UCCUCUAUGGUCUUGAACUUCAGGAUC | 408 |
| S119-AS409-M1 | AAGUUCAAGACCAUAGAGGAGGUUG | 119 | CAACCUCCUCUAUGGUCUUGAACUUCA | 409 |
| S120-AS410-M1 | GCUGUCUUCACAAAGGAUUUGGACA | 120 | UGUCCAAAUCCUUUGUGAAGACAGCUG | 410 |
| S121-AS411-M1 | GUCUUCACAAAGGAUUUGGACAAGG | 121 | CCUUGUCCAAAUCCUUUGUGAAGACAG | 411 |
| S122-AS412-M1 | GCAGGCAUACACUGAAGUGAAAACT | 122 | AGUUUUCACUUCAGUGUAUGCCUGCAG | 412 |
| S123-AS413-M1 | CAGGCAUACACUGAAGUGAAAACTG | 123 | CAGUUUUCACUUCAGUGUAUGCCUGCA | 413 |
| S124-AS414-M1 | AGGCAUACACUGAAGUGAAACUGT | 124 | ACAGUUUUCACUUCAGUGUAUGCCUGC | 414 |
| S125-AS415-M1 | GGCAUACACUGAAGUGAAAACUGUC | 125 | GACAGUUUUCACUUCAGUGUAUGCCUG | 415 |
| S126-AS416-M1 | GCAUACACUGAAGUGAAAACUGUCA | 126 | UGACAGUUUUCACUUCAGUGUAUGCCU | 416 |
| S127-AS417-M1 | AUACACUGAAGUGAAAACUGUCACA | 127 | UGUGACAGUUUUCACUUCAGUGUAUGC | 417 |
| S128-AS418-M1 | UACACUGAAGUGAAAACUGUCACAG | 128 | CUGUGACAGUUUUCACUUCAGUGUAUG | 418 |
| S129-AS419-M1 | CUGAAGUGAAAACUGUCACAGUCAA | 129 | UUGACUGUGACAGUUUUCACUUCAGUG | 419 |
| S130-AS420-M1 | GUCAAAGUGCCUCAGAAGAACUCAT | 130 | AUGAGUUCUUCUGAGGCACUUUGACUG | 420 |
| S131-AS421-M1 | CAAAGUGCCUCAGAAGAACUCAUAA | 131 | UUAUGAGUUCUUCUGAGGCACUUUGAC | 421 |
| S132-AS422-M1 | AAGUGCCUCAGAAGAACUCAUAAGA | 132 | UCUUAUGAGUUCUUCUGAGGCACUUUG | 422 |
| S133-AS423-M1 | AGUGCCUCAGAAGAACUCAUAAGAA | 133 | UUCUUAUGAGUUCUUCUGAGGCACUUU | 423 |
| S134-AS424-M1 | GUGCCUCAGAAGAACUCAUAAGAAT | 134 | AUUCUUAUGAGUUCUUCUGAGGCACUU | 424 |
| S135-AS425-M1 | UGCCUCAGAAGAACUCAUAAGAATC | 135 | GAUUCUUAUGAGUUCUUCUGAGGCACU | 425 |
| S136-AS426-M1 | CCUCAGAAGAACUCAUAAGAAUCAT | 136 | AUGAUUCUUAUGAGUUCUUCUGAGGCA | 426 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S137-AS427-M1 | CUCAGAAGAACUCAUAAG AAUCATG | 137 | CAUGAUUCUUAUGAGUUCU UCUGAGGC | 427 |
| S138-AS428-M1 | UCAGAAGAACUCAUAAGA AUCAUGC | 138 | GCAUGAUUCUUAUGAGUUC UUCUGAGG | 428 |
| S139-AS429-M1 | CAGAAGAACUCAUAAGAA UCAUGCA | 139 | UGCAUGAUUCUUAUGAGUU CUUCUGAG | 429 |
| S140-AS430-M1 | AGAAGAACUCAUAAGAAU CAUGCAA | 140 | UUGCAUGAUUCUUAUGAGU UCUUCUGA | 430 |
| S141-AS431-M1 | GAAGAACUCAUAAGAAUC AUGCAAG | 141 | CUUGCAUGAUUCUUAUGAG UUCUUCUG | 431 |
| S142-AS432-M1 | AAGAACUCAUAAGAAUCA UGCAAGC | 142 | GCUUGCAUGAUUCUUAUGA GUUCUUCU | 432 |
| S143-AS433-M1 | GAACUCAUAAGAAUCAUG CAAGCTT | 143 | AAGCUUGCAUGAUUCUUAU GAGUUCUU | 433 |
| S144-AS434-M1 | AACUCAUAAGAAUCAUGC AAGCUTC | 144 | GAAGCUUGCAUGAUUCUUA UGAGUUCU | 434 |
| S145-AS435-M1 | CCCUCAGCCAUUGAUGGAA AGUUCA | 145 | UGAACUUUCCAUCAAUGGC UGAGGGAG | 435 |
| S146-AS436-M1 | CCUCAGCCAUUGAUGGAAA GUUCAG | 146 | CUGAACUUUCCAUCAAUGG CUGAGGGA | 436 |
| S147-AS437-M1 | UCAGCCAUUGAUGGAAAG UUCAGCA | 147 | UGCUGAACUUUCCAUCAAU GGCUGAGG | 437 |
| S148-AS438-M1 | CAGCCAUUGAUGGAAAGU UCAGCAA | 148 | UUGCUGAACUUUCCAUCAA UGGCUGAG | 438 |
| S149-AS439-M1 | AGCCAUUGAUGGAAAGUU CAGCAAG | 149 | CUUGCUGAACUUUCCAUCA AUGGCUGA | 439 |
| S150-AS440-M1 | GCCAUUGAUGGAAAGUUC AGCAAGA | 150 | UCUUGCUGAACUUUCCAUC AAUGGCUG | 440 |
| S151-AS441-M1 | CCAUUGAUGGAAAGUUCA GCAAGAT | 151 | AUCUUGCUGAACUUUCCAU CAAUGGCU | 441 |
| S152-AS442-M1 | CAUUGAUGGAAAGUUCAG CAAGATC | 152 | GAUCUUGCUGAACUUUCCA UCAAUGGC | 442 |
| S153-AS443-M1 | AUUGAUGGAAAGUUCAGC AAGAUCA | 153 | UGAUCUUGCUGAACUUUCC AUCAAUGG | 443 |
| S154-AS444-M1 | UUGAUGGAAAGUUCAGCA AGAUCAG | 154 | CUGAUCUUGCUGAACUUUC CAUCAAUG | 444 |
| S155-AS445-M1 | UGAUGGAAAGUUCAGCAA GAUCAGC | 155 | GCUGAUCUUGCUGAACUUU CCAUCAAU | 445 |
| S156-AS446-M1 | GAUGGAAAGUUCAGCAAG AUCAGCA | 156 | UGCUGAUCUUGCUGAACUU UCCAUCAA | 446 |
| S157-AS447-M1 | AUGGAAAGUUCAGCAAGA UCAGCAA | 157 | UUGCUGAUCUUGCUGAACU UUCCAUCA | 447 |
| S158-AS448-M1 | UGGAAAGUUCAGCAAGAU CAGCAAC | 158 | GUUGCUGAUCUUGCUGAAC UUUCCAUC | 448 |
| S159-AS449-M1 | GGAAAGUUCAGCAAGAUC AGCAACA | 159 | UGUUGCUGAUCUUGCUGAA CUUUCCAU | 449 |
| S160-AS450-M1 | GAAAGUUCAGCAAGAUCA GCAACAA | 160 | UUGUUGCUGAUCUUGCUGA ACUUUCCA | 450 |
| S161-AS451-M1 | AAAGUUCAGCAAGAUCAG CAACAAA | 161 | UUUGUUGCUGAUCUUGCUG AACUUUCC | 451 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S162-AS452-M1 | AAGUUCAGCAAGAUCAGCAACAAAA | 162 | UUUUGUUGCUGAUCUUGCUGAACUUUC | 452 |
| S163-AS453-M1 | AUCAGCAACAAAACCAAGAAAAATG | 163 | CAUUUUUCUUGGUUUUGUUGCUGAUCU | 453 |
| S164-AS454-M1 | CAGCAACAAAACCAAGAAAAAUGAT | 164 | AUCAUUUUCUUGGUUUGUUGCUGAU | 454 |
| S165-AS455-M1 | AGCAACAAAACCAAGAAAAAUGAUC | 165 | GAUCAUUUUCUUGGUUUUGUUGCUGA | 455 |
| S166-AS456-M1 | ACAAAACCAAGAAAAAUGAUCCUTG | 166 | CAAGGAUCAUUUUCUUGGUUUUGUUG | 456 |
| S167-AS457-M1 | CAAAACCAAGAAAAAUGAUCCUUGC | 167 | GCAAGGAUCAUUUUCUUGGUUUUGUU | 457 |
| S168-AS458-M1 | AGAAAAAUGAUCCUUGCGUGCUGAA | 168 | UUCAGCACGCAAGGAUCAUUUUCUUG | 458 |
| S169-AS459-M1 | AAAAAUGAUCCUUGCGUGCUGAATA | 169 | UAUUCAGCACGCAAGGAUCAUUUUCU | 459 |
| S170-AS460-M1 | AAAAUGAUCCUUGCGUGCUGAAUAT | 170 | AUAUUCAGCACGCAAGGAUCAUUUUC | 460 |
| S171-AS461-M1 | AAAUGAUCCUUGCGUGCUGAAUAUC | 171 | GAUAUUCAGCACGCAAGGAUCAUUUU | 461 |
| S172-AS462-M1 | AAUGAUCCUUGCGUGCUGAAUAUCT | 172 | AGAUAUUCAGCACGCAAGGAUCAUUUU | 462 |
| S173-AS463-M1 | AUGAUCCUUGCGUGCUGAAUAUCTG | 173 | CAGAUAUUCAGCACGCAAGGAUCAUUU | 463 |
| S174-AS464-M1 | UGAUCCUUGCGUGCUGAAUAUCUGA | 174 | UCAGAUAUUCAGCACGCAAGGAUCAUU | 464 |
| S175-AS465-M1 | GAUCCUUGCGUGCUGAAUAUCUGAA | 175 | UUCAGAUAUUCAGCACGCAAGGAUCAU | 465 |
| S176-AS466-M1 | UCCUUGCGUGCUGAAUAUCUGAAAA | 176 | UUUUCAGAUAUUCAGCACGCAAGGAUC | 466 |
| S177-AS467-M1 | CCUUGCGUGCUGAAUAUCUGAAAAG | 177 | CUUUUCAGAUAUUCAGCACGCAAGGAU | 467 |
| S178-AS468-M1 | CUUGCGUGCUGAAUAUCUGAAAAGA | 178 | UCUUUUCAGAUAUUCAGCACGCAAGGA | 468 |
| S179-AS469-M1 | UUGCGUGCUGAAUAUCUGAAAAGAG | 179 | CUCUUUUCAGAUAUUCAGCACGCAAGG | 469 |
| S180-AS470-M1 | UGCGUGCUGAAUAUCUGAAAAGAGA | 180 | UCUCUUUUCAGAUAUUCAGCACGCAAG | 470 |
| S181-AS471-M1 | GCGUGCUGAAUAUCUGAAAAGAGAA | 181 | UUCUCUUUUCAGAUAUUCAGCACGCAA | 471 |
| S182-AS472-M1 | CGUGCUGAAUAUCUGAAAAGAGAAA | 182 | UUUCUCUUUUCAGAUAUUCAGCACGCA | 472 |
| S183-AS473-M1 | GUGCUGAAUAUCUGAAAAGAGAAAT | 183 | AUUUCUCUUUUCAGAUAUUCAGCACGC | 473 |
| S184-AS474-M1 | UGCUGAAUAUCUGAAAAGAAAATT | 184 | AAUUUCUCUUUUCAGAUAUUCAGCACG | 474 |
| S185-AS475-M1 | GCUGAAUAUCUGAAAAGAGAAAUTT | 185 | AAAUUUCUCUUUUCAGAUAUUCAGCAC | 475 |
| S186-AS476-M1 | CUGAAUAUCUGAAAAGAGAAAUUTT | 186 | AAAAUUUCUCUUUUCAGAUAUUCAGCA | 476 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S187-AS477-M1 | UGAAUAUCUGAAAGAGA AAUUUTT | 187 | AAAAAUUUCUCUUUUCAGA UAUUCAGC | 477 |
| S188-AS478-M1 | GAAUAUCUGAAAGAGAA AUUUUTC | 188 | GAAAAUUUCUCUUUUCAG AUAUUCAG | 478 |
| S189-AS479-M1 | AAUAUCUGAAAGAGAAA UUUUUCC | 189 | GGAAAAUUUCUCUUUUCA GAUAUUCA | 479 |
| S190-AS480-M1 | AUAUCUGAAAGAGAAAU UUUUCCT | 190 | AGGAAAAUUUCUCUUUUC AGAUAUUC | 480 |
| S191-AS481-M1 | AUCUGAAAGAGAAAUUU UUCCUAC | 191 | GUAGGAAAAUUUCUCUUU UCAGAUAU | 481 |
| S192-AS482-M1 | GAAAAGAGAAAUUUUUCC UACAAAA | 192 | UUUUGUAGGAAAAUUUCU CUUUUCAG | 482 |
| S193-AS483-M1 | AAAAGAGAAAUUUUUCCU ACAAAT | 193 | AUUUUGUAGGAAAAUUUC UCUUUUCA | 483 |
| S194-AS484-M1 | AGAGAAAUUUUUCCUACA AAAUCTC | 194 | GAGAUUUGUAGGAAAAAU uucucuuu | 484 |
| S195-AS485-M1 | GAGAAAUUUUUCCUACAA AAUCUCT | 195 | AGAGAUUUGUAGGAAAAA UUUCUCUU | 485 |
| S196-AS486-M1 | AGAAAUUUUUCCUACAAA AUCUCTT | 196 | AAGAGAUUUGUAGGAAAA AUUUCUCU | 486 |
| S197-AS487-M1 | CUUGGGUCAAGAAAGUUC UAGAATT | 197 | AAUUCUAGAACUUUCUUGA CCCAAGAG | 487 |
| S198-AS488-M1 | GGGUCAAGAAAGUUCUAG AAUUUGA | 198 | UCAAAUUCUAGAACUUUCU UGACCCAA | 488 |
| S199-AS489-M1 | GGUCAAGAAAGUUCUAGA AUUUGAA | 199 | UUCAAAUUCUAGAACUUUC UUGACCCA | 489 |
| S200-AS490-M1 | GUCAAGAAAGUUCUAGAA UUUGAAT | 200 | AUUCAAAUUCUAGAACUUU CUUGACCC | 490 |
| S201-AS491-M1 | UCAAGAAAGUUCUAGAAU UUGAATT | 201 | AAUUCAAAUUCUAGAACUU UCUUGACC | 491 |
| S202-AS492-M1 | CAAGAAAGUUCUAGAAUU UGAAUTG | 202 | CAAUUCAAAUUCUAGAACU UUCUUGAC | 492 |
| S203-AS493-M1 | AAGAAAGUUCUAGAAUUU GAAUUGA | 203 | UCAAUUCAAAUUCUAGAAC UUUCUUGA | 493 |
| S204-AS494-M1 | AGAAAGUUCUAGAAUUUG AAUUGAT | 204 | AUCAAUUCAAAUUCUAGAA CUUUCUUG | 494 |
| S205-AS495-M1 | GAAAGUUCUAGAAUUUGA AUUGATA | 205 | UAUCAAUUCAAAUUCUAGA ACUUUCUU | 495 |
| S206-AS496-M1 | AAAGUUCUAGAAUUUGAA UUGAUAA | 206 | UUAUCAAUUCAAAUUCUAG AACUUUCU | 496 |
| S207-AS497-M1 | AAGUUCUAGAAUUUGAAU UGAUAAA | 207 | UUUAUCAAUUCAAAUUCUA GAACUUUC | 497 |
| S208-AS498-M1 | AGUUCUAGAAUUUGAAUU GAUAAAC | 208 | GUUUAUCAAUUCAAAUUCU AGAACUUU | 498 |
| S209-AS499-M1 | GUUCUAGAAUUUGAAUUG AUAAACA | 209 | UGUUUAUCAAUUCAAAUUC UAGAACUU | 499 |
| S210-AS500-M1 | UUCUAGAAUUUGAAUUGA UAAACAT | 210 | AUGUUUAUCAAUUCAAAUU CUAGAACU | 500 |
| S211-AS501-M1 | UCUAGAAUUUGAAUUGAU AAACATG | 211 | CAUGUUUAUCAAUUCAAAU UCUAGAAC | 501 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S212-AS502-M1 | CUAGAAUUUGAAUUGAUAAACAUGG | 212 | CCAUGUUUAUCAAUUCAAAUUCUAGAA | 502 |
| S213-AS503-M1 | UAGAAUUUGAAUUGAUAAACAUGGT | 213 | ACCAUGUUUAUCAAUUCAAAUUCUAGA | 503 |
| S214-AS504-M1 | AGAAUUUGAAUUGAUAAACAUGGTG | 214 | CACCAUGUUUAUCAAUUCAAAUUCUAG | 504 |
| S215-AS505-M1 | GAAUUUGAAUUGAUAAACAUGGUGG | 215 | CCACCAUGUUUAUCAAUUCAAAUUCUA | 505 |
| S216-AS506-M1 | UAAGAGUAUAUGAGGAACCUUUUAA | 216 | UUAAAAGGUUCCUCAUAUACUCUUACC | 506 |
| S217-AS507-M1 | AAGAGUAUAUGAGGAACCUUUUAAA | 217 | UUUAAAAGGUUCCUCAUAUACUCUUAC | 507 |
| S218-AS508-M1 | AGAGUAUAUGAGGAACCUUUUAAAC | 218 | GUUUAAAAGGUUCCUCAUAUACUCUUA | 508 |
| S219-AS509-M1 | GAGUAUAUGAGGAACCUUUUAAACG | 219 | CGUUUAAAAGGUUCCUCAUAUACUCUU | 509 |
| S220-AS510-M1 | AGUAUAUGAGGAACCUUUUAAACGA | 220 | UCGUUUAAAAGGUUCCUCAUAUACUCU | 510 |
| S221-AS511-M1 | GUAUAUGAGGAACCUUUUAAACGAC | 221 | GUCGUUUAAAAGGUUCCUCAUAUACUC | 511 |
| S222-AS512-M1 | UAUAUGAGGAACCUUUUAAACGACA | 222 | UGUCGUUUAAAAGGUUCCUCAUAUACU | 512 |
| S223-AS513-M1 | AUGAGGAACCUUUUAAACGACAACA | 223 | UGUUGUCGUUUAAAAGGUUCCUCAUAU | 513 |
| S224-AS514-M1 | GAGGAACCUUUUAAACGACAACAAT | 224 | AUUGUUGUCGUUUAAAAGGUUCCUCAU | 514 |
| S225-AS515-M1 | AGGAACCUUUUAAACGACAACAATA | 225 | UAUUGUUGUCGUUUAAAAGGUUCCUCA | 515 |
| S226-AS516-M1 | GAACCUUUUAAACGACAACAAUACT | 226 | AGUAUUGUUGUCGUUUAAAAGGUUCCU | 516 |
| S227-AS517-M1 | AACCUUUUAAACGACAACAAUACTG | 227 | CAGUAUUGUUGUCGUUUAAAAGGUUCC | 517 |
| S228-AS518-M1 | ACCUUUUAAACGACAACAAUACUGC | 228 | GCAGUAUUGUUGUCGUUUAAAAGGUUC | 518 |
| S229-AS519-M1 | CCUUUUAAACGACAACAAUACUGCT | 229 | AGCAGUAUUGUUGUCGUUUAAAAGGUU | 519 |
| S230-AS520-M1 | CUUUUAAACGACAACAAUACUGCTA | 230 | UAGCAGUAUUGUUGUCGUUUAAAAGGU | 520 |
| S231-AS521-M1 | UAAACGACAACAAUACUGCUAGCTT | 231 | AAGCUAGCAGUAUUGUUGUCGUUUAAA | 521 |
| S232-AS522-M1 | AAACGACAACAAUACUGCUAGCUTT | 232 | AAAGCUAGCAGUAUUGUUGUCGUUUAA | 522 |
| S233-AS523-M1 | AACGACAACAAUACUGCUAGCUUTC | 233 | GAAAGCUAGCAGUAUUGUUGUCGUUUA | 523 |
| S234-AS524-M1 | CGACAACAAUACUGCUAGCUUUCAG | 234 | CUGAAAGCUAGCAGUAUUGUUGUCGUU | 524 |
| S235-AS525-M1 | GACAACAAUACUGCUAGCUUUCAGG | 235 | CCUGAAAGCUAGCAGUAUUGUUGUCGU | 525 |
| S236-AS526-M1 | ACAACAAUACUGCUAGCUUUCAGGA | 236 | UCCUGAAAGCUAGCAGUAUUGUUGUCG | 526 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S237-AS527-M1 | CAACAAUACUGCUAGCUUUCAGGAT | 237 | AUCCUGAAAGCUAGCAGUAUUGUUGUC | 527 |
| S238-AS528-M1 | AACAAUACUGCUAGCUUUCAGGATG | 238 | CAUCCUGAAAGCUAGCAGUAUUGUUGU | 528 |
| S239-AS529-M1 | ACAAUACUGCUAGCUUUCAGGAUGA | 239 | UCAUCCUGAAAGCUAGCAGUAUUGUUG | 529 |
| S240-AS530-M1 | CAAUACUGCUAGCUUUCAGGAUGAT | 240 | AUCAUCCUGAAAGCUAGCAGUAUUGUU | 530 |
| S241-AS531-M1 | AAUACUGCUAGCUUUCAGGAUGATT | 241 | AAUCAUCCUGAAAGCUAGCAGUAUUGU | 531 |
| S242-AS532-M1 | AUACUGCUAGCUUUCAGGAUGAUTT | 242 | AAAUCAUCCUGAAAGCUAGCAGUAUUG | 532 |
| S243-AS533-M1 | UACUGCUAGCUUUCAGGAUGAUUTT | 243 | AAAAUCAUCCUGAAAGCUAGCAGUAUU | 533 |
| S244-AS534-M1 | ACUGCUAGCUUUCAGGAUGAUUUTT | 244 | AAAAAUCAUCCUGAAAGCUAGCAGUAU | 534 |
| S245-AS535-M1 | CUGCUAGCUUUCAGGAUGAUUUUTA | 245 | UAAAAAUCAUCCUGAAAGCUAGCAGUA | 535 |
| S246-AS536-M1 | UGCUAGCUUUCAGGAUGAUUUUUAA | 246 | UUAAAAAUCAUCCUGAAAGCUAGCAGU | 536 |
| S247-AS537-M1 | GCUAGCUUUCAGGAUGAUUUUUAAA | 247 | UUUAAAAAUCAUCCUGAAAGCUAGCAG | 537 |
| S248-AS538-M1 | CUAGCUUUCAGGAUGAUUUUUAAAA | 248 | UUUUAAAAAUCAUCCUGAAAGCUAGCA | 538 |
| S249-AS539-M1 | AGCUUUCAGGAUGAUUUUUAAAAAA | 249 | UUUUUAAAAAUCAUCCUGAAAGCUAG | 539 |
| S250-AS540-M1 | GCUUUCAGGAUGAUUUUUAAAAAAT | 250 | AUUUUUAAAAAUCAUCCUGAAAGCUA | 540 |
| S251-AS541-M1 | CUUUCAGGAUGAUUUUUAAAAAATA | 251 | UAUUUUUUAAAAAUCAUCCUGAAAGCU | 541 |
| S252-AS542-M1 | UUUCAGGAUGAUUUUUAAAAAAUAG | 252 | CUAUUUUUUAAAAAUCAUCUGAAAGC | 542 |
| S253-AS543-M1 | UUCAGGAUGAUUUUUAAAAAAUAGA | 253 | UCUAUUUUUUAAAAAUCAUCCUGAAAG | 543 |
| S254-AS544-M1 | UCAGGAUGAUUUUUAAAAAAUAGAT | 254 | AUCUAUUUUUUAAAAAUCAUCCUGAAA | 544 |
| S255-AS545-M1 | CAGGAUGAUUUUUAAAAAAUAGATT | 255 | AAUCUAUUUUUUAAAAAUCAUCCUGAA | 545 |
| S256-AS546-M1 | AGGAUGAUUUUUAAAAAAUAGAUTC | 256 | GAAUCUAUUUUUUAAAAAUCAUCCUGA | 546 |
| S257-AS547-M1 | GGAUGAUUUUUAAAAAAUAGAUUCA | 257 | UGAAUCUAUUUUUUAAAAAUCAUCCUG | 547 |
| S258-AS548-M1 | GAUGAUUUUUAAAAAAUAGAUUCAA | 258 | UUGAAUCUAUUUUUUAAAAAUCAUCCU | 548 |
| S259-AS549-M1 | AUGAUUUUUAAAAAAUAGAUUCAAA | 259 | UUUGAAUCUAUUUUUUAAAAAUCAUCC | 549 |
| S260-AS550-M1 | UGAUUUUUAAAAAAUAGAUUCAAAT | 260 | AUUUGAAUCUAUUUUUUAAAAAUCAUC | 550 |
| S261-AS551-M1 | GAUUUUUAAAAAAUAGAUUCAAATG | 261 | CAUUUGAAUCUAUUUUUUAAAAAUCAU | 551 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S262-AS552-M1 | AUUUUUAAAAAAUAGAUUCAAAUGT | 262 | ACAUUUGAAUCUAUUUUUAAAAAUCA | 552 |
| S263-AS553-M1 | UUUUUAAAAAAUAGAUUCAAAUGTG | 263 | CACAUUUGAAUCUAUUUUUUAAAAAUC | 553 |
| S264-AS554-M1 | AAACGCUUCCUAUAACUCGAGUUTA | 264 | UAAACUCGAGUUAUAGGAAGCGUUUCA | 554 |
| S265-AS555-M1 | UAUAGGGGAAGAAAAAGCUAUUGTT | 265 | AACAAUAGCUUUUUCUUCCCCUAUAAA | 555 |
| S266-AS556-M1 | AUAGGGGAAGAAAAAGCUAUUGUTT | 266 | AAACAAUAGCUUUUUCUUCCCUAUAA | 556 |
| S267-AS557-M1 | GGGGAAGAAAAAGCUAUUGUUUACA | 267 | UGUAAACAAUAGCUUUUUCUUCCCCUA | 557 |
| S268-AS558-M1 | GGGAAGAAAAAGCUAUUGUUUACAA | 268 | UUGUAAACAAUAGCUUUUUCUUCCCCU | 558 |
| S269-AS559-M1 | GGAAGAAAAAGCUAUUGUUUACAAT | 269 | AUUGUAAACAAUAGCUUUUUCUUCCCC | 559 |
| S270-AS560-M1 | GAAGAAAAAGCUAUUGUUUACAATT | 270 | AAUUGUAAACAAUAGCUUUUUCUUCCC | 560 |
| S271-AS561-M1 | AAGAAAAAGCUAUUGUUUUACAAUTA | 271 | UAAUUGUAAACAAUAGCUUUUUCUUCC | 561 |
| S272-AS562-M1 | AGAAAAAGCUAUUGUUUACAAUUAT | 272 | AUAAUUGUAAACAAUAGCUUUUUCUUC | 562 |
| S273-AS563-M1 | GAAAAAGCUAUUGUUUACAAUUATA | 273 | UAUAAUUGUAAACAAUAGCuuuuucuu | 563 |
| S274-AS564-M1 | AAAAAGCUAUUGUUUACAAUUAUAT | 274 | AUAUAAUUGUAAACAAUAGCUUUUUCU | 564 |
| S275-AS565-M1 | AAAAGCUAUUGUUUACAAUUAUAUC | 275 | GAUAUAAUUGUAAACAAUAGCUUUUUC | 565 |
| S276-AS566-M1 | AAAGCUAUUGUUUACAAUUAUAUCA | 276 | UGAUAUAAUUGUAAACAAUAGCUUUUU | 566 |
| S277-AS567-M1 | AAGCUAUUGUUUACAAUUAUAUCAC | 277 | GUGAUAUAAUUGUAAACAAUAGCUUUU | 567 |
| S278-AS568-M1 | AGCUAUUGUUUACAAUUAUAUCACC | 278 | GGUGAUAUAAUUGUAAACAAUAGCUUU | 568 |
| S279-AS569-M1 | GCUAUUGUUUACAAUUAUAUCACCA | 279 | UGGUGAUAUAAUUGUAAACAAUAGCUU | 569 |
| S280-AS570-M1 | CUAUUGUUUACAAUUAUAUCACCAT | 280 | AUGGUGAUAUAAUUGUAAACAAUAGCU | 570 |
| S281-AS571-M1 | UAUUGUUUACAAUUAUAUCACCATT | 281 | AAUGGUGAUAUAAUUGUAAACAAUAGC | 571 |
| S282-AS572-M1 | AUUGUUUACAAUUAUAUCACCAUTA | 282 | UAAUGGUGAUAUAAUUGUAACAAUAG | 572 |
| S283-AS573-M1 | UUGUUUACAAUUAUAUCACCAUUAA | 283 | UUAAUGGUGAUAUAAUUGUAAACAAUA | 573 |
| S284-AS574-M1 | UGUUUACAAUUAUAUCACCAUUAAG | 284 | CUUAAUGGUGAUAUAAUUGUAAACAAU | 574 |
| S285-AS575-M1 | GUUUACAAUUAUAUCACCAUUAAGG | 285 | CCUUAAUGGUGAUAUAAUUGUAAACAA | 575 |
| S286-AS576-M1 | UACAAUUAUAUCACCAUUAAGGCAA | 286 | UUGCCUUAAUGGUGAUAUAAUUGUAAA | 576 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S287-AS577-M1 | AUUAUAUCACCAUUAAGGCAACUGC | 287 | GCAGUUGCCUUAAUGGUGAUAUAAUUG | 577 |
| S288-AS578-M1 | ACUGCUACACCCUGCUUUGUAUUCT | 288 | AGAAUACAAAGCAGGGUGUAGCAGUUG | 578 |
| S289-AS579-M1 | CUGCUACACCCUGCUUUGUAUUCTG | 289 | CAGAAUACAAAGCAGGGUGUAGCAGUU | 579 |
| S290-AS580-M1 | UGCUACACCCUGCUUUGUAUUCUGG | 290 | CCAGAAUACAAAGCAGGGUGUAGCAGU | 580 |
| S581-AS591- | UUCAUAAACAAUGAAUGGCAGCAGCCGAAAGGCUGC | 581 | UGCCAUUCAUUGUUUAUGAAGG | 591 |
| S582-AS592- | UCAUAAACAAUGAAUGGCAAGCAGCCGAAAGGCUGC | 582 | UUGCCAUUCAUUGUUUAUGAGG | 592 |
| S583-AS593-M2 | GAAACGUGGUUGUGAUGAAGGCAGCCGAAAGGCUGC | 583 | CUUCAUCACAACCACGUUUCGG | 593 |
| S583-AS593-M3 | GAAACGUGGUUGUGAUGAAGGCAGCCGAAAGGCUGC | 583 | CUUCAUCACAACCACGUUUCGG | 593 |
| S583-AS593-M4 | GAAACGUGGUUGUGAUGAAGGCAGCCGAAAGGCUGC | 583 | CUUCAUCACAACCACGUUUCGG | 593 |
| S583-AS593-M5 | GAAACGUGGUUGUGAUGAAGGCAGCCGAAAGGCUGC | 583 | CUUCAUCACAACCACGUUUCGG | 593 |
| S583-AS593-M6 | GAAACGUGGUUGUGAUGAAGGCAGCCGAAAGGCUGC | 583 | CUUCAUCACAACCACGUUUCGG | 593 |
| S583-AS593-M7 | GAAACGUGGUUGUGAUGAAGGCAGCCGAAAGGCUGC | 583 | CUUCAUCACAACCACGUUUCGG | 593 |
| S584-AS594-M2 | GUUGUGAUGAAGGUAGCUGAGCAGCCGAAAGGCUGC | 584 | UCAGCUACCUUCAUCACAACGG | 594 |
| S584-AS594-M3 | GUUGUGAUGAAGGUAGCUGAGCAGCCGAAAGGCUGC | 584 | UCAGCUACCUUCAUCACAACGG | 594 |
| S584-AS594-M4 | GUUGUGAUGAAGGUAGCUGAGCAGCCGAAAGGCUGC | 584 | UCAGCUACCUUCAUCACAACGG | 594 |
| S584-AS594-M5 | GUUGUGAUGAAGGUAGCUGAGCAGCCGAAAGGCUGC | 584 | UCAGCUACCUUCAUCACAACGG | 594 |
| S584-AS594-M6 | GUUGUGAUGAAGGUAGCUGAGCAGCCGAAAGGCUGC | 584 | UCAGCUACCUUCAUCACAACGG | 594 |
| S584-AS594-M7 | GUUGUGAUGAAGGUAGCUGAGCAGCCGAAAGGCUGC | 584 | UCAGCUACCUUCAUCACAACGG | 594 |
| S585-AS595-M2 | GGUGGAUGAAACUCAGUUUAGCAGCCGAAAGGCUGC | 585 | UAAACUGAGUUUCAUCCACCGG | 595 |
| S585-AS595-M3 | GGUGGAUGAAACUCAGUUUAGCAGCCGAAAGGCUGC | 585 | UAAACUGAGUUUCAUCCACCGG | 595 |
| S585-AS595-M4 | GGUGGAUGAAACUCAGUUUAGCAGCCGAAAGGCUGC | 585 | UAAACUGAGUUUCAUCCACCGG | 595 |
| S585-AS595-M5 | GGUGGAUGAAACUCAGUUUAGCAGCCGAAAGGCUGC | 585 | UAAACUGAGUUUCAUCCACCGG | 595 |
| S585-AS595-M6 | GGUGGAUGAAACUCAGUUUAGCAGCCGAAAGGCUGC | 585 | UAAACUGAGUUUCAUCCACCGG | 595 |
| S585-AS595-M7 | GGUGGAUGAAACUCAGUUUAGCAGCCGAAAGGCUGC | 585 | UAAACUGAGUUUCAUCCACCGG | 595 |
| S585-AS595-M8 | GGUGGAUGAAACUCAGUUUAGCAGCCGAAAGGCUGC | 585 | UAAACUGAGUUUCAUCCACCGG | 595 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S585-AS595-M9 | GGUGGAUGAAACUCAGUU UAGCAGCCGAAAGGCUGC | 585 | UAAACUGAGUUUCAUCCAC CGG | 595 |
| S585-AS595-M10 | GGUGGAUGAAACUCAGUU UAGCAGCCGAAAGGCUGC | 585 | UAAACUGAGUUUCAUCCAC CGG | 595 |
| S585-AS595-M11 | GGUGGAUGAAACUCAGUU UAGCAGCCGAAAGGCUGC | 585 | UAAACUGAGUUUCAUCCAC CGG | 595 |
| S586-AS596-M2 | CAGUUUAAGAAGAUCCUC GGGCAGCCGAAAGGCUGC | 586 | CCGAGGAUCUUCUUAAACU GGG | 596 |
| S586-AS596-M3 | CAGUUUAAGAAGAUCCUC GGGCAGCCGAAAGGCUGC | 586 | CCGAGGAUCUUCUUAAACU GGG | 596 |
| S586-AS596-M4 | CAGUUUAAGAAGAUCCUC GGGCAGCCGAAAGGCUGC | 586 | CCGAGGAUCUUCUUAAACU GGG | 596 |
| S586-AS596-M5 | CAGUUUAAGAAGAUCCUC GGGCAGCCGAAAGGCUGC | 586 | CCGAGGAUCUUCUUAAACU GGG | 596 |
| S586-AS596-M6 | CAGUUUAAGAAGAUCCUC GGGCAGCCGAAAGGCUGC | 586 | CCGAGGAUCUUCUUAAACU GGG | 596 |
| S586-AS596-M7 | CAGUUUAAGAAGAUCCUC GGGCAGCCGAAAGGCUGC | 586 | CCGAGGAUCUUCUUAAACU GGG | 596 |
| S586-AS596-M12 | CAGUUUAAGAAGAUCCUC GGGCAGCCGAAAGGCUGC | 586 | CCGAGGAUCUUCUUAAACU GGG | 596 |
| S587-AS597-M2 | UUUAAGAAGAUCCUCGGC UAGCAGCCGAAAGGCUGC | 587 | UAGCCGAGGAUCUUCUUAA AGG | 597 |
| S587-AS597-M3 | UUUAAGAAGAUCCUCGGC UAGCAGCCGAAAGGCUGC | 587 | UAGCCGAGGAUCUUCUUAA AGG | 597 |
| S587-AS597-M4 | UUUAAGAAGAUCCUCGGC UAGCAGCCGAAAGGCUGC | 587 | UAGCCGAGGAUCUUCUUAA AGG | 597 |
| S587-AS597-M5 | UUUAAGAAGAUCCUCGGC UAGCAGCCGAAAGGCUGC | 587 | UAGCCGAGGAUCUUCUUAA AGG | 597 |
| S587-AS597-M6 | UUUAAGAAGAUCCUCGGC UAGCAGCCGAAAGGCUGC | 587 | UAGCCGAGGAUCUUCUUAA AGG | 597 |
| S587-AS597-M7 | UUUAAGAAGAUCCUCGGC UAGCAGCCGAAAGGCUGC | 587 | UAGCCGAGGAUCUUCUUAA AGG | 597 |
| S587-AS597-M13 | UUUAAGAAGAUCCUCGGC UAGCAGCCGAAAGGCUGC | 587 | UAGCCGAGGAUCUUCUUAA AGG | 597 |
| S588-AS598-M2 | GUUCUAGAAUUUGAAUUG AUGCAGCCGAAAGGCUGC | 588 | AUCAAUUCAAAUUCUAGAA CGG | 598 |
| S588-AS598-M3 | GUUCUAGAAUUUGAAUUG AUGCAGCCGAAAGGCUGC | 588 | AUCAAUUCAAAUUCUAGAA CGG | 598 |
| S588-AS598-M4 | GUUCUAGAAUUUGAAUUG AUGCAGCCGAAAGGCUGC | 588 | AUCAAUUCAAAUUCUAGAA CGG | 598 |
| S588-AS598-M5 | GUUCUAGAAUUUGAAUUG AUGCAGCCGAAAGGCUGC | 588 | AUCAAUUCAAAUUCUAGAA CGG | 598 |
| S588-AS598-M6 | GUUCUAGAAUUUGAAUUG AUGCAGCCGAAAGGCUGC | 588 | AUCAAUUCAAAUUCUAGAA CGG | 598 |
| S588-AS598-M7 | GUUCUAGAAUUUGAAUUG AUGCAGCCGAAAGGCUGC | 588 | AUCAAUUCAAAUUCUAGAA CGG | 598 |
| S589-AS599-M2 | CCUUUUAAACGACAACAAU AGCAGCCGAAAGGCUGC | 589 | UAUUGUUGUCGUUUAAAAG GGG | 599 |

TABLE 4-continued

ALDH2 RNAi Oligonucleotide Sequences

| App Name | Sense Sequence/ Mrna seq | S SEQ ID NO | Antisense Sequence | AS SEQ ID NO |
|---|---|---|---|---|
| S589-AS599-M3 | CCUUUUAAACGACAACAAU AGCAGCCGAAAGGCUGC | 589 | UAUUGUUGUCGUUUAAAAG GGG | 599 |
| S589-AS599-M4 | CCUUUUAAACGACAACAAU AGCAGCCGAAAGGCUGC | 589 | UAUUGUUGUCGUUUAAAAG GGG | 599 |
| S589-AS599-M5 | CCUUUUAAACGACAACAAU AGCAGCCGAAAGGCUGC | 589 | UAUUGUUGUCGUUUAAAAG GGG | 599 |
| S589-AS599-M6 | CCUUUUAAACGACAACAAU AGCAGCCGAAAGGCUGC | 589 | UAUUGUUGUCGUUUAAAAG GGG | 599 |
| S589-AS599-M7 | CCUUUUAAACGACAACAAU AGCAGCCGAAAGGCUGC | 589 | UAUUGUUGUCGUUUAAAAG GGG | 599 |
| S590-AS600-M2 | AUGAUUUUUAAAAAAUAG AUGCAGCCGAAAGGCUGC | 590 | AUCUAUUUUUUAAAAAUCA UGG | 600 |
| S590-AS600-M3 | AUGAUUUUUAAAAAAUAG AUGCAGCCGAAAGGCUGC | 590 | AUCUAUUUUUUAAAAAUCA UGG | 600 |
| S590-AS600-M4 | AUGAUUUUUAAAAAAUAG AUGCAGCCGAAAGGCUGC | 590 | AUCUAUUUUUUAAAAAUCA UGG | 600 |
| S590-AS600-M5 | AUGAUUUUUAAAAAAUAG AUGCAGCCGAAAGGCUGC | 590 | AUCUAUUUUUUAAAAAUCA UGG | 600 |
| S590-AS600-M6 | AUGAUUUUUAAAAAAUAG AUGCAGCCGAAAGGCUGC | 590 | AUCUAUUUUUUAAAAAUCA UGG | 600 |
| S590-AS600-M7 | AUGAUUUUUAAAAAAUAG AUGCAGCCGAAAGGCUGC | 590 | AUCUAUUUUUUAAAAAUCA UGG | 600 |

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide for reducing expression of ALDH2 in the liver, the oligonucleotide comprising an antisense strand of 22 to 30 nucleotides in length, wherein the antisense strand has a region of complementarity to a target sequence of ALDH2 as set forth in any one of SEQ ID NOs: 601-607, wherein the region of complementarity is at least 15 contiguous nucleotides in length, and wherein the antisense strand comprises a sequence as set forth in any one of SEQ ID NOs: 591-600.

2. The oligonucleotide of claim 1, wherein the region of complementarity is fully complementary to the target sequence of ALDH2.

3. The oligonucleotide of claim 1, further comprising a sense strand of 15 to 40 nucleotides in length, wherein the sense strand forms a duplex region with the antisense strand.

4. The oligonucleotide of claim 3, wherein the duplex region is at least 19 nucleotides in length.

5. The oligonucleotide of claim 1, wherein the region of complementarity to ALDH2 is at least 19 contiguous nucleotides in length.

6. The oligonucleotide of claim 3, wherein the sense strand comprises a sequence as set forth in any one of SEQ ID NOs: 581-590.

7. The oligonucleotide of claim 3, wherein the sense strand consists of a sequence as set forth in any one of SEQ ID NOs: 581-590.

8. The oligonucleotide of claim 1, wherein the antisense strand consists of a sequence as set forth in any one of SEQ ID NOs: 591-600.

9. The oligonucleotide of claim 3, wherein the sense strand comprises at its 3'-end a stem-loop set forth as: S1-L-S2, wherein S1 is complementary to S2, and wherein L forms a loop between S1 and S2 of 3 to 5 nucleotides in length.

10. An oligonucleotide for reducing expression of ALDH2 in the liver, the oligonucleotide comprising an antisense strand and a sense strand,
wherein the antisense strand is 21 to 27 nucleotides in length and has a region of complementarity to a target sequence of ALDH2 as set forth in any one of SEQ ID NOs: 601-607, wherein the region of complementarity is at least 15 contiguous nucleotides in length, and wherein the antisense strand comprises a sequence as set forth in any one of SEQ ID NOs: 591-600,
wherein the sense strand comprises at its 3'-end a stem-loop set forth as: S1-L-S2, wherein S1 is complementary to S2, and wherein L forms a loop between S1 and S2 of 3 to 5 nucleotides in length,
and wherein the antisense strand and the sense strand form a duplex structure of at least 19 nucleotides in length.

11. The oligonucleotide of claim 10, wherein the region of complementarity is fully complementary to at least 19 contiguous nucleotides of ALDH2 mRNA.

12. The oligonucleotide of claim 9, wherein L is a tetraloop.

13. The oligonucleotide of claim 3, wherein the antisense strand is 27 nucleotides in length and the sense strand is 25 nucleotides in length.

14. The oligonucleotide of claim 13, wherein the antisense strand and sense strand form a duplex region of 25 nucleotides in length.

15. The oligonucleotide of claim 1, wherein the oligonucleotide comprises at least one modified nucleotide.

16. The oligonucleotide of claim 1, wherein the oligonucleotide comprises at least one modified internucleotide linkage.

17. The oligonucleotide of claim 1, wherein at least one nucleotide of the oligonucleotide is conjugated to one or more targeting ligands.

18. A pharmaceutical composition comprising the oligonucleotide of claim 1, and a pharmaceutically acceptable excipient.

19. The oligonucleotide of claim 10, wherein the oligonucleotide comprises at least one modified nucleotide.

20. The oligonucleotide of claim 10, wherein the oligonucleotide comprises at least one modified internucleotide linkage.

21. The oligonucleotide of claim 10, wherein at least one nucleotide of the oligonucleotide is conjugated to one or more targeting ligands.

22. The oligonucleotide of claim 17, wherein each targeting ligand comprises a N-acetylgalactosamine (GalNAc) moiety.

23. The oligonucleotide of claim 21, wherein each targeting ligand comprises a N-acetylgalactosamine (GalNAc) moiety.

24. The oligonucleotide of claim 10, wherein the sense strand comprises a sequence as set forth in any one of SEQ ID NOs: 581-590.

25. A pharmaceutical composition comprising the oligonucleotide of claim 10, and a pharmaceutically acceptable excipient.

* * * * *